(12) United States Patent
Hobbs et al.

(10) Patent No.: US 7,034,056 B2
(45) Date of Patent: Apr. 25, 2006

(54) ARYL AND BIARYL COMPOUNDS HAVING MCH MODULATORY ACTIVITY

(75) Inventors: Douglas Walsh Hobbs, Yardley, PA (US); Tao Guo, Dayton, NJ (US); Rachael C. Hunter, Princeton, NJ (US); Huizhong Gu, Monmouth Junction, NJ (US)

(73) Assignee: Pharmacopeia Drug Discovery, inc., Cranbury, NJ (US)

( * ) Notice: Subject to any disclaimer, the term of this patent is extended or adjusted under 35 U.S.C. 154(b) by 282 days.

(21) Appl. No.: 10/101,136

(22) Filed: Mar. 19, 2002

(65) Prior Publication Data

US 2003/0092715 A1 May 15, 2003

Related U.S. Application Data

(60) Provisional application No. 60/277,534, filed on Mar. 21, 2001.

(51) Int. Cl.
*A61K 31/17* (2006.01)
*C07C 275/40* (2006.01)

(52) U.S. Cl. .......................... 514/596; 558/393; 564/50

(58) Field of Classification Search ................. 564/50; 514/596; 558/393
See application file for complete search history.

(56) References Cited

U.S. PATENT DOCUMENTS

| 3,455,940 A | 7/1969 | Stecker |
| 6,043,246 A | 3/2000 | Fukami et al. |

FOREIGN PATENT DOCUMENTS

| EP | 0068669 | 5/1983 |
| EP | 428434 A | 5/1991 |
| EP | 0432 442 | 6/1991 |
| EP | 474561 A1 | 3/1992 |
| EP | 515240 A1 | 11/1992 |
| EP | 559538 A1 | 9/1993 |
| EP | 0955 293 | 10/1999 |
| FR | 2717802 A1 | 9/1995 |
| WO | WO 00/06545 | 2/2000 |
| WO | WO 00/27845 | 3/2000 |
| WO | WO 00/25786 | 5/2000 |

OTHER PUBLICATIONS

Clinical Science (2001), 100(2), 221-229.*
Psychopharmacology (2003) 167: 103-111.*
Proceedings of the National Academy of Sciences of the United States of America (2003), 100(17), 10085-10090.*
Shimada, et al., *Nature*, vol. 396(Dec. 17, 1998), pp. 670-673.
Edstrom, E.D. & Livinghouse, T., *J.Am. Chem. Soc.* (1986), 1334-6.
Kano, et al., *Chem. Pharm. Bull.*, 1985, 33, 340-6.
Suzuki, A., *J. Amer. Chem. Soc.*, 111 (1989) 314.
Zhang, A.J., et, *Tet. Lett.* (1998), 39, 7439-7442.
Igarashi, Yakagaku Zassi, "Synthesis and pharmacology of basic . . . ", (1973) vol. 93, No. 5,pp. 554-565.
Schultz, Helvetica Chimica Acta, "Total synthesis of (+)-8S, 13R)—cyclocelabenzine" (1996) vol. 79, No. 5, pp. 1295-1304.
Cherkashin, Dokl. Chem. (1990) vol. 313, No. 1, 3, pp 206-209.
Julia, Bull. Soc. Chim. Fr., (1966), pp. 1335-1342.
Ornstein, J. Med. Chem., "Biarylpropylsulfonamides as Novel, Potent . . . ", (2000) No. 43, p. 4356, Example 5G, Table 1.
O'Brien, J. Med. Chem, "Inhibitors of acyl-CoA:cholesterol O-acyl . . . " (1994), vol. 37, No. 12, pp. 1810-1822.
Leb, Life Sciences, "Melanin Concentrating Hormone Analogues" (1989) vol. 44, No. 7, pp. 451-457.
DeGraw, BNSDOCID, "Histamine Releasers" (1967) vol. 10, pp. 174-177.
BNSDOCID, XP 2208310A.

* cited by examiner

*Primary Examiner*—Kamal A. Saeed
*Assistant Examiner*—Rebecca Anderson
(74) *Attorney, Agent, or Firm*—Palaiyur S. Kalyanaraman

(57) ABSTRACT

In one embodiment, this invention provides a novel class of compounds as antagonists of the MCH receptor, methods of preparing such compounds, pharmaceutical compositions containing one or more of the compounds, methods of preparing pharmaceutical formulations comprising one or more such compounds, and methods of treatment, prevention or amelioration or one or more of diseases associated with the MCH receptor. An illustrative inventive compound is shown below:

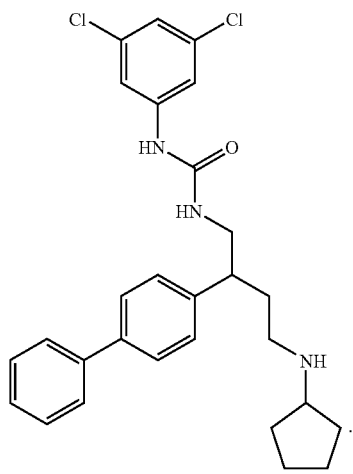

26 Claims, No Drawings

ARYL AND BIARYL COMPOUNDS HAVING MCH MODULATORY ACTIVITY

FIELD OF THE INVENTION

The present invention relates to antagonists for melanin-concentrating hormone (MCH) and their use in the treatment of obesity, diabetes and related disorders. It generally discloses novel compounds having MCH receptor modulatory activity, pharmaceutical compositions containing one or more such modulators, methods of preparing such modulators and methods of using such modulators to treat obesity, diabetes and related disorders. The invention specifically discloses certain novel aryl and biaryl compounds. This application claims priority from U.S. provisional patent application, Serial No. 60/277,534 filed Mar. 21, 2001.

BACKGROUND OF THE INVENTION

MCH, a 19-amino acid cyclic peptide, was first identified over a decade ago in teleost fish where it appears to regulate color change. More recently, MCH which is synthesized mainly in the lateral hypothalamus, a brain center regulating feeding behavior, has been the subject of investigation for its possible role as a regulator of eating behavior in mammals. Central administration of MCH is known to stimulate food intake and promote fat storage in rodents. It is also known that mice that overexpress MCH are obese. As reported by Shimada et al., *Nature*, Vol. 396 (Dec. 17, 1998), pp. 670–673, MCH-deficient mice have reduced body weight and leanness due to hypophagia (reduced feeding). In view of their findings, the authors have suggested that antagonists of MCH action may be effective for the treatment of obesity. U.S. Pat. No. 5,908,830 discloses a combination therapy for the treatment of diabetes or obesity involving the administration of a metabolic rate increasing agent and a feeding behavior modifying agent, an example of the latter being an MCH antagonist. U.S. Pat. No. 6,043,246 discloses urea derivatives said to be useful as neuropeptide Y receptor antagonists and as agents for the treatment of, inter alia, diseases of the metabolic system including obesity and diabetes. Published PCT patent application WO 00/27845 describes a class of compounds, characterized therein as spiroindolines, said to be selective neuropeptide Y Y5 antagonists and useful for the treatment of obesity and the complications associated therewith. Commonly assigned, copending U.S. provisional patent application Ser. No. 60/232,255, filed Sep. 14, 2000, discloses and claims aryl-substituted urea neuropeptide Y Y5 antagonists and their use in the treatment of obesity, hyperphagia (increased feeding) and diabetes.

GB-2304714A (Assignee: Sanofi) discloses piperidine derivatives of the formula:

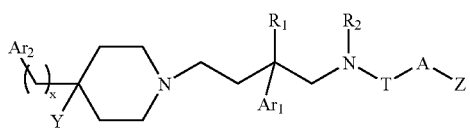

where the various moieties are as defined.

FR 2717802-A1 discloses piperidines of the formula:

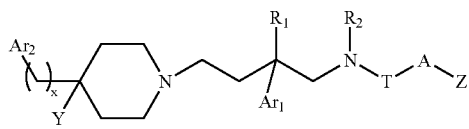

where the various moieties are as defined.

EP 428434-A discloses piperidines and piperazines of the formula:

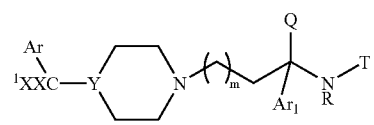

where the various moieties are as defined.

EP 515240-A1 discloses compounds of the formula:

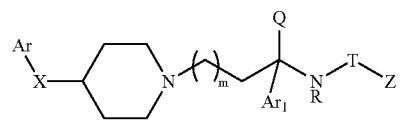

where the various moieties are as defined.

EP 559538-A1 discloses compounds of the formula:

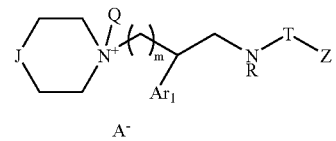

where the various moieties are as defined.

EP 474561-A1 discloses compounds of the formula:

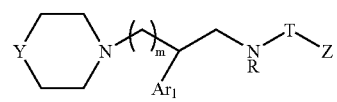

where the various moieties are as defined.

There is a need for new compounds, formulations, treatments and therapies for MCH receptor modulation, diabetes and related disorders. It is, therefore, an object of this invention to provide compounds useful in the treatment or prevention or amelioration of such disorders.

A further object of the present invention is to provide methods for modulating the MCH receptor using the compounds and pharmaceutical compositions provided herein.

Another object herein is to provide methods of modulating MCH receptors using the compounds provided herein.

SUMMARY OF THE INVENTION

In its many embodiments, the present invention provides a novel class of compounds as antagonists of MCH receptor, methods of preparing such compounds, pharmaceutical compositions containing one or more such compounds, methods of preparing pharmaceutical formulations comprising one or more such compounds, and methods of treatment, prevention or amelioration of one or more diseases associated with the MCH receptor. In one embodiment, the present application discloses a compound, including enantiomers, stereoisomers, rotamers, tautomers and prodrug of said compound, and pharmaceutically acceptable salts or solvates of said compound or of said prodrug, said compound having the general structure shown in Formula I:

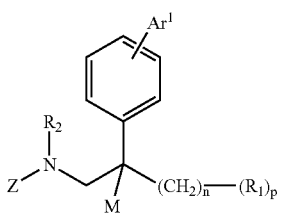

Formula I wherein:
$Ar^1$=unsubstituted or substituted phenyl, pyridine, pyridine-N-oxide, pyrazine or pyridazine, wherein the substituents number from 0 to 5, may be the same or different and are independently selected from the group consisting of H, CN, $OCF_3$, F, Cl, Br, I, $CONH_2$, methylenedioxy, OR, $CO_2H$, $CO_2R$, and OH with R being a $C_1$–$C_6$ straight chain alkyl or branched alkyl or a $C_3$–$C_7$ cycloalkyl;
M is H or R;
Z=

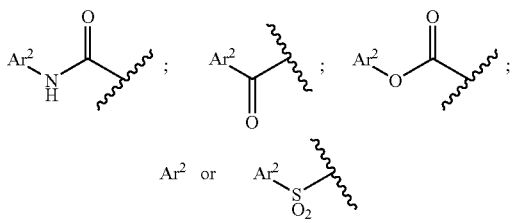

where $Ar^2$ is an unsubstituted or substituted phenyl wherein the substituents number from 0 to 5, may be the same or different and are independently selected from the group consisting F, Cl, Br, I, R, OR, $NO_2$, and $CF_3$;
n=0 to 6;
p=1–6;
$R_1$ may be the same or different and is independently selected from the group consisting of R; $NH_2$; NHR; $N(R)_2$; $N(R)_2 \rightarrow O$; $NH(CH_2)_nOR$; $N(R)SO_2R$; $NH(CH_2)_n$—$N(R)_2$; $N(R)SO_2(R)$;

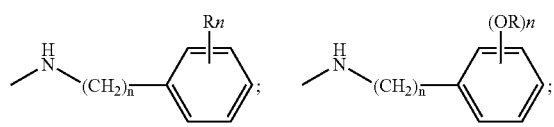

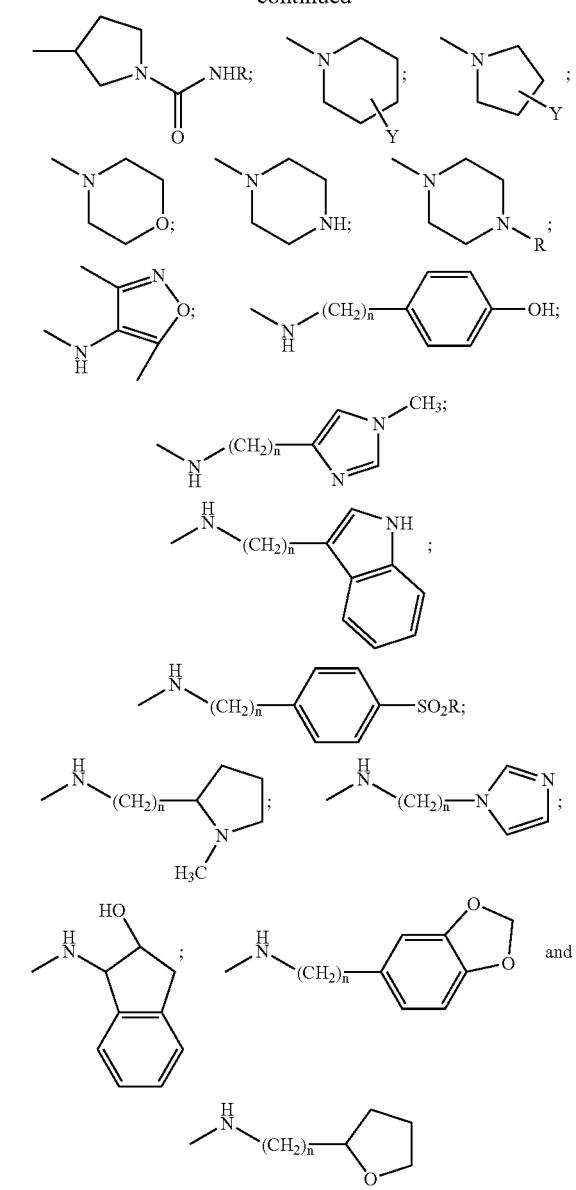

where n is defined above and where Y is a moiety numbering 0 to 5 which may be the same or different and are independently selected from the group consisting of H; OH; $NH_2$;

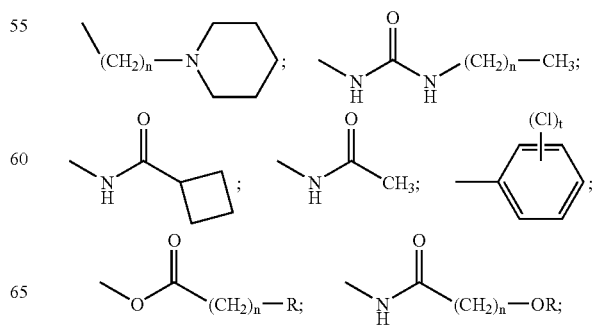

-continued

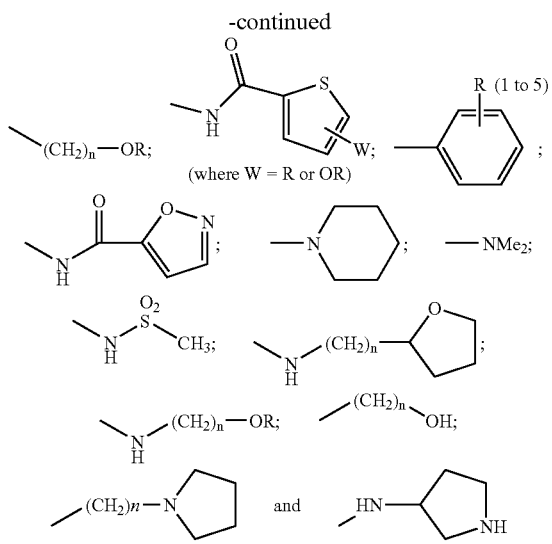

where n is defined above and t=1 to 5;

and $R_2$ is H or alkyl

The preferred representations for the various functionalities in Formula I are: For $Ar^1$: phenyl or pyridyl (more preferably 4-phenyl or 4-pyridyl on the ring in Formula I), with one or more substituents on said phenyl or pyridyl independently selected from the group consisting of CN, $OCF_3$ and halogen, more preferably a phenyl with substituents selected from CN, $OCF_3$, F and Cl, and still more preferably when at least one of these preferred substituents is in position 3 or position 4 on the ring with respect to said ring's attachment to the benzylic position shown in Formula I.

For Z: $Ar^2$—NH—CO, where $Ar^2$ is a phenyl which may optionally be substituted with 1–5 moieties such as a halogen, $OCH_3$ or $CF_3$, more preferably the substituent being F, Cl or $OCH_3$.

For R: preferably a $C_1$–$C_4$ straight chain or branched alkyl or a $C_3$–$C_7$ cycloalkyl.

For n: preferably 1–6, more preferably 2–4, and still more preferably 2.

For M: H.

For $R_1$: preferably selected from the group consisting of NHR; $N(R)_2$; $N(R)_2 \rightarrow O$; $NH(CH_2)_n OCH_3$; $N(R)SO_2R$; $NH(CH_2)_n—N(R)_2$; $N(R)SO_2(R)$;

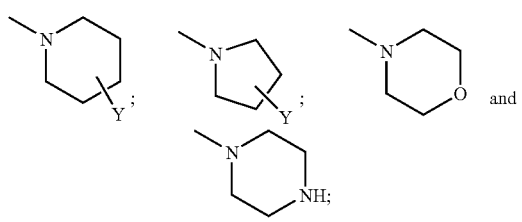

with the more preferable moieties being NHMe; NHEt; $NMe_2$; $NH(CH_2)_nOCH_3$; NH-cyclopropyl; NH-cyclobutyl; NH-cyclopentyl; $NH(CH_2)_3NMe_2$; and

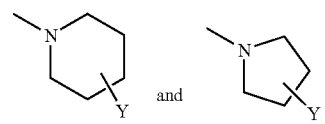

where Y and n are as defined above.

For Y: preferably the moieties $NH_2$; $NMe_2$; NHMe;

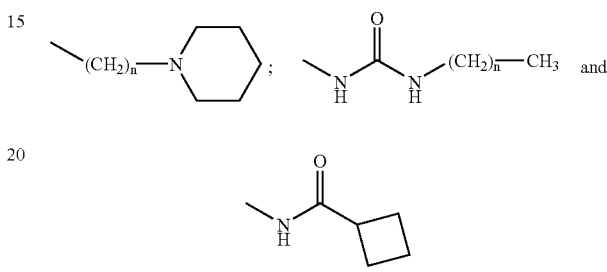

The present invention also discloses a compound, including enantiomers, stereoisomers, rotamers, tautomers and prodrug of said compound, and pharmaceutically acceptable salts or solvates of said compound or of said prodrug, said compound having the general structure shown in Formula II:

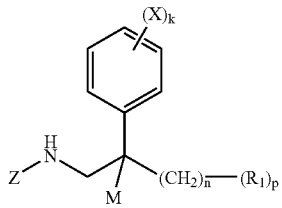

Formula II where M, Z, n, p and $R_1$ are defined above along with their preferences; k is a number from 0 to 5. X may be the same or different, and is independently selected from the group consisting of:

H, Cl, F, Br, I, R, OR, $CF_3$, $OCF_3$, methylenedioxy,

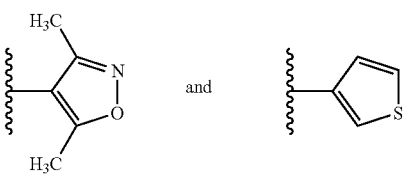

with the preferred moieties for X being R, H, Cl, $CF_3$ and $OCF_3$. The number k is preferably 1–3.

The present invention additionally discloses a compound, including enantiomers, stereoisomers, rotamers, tautomers and prodrug of said compound, and pharmaceutically acceptable salts or solvates of said compound or of said prodrug, said compound having the general structure shown in Formula III:

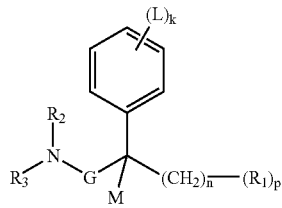

Formula III where M, n, p and $R_1$ are defined above along with their preferences. $R_2$ is H or alkyl and k is a number 0 to 5. G is —$CH_2$—, —C(O)— or —C(O)—O— with the —C(O) linked to the N($R_1R_2$) in the figure. $R_3$ is an alkyl, aryl, arylalkyl or alkylaryl. L may be the same or different and is independently selected from the group consisting of H, aryl, alkyl, halogen, alkoxy, aryloxy, arylalkoxy, alkylaryloxy, hydroxy, carboxy, carboalkoxy, cyano, $CF_3$ and $NO_2$.

The ring moieties in the inventive compounds may optionally carry substituents or additional substituents on the ring. Such substituents may be, for example, R, halogen, alkoxy, aryloxy, arylalkoxy, alkylaryloxy, hydroxy, carboxy, carboalkoxy, cyano, trifluoroalkyl, nitro and the like.

Also included in the invention are tautomers, rotamers, enantiomers and other optical isomers of compounds of Formula I, Formula II and Formula III where applicable, pharmaceutically acceptable salts, solvates and derivatives thereof, as well as prodrug of said compounds, and pharmaceutically acceptable salts, solvates and derivatives of said prodrug.

A further feature of the invention is pharmaceutical compositions containing as active ingredient a compound of Formula I, Formula II or Formula III (or its salt, solvate or isomers) together with a pharmaceutically acceptable carrier or excipient.

The invention also provides methods for preparing compounds of Formula I, Formula II and Formula III, as well as methods for treating diseases such as, for example, obesity and related disorders. The methods for treating comprise administering to a patient suffering from said disease or diseases therapeutically effective amounts of a compound of Formula I, Formula II or Formula III, or of pharmaceutical compositions comprising a compound of Formula I, Formula II or Formula III. The term "Therapeutically effective amounts" refers to amounts of the compound that are effective to make the compound function as MCH modulator.

Also disclosed is the use of a compound of Formula I, Formula II or of Formula III for the manufacture of a medicament for treating obesity and related disorders.

In addition to monotherapies including the compound represented by Formula I, Formula II or Formula III, another aspect of this invention is combinations (such as, for example, dual combination therapy, three combination therapy and the like,) of therapeutically effective amounts of a compound of Formula I (or Formula II or Formula III), or a prodrug thereof, or a pharmaceutically acceptable salt of said compound or a pharmaceutically acceptable salt of said prodrug, and therapeutically effective amounts of one or more antiobesity/anorectic agent such as, for example, a $\beta_3$ agonist, a thyromimetic agent, or an NPY antagonist.

Still another aspect of this invention is a method for treating obesity comprising administering to a mammal (which term includes humans) in need of such treatment:

a. therapeutically effective amounts of a first compound, said first compound being a Formula I compound (or a Formula II compound or a Formula III compound), a prodrug thereof, or a pharmaceutically acceptable salt of said compound or a pharmaceutically acceptable salt of said prodrug; and b. therapeutically effective amounts of a second compound, said second compound being an antiobesity and/or anorectic agent such as, for example, a $\beta_3$ agonist, a thyromimetic agent, or an NPY antagonist, wherein the amounts of the first and second compounds result in the desired therapeutic effect of treating obesity.

This invention is also directed to a pharmaceutical composition comprising a combination of therapeutically effective amounts of a first compound, said first compound being a Formula I compound (or a Formula II compound or a Formula III compound), a prodrug thereof, or a pharmaceutically acceptable salt of said compound or a pharmaceutically acceptable salt of said prodrug; and therapeutically effective amounts of a second compound, said second compound being an antiobesity and/or anorectic agent such as, for example, a $\beta_3$ agonist, a thyromimetic agent, or an NPY antagonist; and/or optionally a pharmaceutical acceptable carrier, vehicle or diluent.

Another aspect of this invention is a kit comprising:

a. therapeutically effective amounts of a first compound, said first compound being a Formula I compound (or a Formula II compound or a Formula III compound), a prodrug thereof, or a pharmaceutically acceptable salt of said compound or a pharmaceutically acceptable salt of said prodrug; and a pharmaceutically acceptable carrier, vehicle or diluent in a first unit dosage form;

b. therapeutically effective amounts of a second compound, said second compound being an antiobesity and/or anorectic agent such as, for example, a $\beta_3$ agonist, a thyromimetic agent, or an NPY antagonist; and a pharmaceutically acceptable carrier, vehicle or diluent in a second unit dosage form; and c. means for containing said first unit dosage form and said second unit dosage form, wherein the amounts of the first compound and of the second compound result in the desired therapeutic effect of treating obesity.

Illustrative non-limiting examples of preferred antiobesity and/or anorectic agents in the above combination methods, combination compositions and combination kits include: phenylpropanolamine, ephedrine, pseudoephedrine, phentermine, a cholecystokinin-A (hereinafter referred to as CCK-A) agonist, a monoamine reuptake inhibitor (such as, for example, sibutramine), a sympathomimetic agent, a serotonergic agent (such as, for example, dexfenfluramine or fenfluramine), a dopamine agonist (such as, for example, bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as, for example, Exendin and ciliary neurotrophic factors such as, for example, Axokine.

Another aspect of this invention is a method for treating diabetes comprising administering to a mammal:

a. therapeutically effective amounts of a first compound, said first compound being a Formula I compound (or a Formula II compound or a Formula III compound), a prodrug thereof, or a pharmaceutically acceptable salt of said compound or a pharmaceutically acceptable salt of said prodrug; and b. therapeutically effective amounts of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in the therapeutic effect of treating diabetes.

This invention is also directed to a pharmaceutical composition comprising a combination of therapeutically effective amounts of a first compound, said first compound being a Formula I compound (or a Formula II compound or a Formula III compound), a prodrug thereof, or a pharmaceutically acceptable salt of said compound or a pharmaceutically acceptable salt of said prodrug; therapeutically effective amounts of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutically acceptable carrier, vehicle or diluent.

Another aspect of this invention is a kit comprising:

a. therapeutically effective amounts of a first compound, said first compound being a Formula I compound (or a Formula II compound or a Formula III compound), a prodrug thereof, or a pharmaceutically acceptable salt of said compound or a pharmaceutically acceptable salt of said prodrug; and a pharmaceutically acceptable carrier, vehicle or diluent in a first unit dosage form;

b. therapeutically effective amounts of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and a pharmaceutically acceptable carrier, vehicle or diluent in a second unit dosage form; and c. means for containing said first unit dosage form and said second unit dosage form, wherein the amounts of the first compound and of the second compound result in the desired therapeutic effect of treating diabetes.

DETAILED DESCRIPTION OF PREFERRED EMBODIMENTS

In one embodiment, the present invention discloses compounds of Formula I, Formula II or Formula III, or a pharmaceutically acceptable derivative thereof, as inhibitors of MCH receptor. The various definitions for the moieties in Formulas I, II and III are given above.

Unless defined otherwise, all technical and scientific terms used herein have the same meaning as is commonly understood by one of skill in the art to which this invention belongs. Thus, for example, the term alkyl (including the alkyl portions of alkoxy) refers to a monovalent group derived from a straight or branched chain saturated hydrocarbon by the removal of a single atom having from 1 to 8 carbon atoms, preferably from 1 to 6;

aryl—represents a carbocyclic group having from 6 to 14 carbon atoms and having at least one benzenoid ring, with all available substitutable aromatic carbon atoms of the carbocyclic group being intended as possible points of attachment. Preferred aryl groups include phenyl, 1-naphthyl, 2-naphthyl and indanyl, and especially phenyl and substituted phenyl;

aralkyl—represents a moiety containing an aryl group linked vial a lower alkyl;

alkylaryl—represents a moiety containing a lower alkyl linked via an aryl group;

cycloalkyl—represents a saturated carbocyclic ring having from 3 to 8 carbon atoms, preferably 5 or 6, optionally substituted.

heterocyclic—represents, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6- or 7-membered and may or may not have double bonds that lack delocalized pi electrons, which ring structure has from 2 to 8, preferably from 3 to 6 carbon atoms, e.g., 2- or 3-piperidinyl, 2- or 3-piperazinyl, 2- or 3-morpholinyl, or 2- or 3-thiomorpholinyl;

halogen—represents fluorine, chlorine, bromine and iodine;

heteroaryl—represents a cyclic organic group having at least one O, S and/or N atom interrupting a carbocyclic ring structure and having a sufficient number of delocalized pi electrons to provide aromatic character, with the aromatic heterocyclyl group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 4-imidazolyl, 2-, 4- or 5-pyrimidinyl, 2-pyrazinyl, or 3- or 4-pyridazinyl, etc.

Representative compounds of the invention which exhibit excellent MCH receptor modulatory activity are listed in Table I along with their activity (ranges of $K_i$ values in nanomolar, nM).

Depending upon the structure, the compounds of the invention may form pharmaceutically acceptable salts with organic or inorganic acids, or organic or inorganic bases. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. For formation of salts with bases, suitable bases are, for example, NaOH, KOH, $NH_4OH$, tetraalkylammonium hydroxide, and the like.

In another embodiment, this invention provides pharmaceutical compositions comprising the above-described inventive aryl or biaryl compounds as an active ingredient. The pharmaceutical compositions generally additionally comprise a pharmaceutically acceptable carrier diluent, excipient or carrier (collectively referred to herein as carrier materials). Because of their MCH inhibitory activity, such pharmaceutical compositions possess utility in treating obesity and related disorders.

In yet another embodiment, the present invention discloses methods for preparing pharmaceutical compositions comprising the inventive aryl or biaryl compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semisolid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. MCH inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

The compounds as well as the pharmaceutical formulations containing the inventive compounds may also be delivered subcutaneously.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the pharmaceutical compositions disclosed above for treatment of diseases such as, for example, obesity and the like. The method comprises administering a therapeutically effective amount of the inventive pharmaceutical composition to a patient having such a disease or diseases and in need of such a treatment.

As stated earlier, the invention also includes tautomers, enantiomers and other stereoisomers of the compounds where applicable. Thus, as one skilled in the art knows, some of the inventive compounds may exist in isomeric forms. Such variations are contemplated to be within the scope of the invention.

Another embodiment of the invention discloses a method of making the inventive aryl or biaryl compounds disclosed herein. The compounds may be prepared by several techniques known in the art. Representative illustrative procedures are outlined in the following reaction schemes.

REACTION SCHEMES

Abbreviations which are used in the descriptions of the schemes, preparations and the examples that follow are:

Abbreviation Used:
Ar=argon
Boc=tert-butyloxycarbonyl
tBuOH=tert-butanol
$CH_2Cl_2$=dichloromethane
$ClCH_2CH_2Cl$=1,2-dichloroethane
CDI=carbonyldiimidazole
DIC=1,3-dicyclohexylcarbodiimide
DMF=N,N-dimethylformamide
DIEA=N,N-diisopropylethylamine
Et=ethyl
EtOH=ethanol
EtOAc=ethyl acetate
HOBt=1-hydroxybenzotriazole
$H_2SO_4$=sulfuric acid
HCl=hydrogen chloride
$H_2O$=water
$K_2CO_3$=potassium carbonate
LDA=lithium diisopropylamide
LiOH=lithium hydroxide
$LiAlH_4$=lithium aluminum hydride
Me=methyl
MeI=methyl iodide
MeOH=methanol
$Me_2S$=dimethylsulfide
NMMO=4-methylmorpholine N-oxide
$Na(OAc)_3BH$=sodium triacetoxyborohydride
NaCl=sodium chloride
NaH=sodium hydride
$NaHCO_3$=sodium bicarbonate
$NaIO_4$=sodium periodate
$Na_2CO_3$=sodium carbonate
NaOH=sodium hydroxide
$Na_2SO_4$=sodium sulfate
$Na_2S_2O_3$=sodium thiosulfate
$O_3$=ozone
$O_2$=oxygen
$OsO_4$=osmium tetroxide
$Pd(PPh_3)_4$=tetrakis(triphenylphosphine)palladium(O)
$SOCl_2$=thionyl chloride
TEA=triethylamine
TFA=trifluoroacetic acid
TMSOTf=trimethylsilyl trifluoromethanesulfonate
THF=tetrahydrofuran
HMCHR—CHO=membranes prepared from Chinese hamster ovary cells that overexpress human melanin concentrating hormone.
WGA-SPA beads=Scintillation Assay beads labeled with wheat germ agglutinin
BSA=bovine serum albumin MCH=melanin concentrating hormone
MCHR=melanin concentrating hormone receptor Several methods for preparing the compounds of this invention and intermediates thereof are illustrated in the following reaction schemes. Starting materials are made using known procedures or as illustrated.

Reaction Schemes 1–2 may be used to synthesize reaction intermediates wherein the structures are aryl amines and aryl carboxylic acids. The synthetic methods used here are modified from known literature procedures, such as: (1) E. D. Edstrom and T. Livinghouse, *J. Am. Chem. Soc.* (1986), 1334–6; (2) C. P. Forbes and G. L. Wenteler, *J. Chem. Soc., Chem. Comm.*, (1986), 279–80; and (3) S. Kano et al., *Chem. Pharm. Bull.*, 1985, 33, 340–6.

In reaction Scheme 1, allylation of the arylacetonitrile may be accomplished using LDA to generate an anion followed by coupling with allyl iodide. The resulting 4-cyano-4-aryl-but-1-ene may be converted to an amine by reduction of the nitrile group by treatment with LiAlH$_4$ to form 5-amino-4-aryl-but-1-ene. Alternatively, the 4-cyano-4-aryl-but-1-ene may be further alkylated, as illustrated using LDA and MeI, to form 4-cyano-4-aryl-4-alkyl-but-1-ene. Reduction of the nitrile group using LiAlH$_4$ affords 5-amino-4-aryl-4-alkyl-but-1-ene.

In reaction Scheme 2, a commercially available aryl acetic acid is first converted to a methyl ester using MeOH/HCl(g). The methyl ester may be allylated using LDA and allyl iodide to form 2-arylpent-4-enoic acid methyl ester. The ester group may be hydrolyzed using a suitable base, such as LiOH in THF/H$_2$O, to form the carboxylic acid, which can be further converted to the acid chloride using SOCl$_2$. Alternatively, the 2-aryl-pent-4-enoic acid methyl ester may be further alkylated, as illustrated using LDA and MeI, to form 2-aryl-2-alkylpent-4-enoic acid methyl ester. The ester may be then hydrolyzed using a suitable base, such as LiOH in THF/H$_2$O, to form the corresponding carboxylic acid intermediate, which can be converted to the acid chloride using SOCl$_2$.

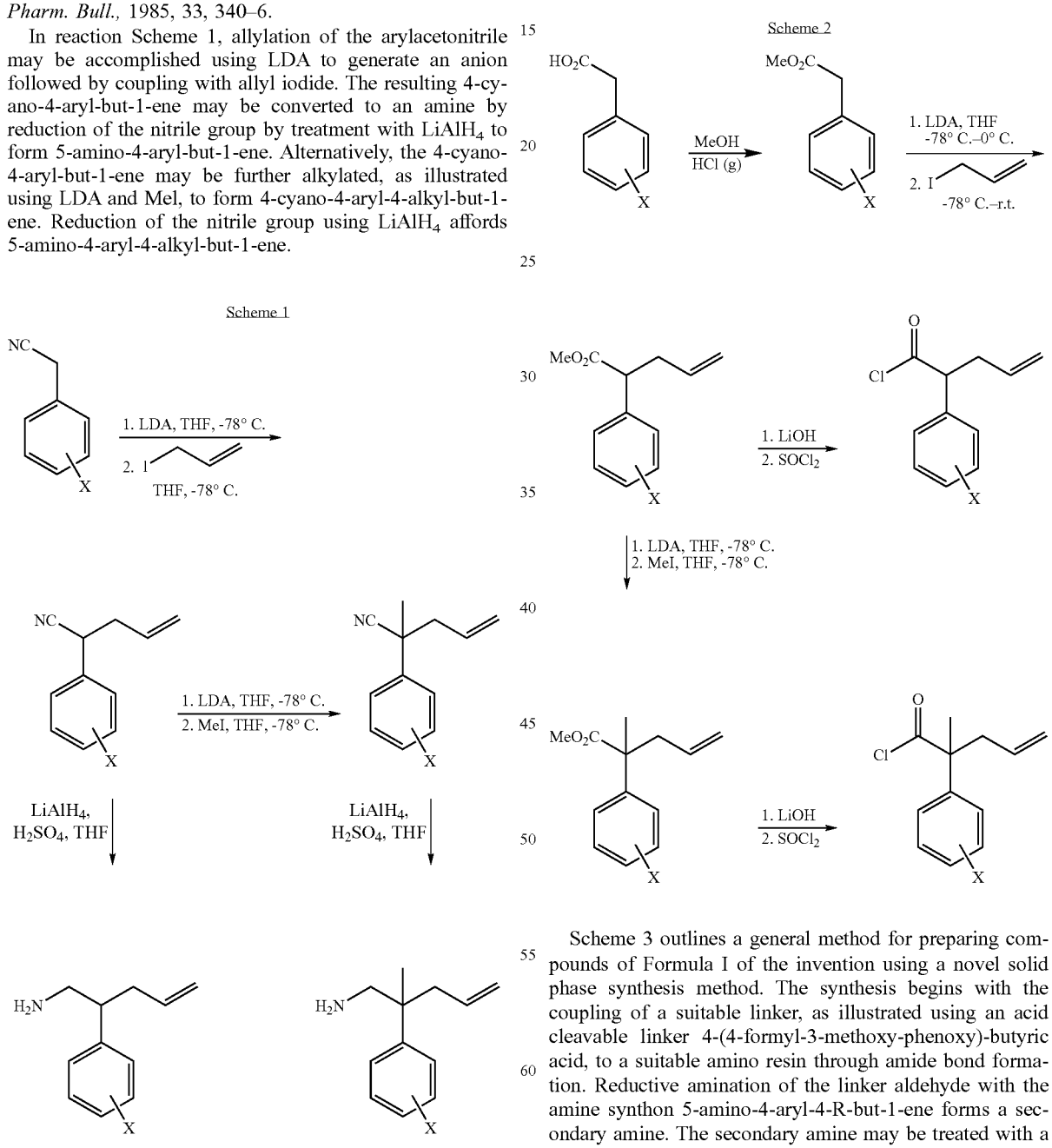

Scheme 3 outlines a general method for preparing compounds of Formula I of the invention using a novel solid phase synthesis method. The synthesis begins with the coupling of a suitable linker, as illustrated using an acid cleavable linker 4-(4-formyl-3-methoxy-phenoxy)-butyric acid, to a suitable amino resin through amide bond formation. Reductive amination of the linker aldehyde with the amine synthon 5-amino-4-aryl-4-R-but-1-ene forms a secondary amine. The secondary amine may be treated with a variety of agents such as an aryl or alkyl isocyanate, acid chloride, sulfonyl chloride, or chloroformate to form the corresponding urea, amide, sulfonamide, or carbamate intermediate A.

Scheme 3

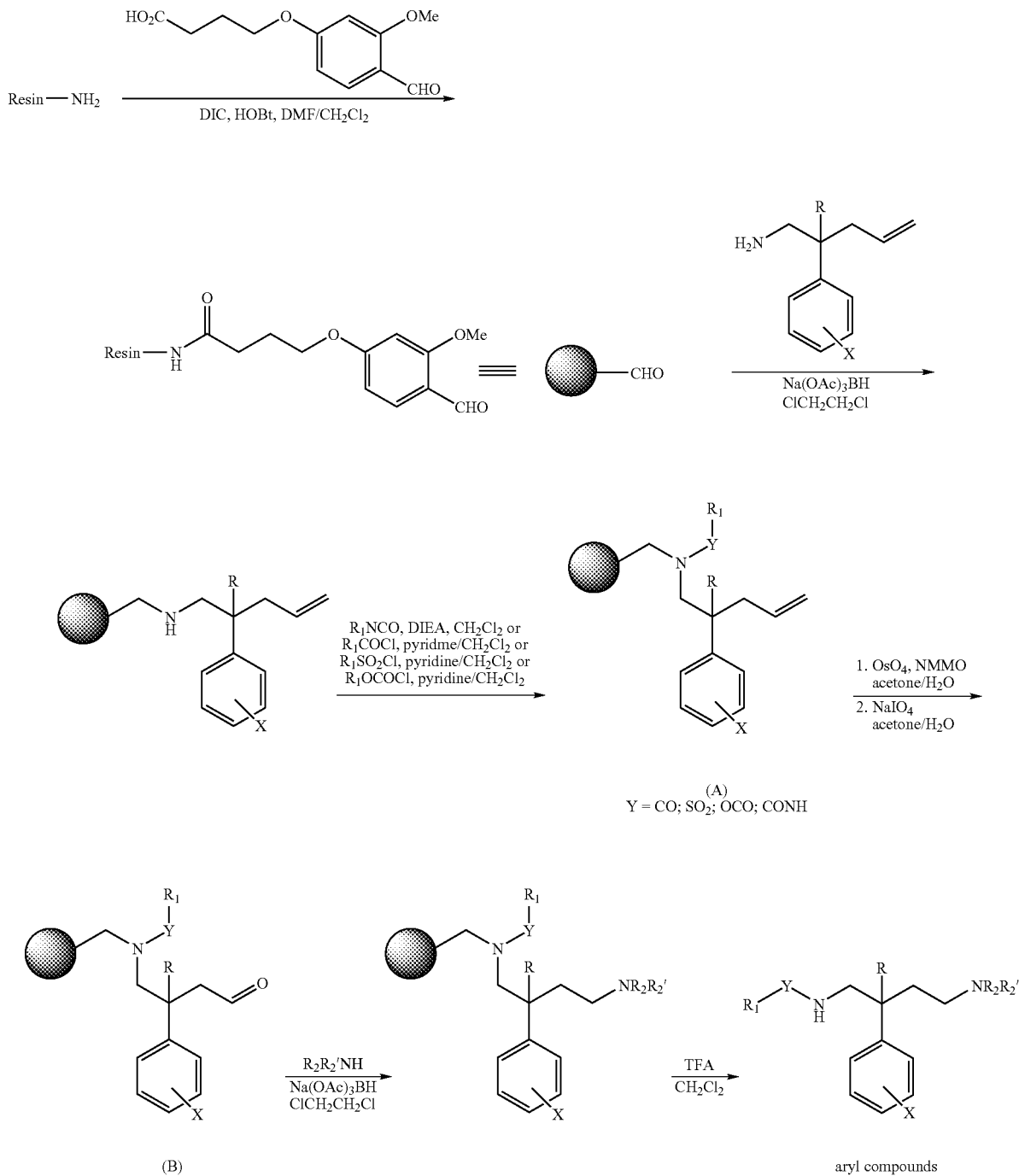

Intermediate A may be treated with $OsO_4/NMMO/NaIO_4$ to form the aldehyde intermediate B. Intermediate B is able to be converted to a secondary or tertiary amine via reductive amination using a primary or secondary amine and $Na(OAc)_3BH$. The product can be cleaved from the acid labile linker using $TFA/CH_2Cl_2$ to give the aryl compounds of the invention.

When X=I or Br, intermediate A may be converted to a biaryl compound via Suzuki coupling (A. Suzuki et al, *J. Amer. Chem. Soc.*, 111 (1989) 314). using an arylboronic acid as shown in Scheme 4. The Suzuki coupling product can be treated with $OsO_4/NMMO/NaIO_4$ to convert the terminal olefin group to an aldehyde group. The resulting aldehyde is able to be converted to a secondary or tertiary amine via reductive amination using a primary or secondary amine and $Na(OAc)_3BH$. The final reaction product can be cleaved from the acid labile linker using $TFA/CH_2Cl_2$ to give the biaryl compounds of the invention.

Scheme 4

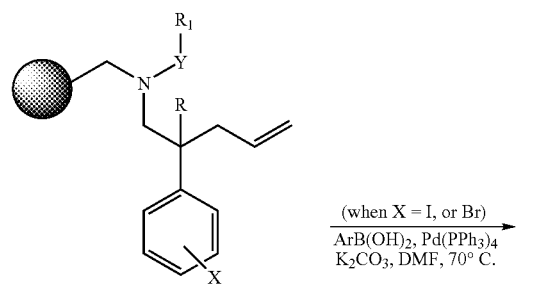

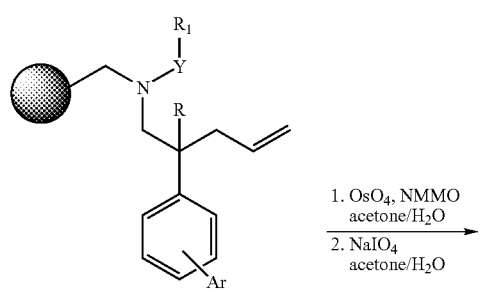

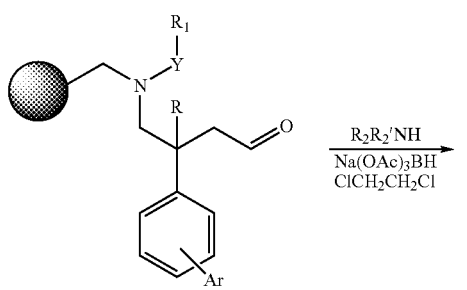

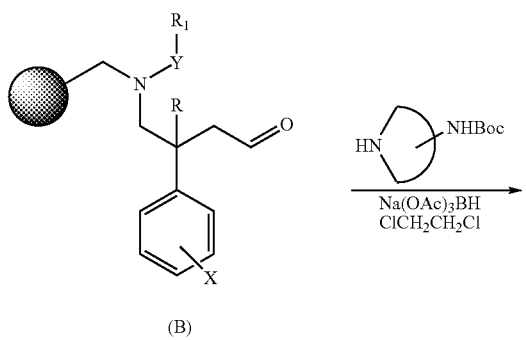

Scheme 5 outlines a general method for preparing compounds of Formula I that feature functionalized $R_1$ groups derived from the intermediate B of Scheme 3. Thus, reductive amination of the aldehyde intermediate B using a Boc-protected diamine, for example, 4N-tert-butyloxycarbonylaminopiperidine, forms a Boc-protected diamine compound. Treatment of the resin with TMSOTf and 2,6-lutidine effects clean removal of the Boc-protecting group with no cleavage of the compound from the acid labile linker (ref.: A. J. Zhang et al, *Tet. Lett.* (1998), 39, 7439–7442. The resulting amine can then be derivatized by reacting with an aryl or alkyl isocyanate, acid chloride sulfonyl chloride, or chloroformate to form a corresponding urea, amide, sulfonamide, or carbamate intermediate C, respectively. Intermediate C may be cleaved directly from the acid labile linker using TFA/CH$_2$Cl$_2$ to give an aryl compound of Formula I of the invention. Alternatively, intermediate C may be converted to a biaryl compound via Suzuki coupling using an arylboronic acid followed by treatment with TFA/CH$_2$Cl$_2$ to give a biaryl compound of Formula I of the invention.

Scheme 5

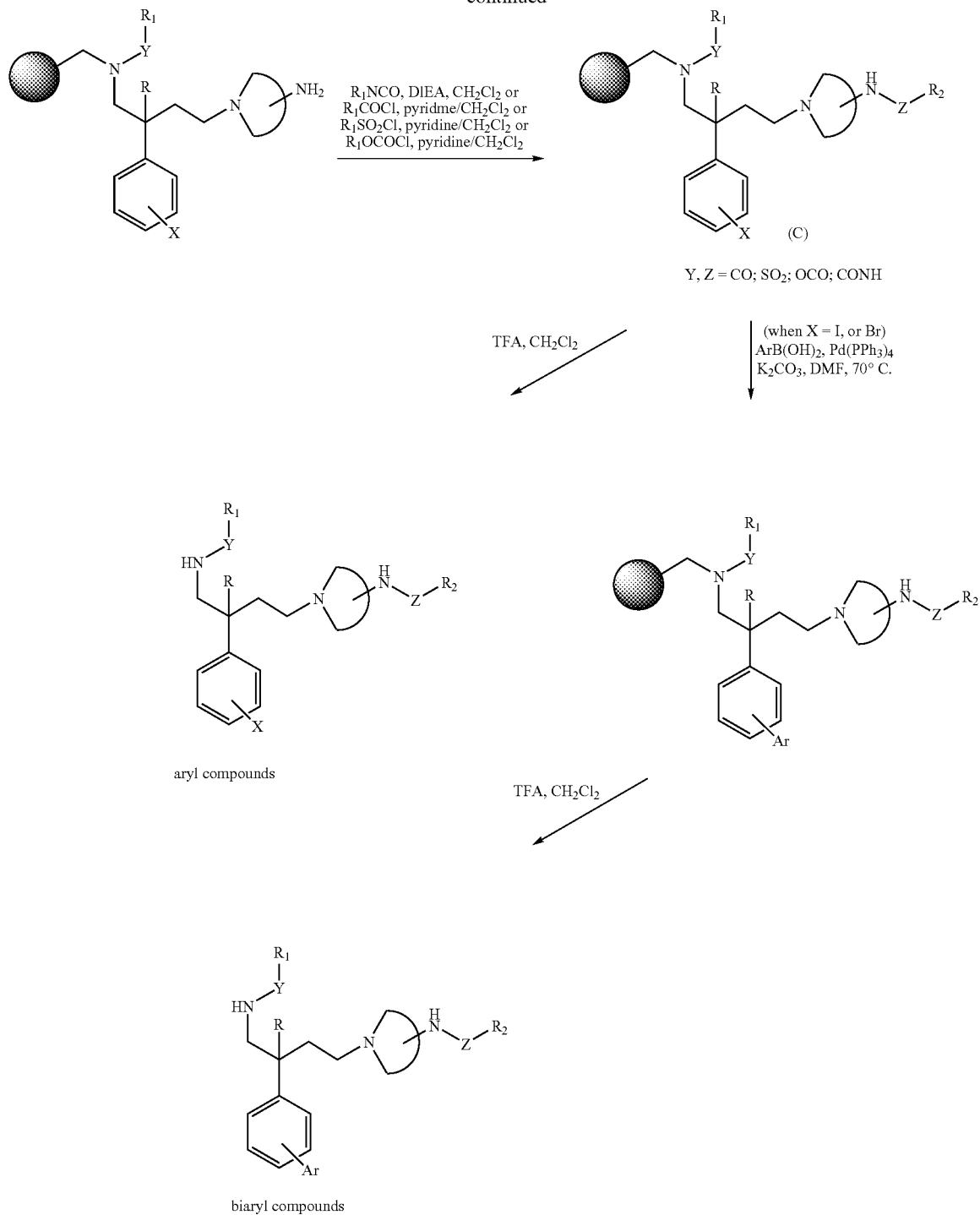

Scheme 6 outlines a general method for preparing compounds of Formula II of the invention using a novel solid phase synthesis. The synthesis commences with the coupling of a suitable linker, such as illustrated using an acid cleavable linker 4-(4-formyl-3-methoxy-phenoxy)-butyric acid to a suitable amino resin through amide bond formation. Reductive amination of the linker aldehyde with a primary amine forms a resin bound secondary amine. The secondary amine is then coupled with an acid chloride scaffold to form the amide intermediate D. Treatment of intermediate D with $OsO_4$/NMMO/$NaIO_4$ converts the terminal olefin group to an aldehyde group. The aldehyde is able to be converted to a secondary or tertiary amine via reductive amination using a primary or secondary amine and $Na(OAc)_3BH$. Cleavage from the acid labile linker using TFA/$CH_2Cl_2$ gives an aryl compound of the invention.

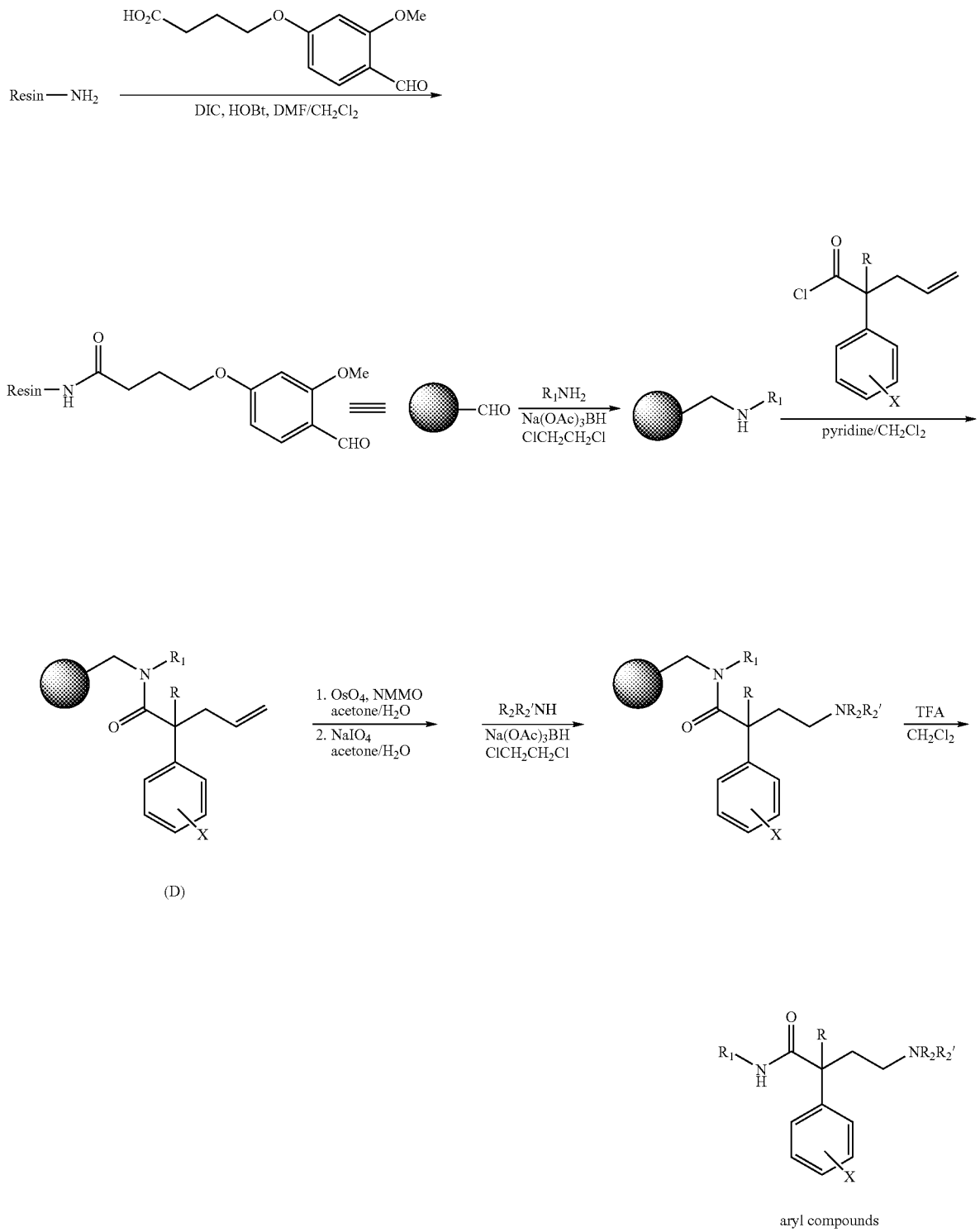

Alternatively, when X=I or Br, intermediate D may be treated with an aryl boronic acid via Suzuki coupling to form a biaryl compound as outlined in Scheme 7. Reaction of the biaryl compound with $OsO_4$/NMMO/$NaIO_4$ converts the terminal olefin group to an aldehyde group. The resulting aldehyde is able to be converted to a secondary or tertiary amine via reductive amination using a primary or secondary amine and $Na(OAc)_3BH$. Cleaved from the acid labile linker using TFA/$CH_2Cl_2$ affords a biaryl compound of the invention.

Scheme 7

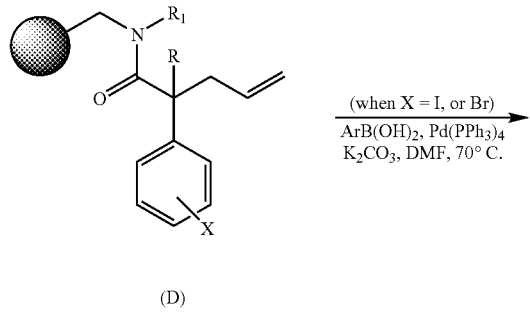

(D)

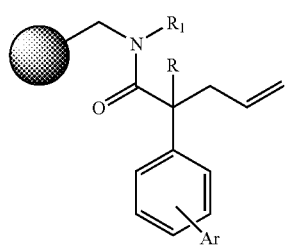

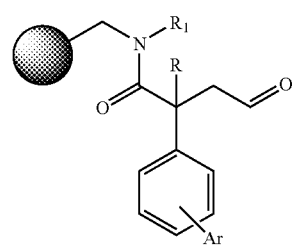

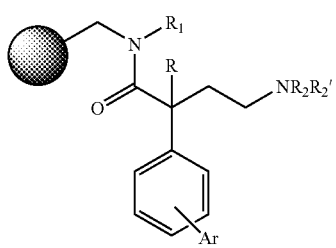

biaryl compounds

Scheme 8 illustrates a general solution phase method for preparing compounds of Formula II of the invention. Treatment of an acid chloride scaffold with an aniline gives the amide compound, which can be converted to the biaryl intermediate via Suzuki coupling. Oxidation of the olefin followed by reductive amination provides biaryl compounds of the invention.

Scheme 8

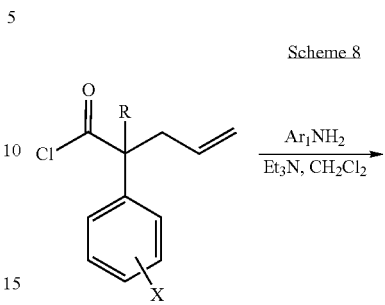

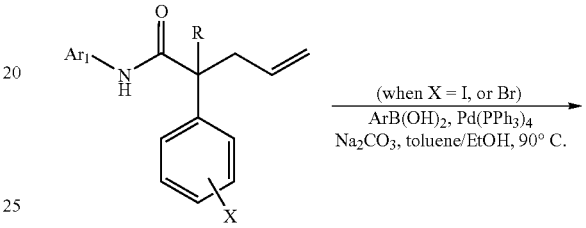

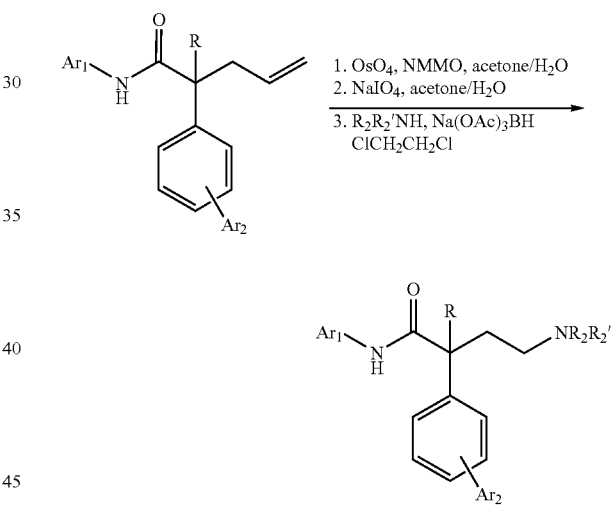

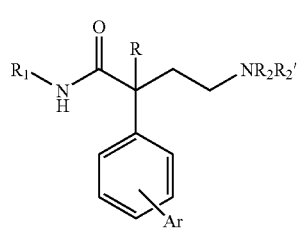

Scheme 9 outlines a method for preparing the cyclic urea (imidazolidinone) compounds of Formula I of the invention. The synthesis begins with the heating of an aryl isocyanate in t-BuOH to form the Boc-protected aniline. Treatment of the aniline with NaH and allyl iodide yields the Boc-protected N-allyl aniline. The olefin is then converted to an aldehyde via ozonolysis using $O_3$ followed by $Me_2S$. The resulting aldehyde is combined with a 5-amino-4-aryl-4-alkyl-but-1-ene synthon through reductive amination to form a secondary amine. The Boc-protecting group on the aniline nitrogen is removed using $TFA/CH_2Cl_2$ and the resulting diamine is treated with CDI in toluene at reflux to form the cyclic urea intermediate. The olefin group in the cyclic urea intermediate is converted to an aldehyde group via ozonolysis using $O_3$ followed by $Me_2S$. Reductive amination of the resulting aldehyde with an appropriate primary or secondary amine provides the cyclic urea aryl compound of Formula I of the invention. When X is an iodo or bromo group, reaction with arylboronic acids under Suzuki coupling conditions gives the cyclic urea biaryl compound of the invention.
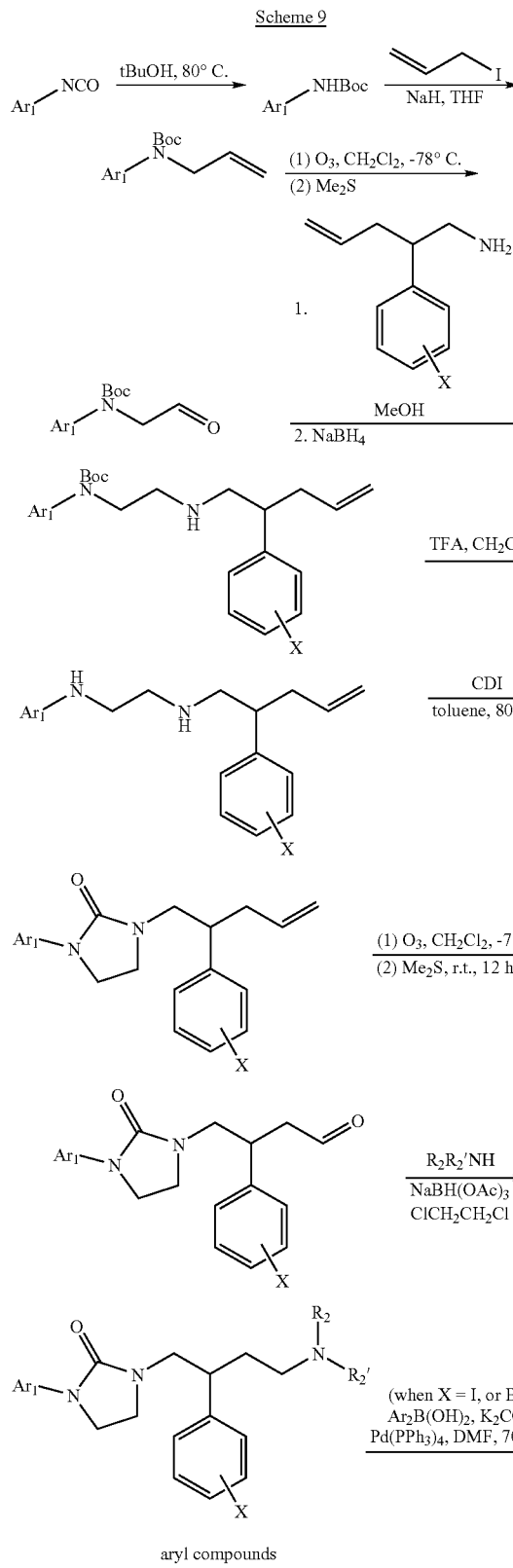
aryl compounds
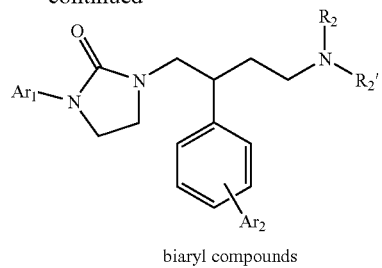
biaryl compounds
Scheme 10 outlines a method for preparing the series of carbamate compounds of Formula II of the invention.
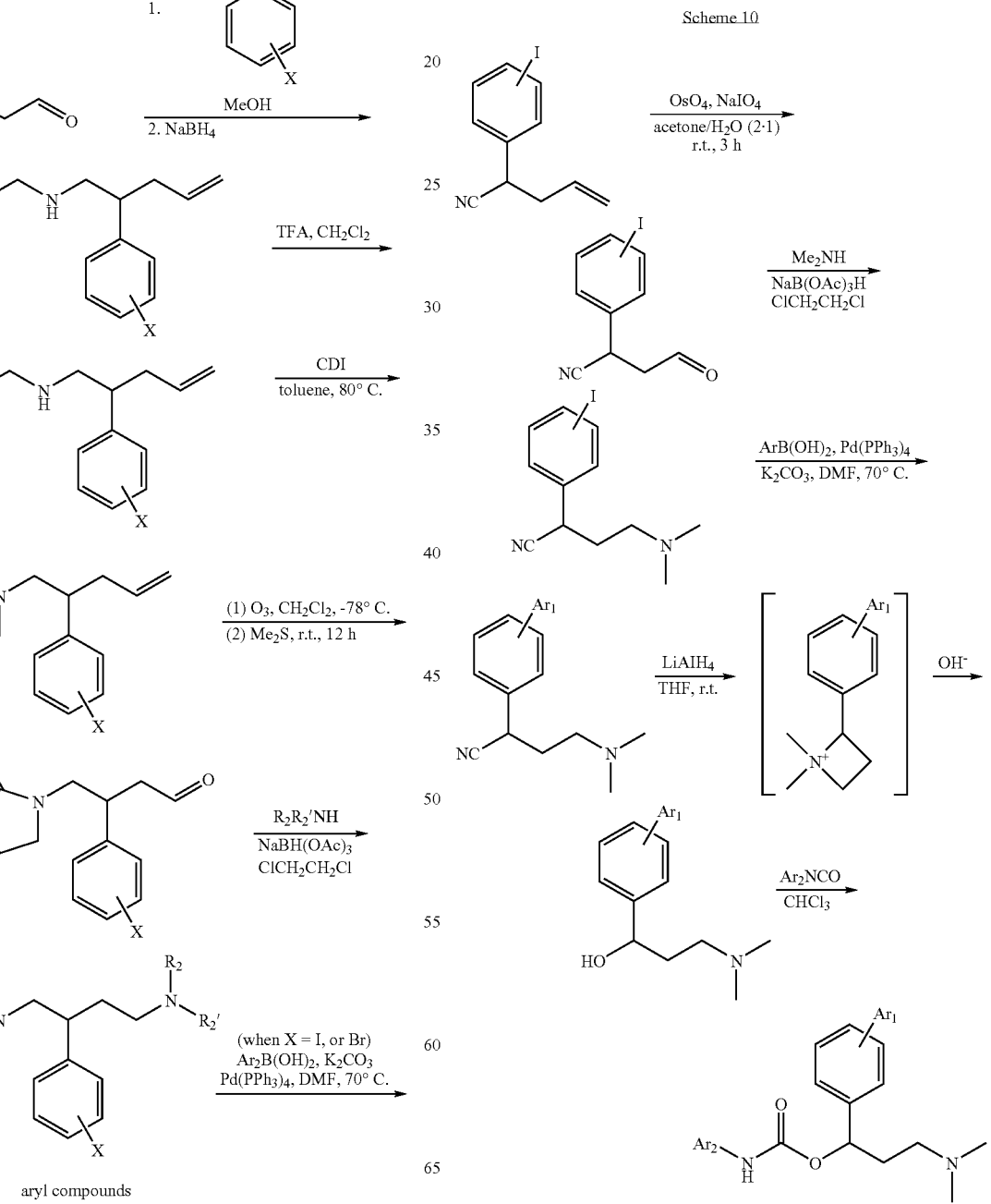

The synthesis starts with the oxidation of an appropriate iodophenylpentenenitrile to form an aldehyde using $OsO_4$/NMMO/$NaIO_4$. Reductive amination of the aldehyde with an appropriate secondary amine, such as dimethylamine, forms a tertiary amine. Suzuki coupling reaction is then performed to give the biaryl nitrile intermediate. Reduction of the nitrile intermediate using $LiAlH_4$ produced the alcohol product as shown in the scheme, presumably via an azetidinium cation intermediate. Treatment of the alcohol with an aryl isocyanate give the biaryl carbamate compound of Formula II of the invention.

The following Examples are provided for the purpose of further illustration only and are not intended to be limitations on the disclosed invention. Examples 1–19 illustrate the synthesis of scaffold intermediates.

EXAMPLE 1

(R,S)2-(4-Bromophenyl)-pent-4-enylamine (General Procedure)

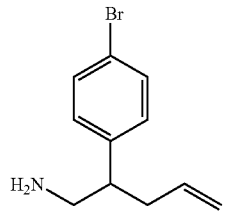

4-Bromophenylacetonitrile (10 g, 52.7 mmol, 1 eq) in THF (100 mL) was cooled to −78° C. under argon. LDA (2 M in THF, 29 mL, 58 mmol, 1.1 eq) was added and the reaction was warmed to 0° C. over 1 h. The reaction was re-cooled to −78° C. and allyl iodide (6.18 mL, 52.7 mmol, 1 eq) was added and the reaction stirred at −78° C. for a further 2 h. The reaction was diluted with EtOAc (150 mL) and washed with aqueous HCl (1 M, 100 mL), aqueous $Na_2S_2O_3$ (100 mL) and saturated aqueous NaCl (100 mL). The organic extracts were dried over anhydrous $Na_2SO_4$, filtered and concentrated by rotary evaporation to afford crude 1-cyano-1-(4-bromophenyl)-but-4-ene (10.5 g, ~44 mmol) as a yellow oil.

A solution of $LiAlH_4$ (1 M in THF, 123 mL, 123 mmol) in THF (140 mL) was cooled to 0° C. under Ar. $H_2SO_4$ (95%, 4 mL, 62.5 mmol) was added in a drop-wise fashion over 10 min. The icebath was removed and the mixture was stirred at room temperature for 2 h. A solution of crude 1-cyano-1-(4bromophenyl)-but-4-ene (10.5 g, ~44 mmol) in THF (60 mL) was added in a drop-wise fashion. The reaction was heated to reflux for 1 h, then cooled to room temperature and stirred for 16 h. The reaction was quenched by careful addition of $H_2O$ (4.67 mL, 260 mmol), NaOH (15% aqueous solution, 9.33 mL, 520 mmol ) and $H_2O$ (14 mL, 780 mmol ). The resulting slurry was diluted with EtOAc and stirred for a further 1 h, then filtered through a pad of celite 545®. The filtered salts were washed with EtOAc (4×50 mL) and the filtrate was concentrated by rotary evaporation to afford the title compound 1-amino-2-(4-bromophenyl)-pent-5-ene as a dark brown oil (10.36 g, 43.1 mmol, 88% over 2 steps): $^1$H NMR (300 MHz, $CDCl_3$): δ 7.50 (dd, 2H), 7.30 (d, 1H), 7.20 (d, 1H), 5.7 (m, 1H), 5.15 (m, 2H), 3.00 (m, 2H), 2.78 (m, 1H), 2.50 (m, 2H), 1.70 (br s, 2H).

EXAMPLES 2–15 are listed in the following table:

| EXAMPLE | STRUCTURE | $^1$H-NMR (300 MHz, $CDCl_3$) |
|---|---|---|
| 2 | 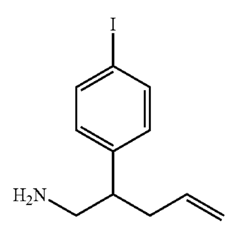 | 7.75 (d, 2H), 7.05 (d, 2H), 5.75 (m, 1H), 5.11 (m, 2H), 3.08 (m, 1H), 2.95 (m, 1H), 2.79 (m, 1H), 2.46 (m, 2H), 2.04 (br.s, 2H). |
| 3 | 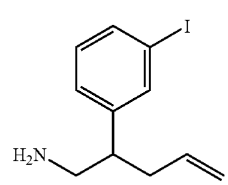 | 7.66 (m, 2H), 7.38 (m, 1H), 7.18 (m, 1H), 5.77 (m, 1H), 5.12 (m, 2H), 3.02 (m, 2H), 2.75 (m, 1H), 2.49 (m, 2H), 1.56 (br.s, 2H). |
| 4 | 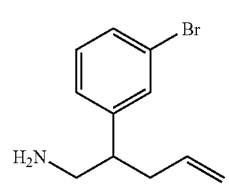 | 7.30 (m, 4H), 5.78 (m, 1H), 5.10 (m, 2H), 3.09 (m, 1H), 2.95 (m, 1H), 2.80 (m, 1H), 2.49 (m, 2H), 2.80 (m, 1H), 2.49 (m, 2H), 1.80 (br.s, 2H). |

-continued
| EXAMPLE | STRUCTURE | ¹H-NMR (300 MHz, CDCl₃) |
|---|---|---|
| 5 | 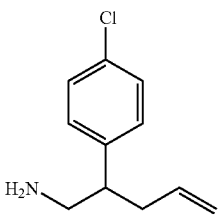 | 7.23 (d, 2H), 7.11 (d, 2H), 5.61 (m, 1H), 4.98 (m, 2H), 2.90 (m, 2H), 2.70 (m, 1H), 2.33 (m, 2H), 1.82 (br.s, 2H). |
| 6 | 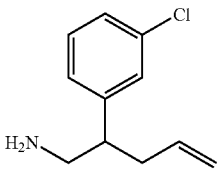 | 7.33 (m, 3H), 7.17 (m, 1H), 5.77 (m, 1H), 5.11 (m, 2H), 3.08 (m, 1H), 2.96 (m, 1H), 2.79 (m, 1H), 2.49 (m, 2H), 1.43 (br.s, 2H). |
| 7 | 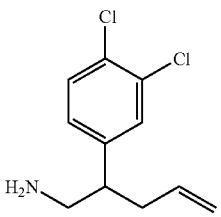 | 7.51 (dd, 1H), 7.39 (dd, 1H), 7.15 (dd, 1H), 5.75 (m, 1H), 5.11 (m, 2H), 3.08 (m, 1H), 2.95 (m, 1H), 2.78 (m, 1H), 2.48 (m, 2H), 1.68 (br.s, 2H). |
| 8 | 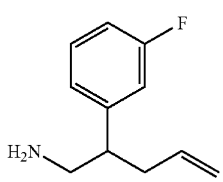 | 7.38 (m, 1H), 7.05 (m, 3H), 5.77 (m, 1H), 5.11 (m, 2H), 3.02 (m, 2H), 2.81 (m, 1H), 2.48 (m, 2H), 1.50 (br.s, 2H). |
| 9 | 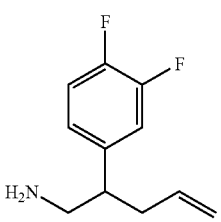 | 7.14 (m, 3H), 5.72 (m, 1H), 5.08 (m, 2H), 3.06 (dd, 1H), 2.92 (dd, 1H), 2.78 (m, 1H), 2.46 (m, 2H), 1.70 (br.s, 2H). |
| 10 | 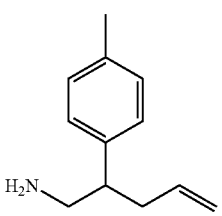 | 7.22 (dd, 4H), 5.80 (m, 1H), 5.11 (m, 2H), 3.07 (m, 1H), 2.95 (m, 1H), 2.79 (m, 1H), 2.50 (m, 2H), 2.45 (s, 3H), 1.58 (br.s, 2H). |
| 11 | 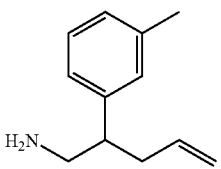 | 7.32 (m, 1H), 7.12 (m, 3H), 5.81 (m, 1H), 5.12 (m, 2H), 3.06 (m, 1H), 2.96 (m, 1H), 2.77 (m, 1H), 2.48 (m, 2H), 2.47 (s, 3H), 1.62 (br.s, 2H). |

| EXAMPLE | STRUCTURE | $^1$H-NMR (300 MHz, CDCl$_3$) |
|---|---|---|
| 12 | 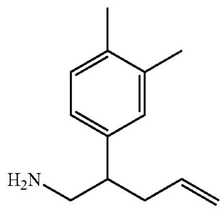 | 7.21 (m, 1H), 7.06 (m, 2H), 5.81 (m, 1H), 5.10 (m, 2H), 3.07 (m, 1H), 2.94 (m, 1H), 2.76 (m, 1H), 2.48 (m, 2H), 2.36 (s, 3H), 2.34 (s, 3H), 1.73 (br.s, 2H). |
| 13 | 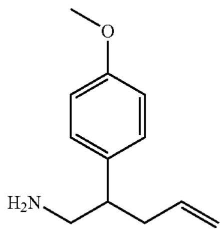 | 7.22 (d, 2H), 6.98 (d, 2H), 5.8 (m, 1H), 5.10 (m, 2H), 3.89 (s, 3H), 2.98 (m, 2H), 2.76 (m, 1H), 2.48 (m, 2H), 1.43 (br.s, 2H). |
| 14 | 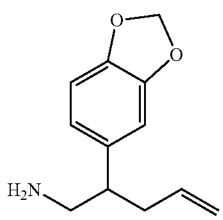 | 6.80 (m, 3H), 6.20 (s, 2H), 5.79 (m, 1H), 5.08 (m, 2H), 3.02 (m, 1H), 2.88 (m, 1H), 2.74 (m, 1H), 2.41 (m, 2H), 1.88 (br.s, 2H). |
| 15 | 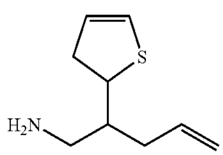 | 7.29 (m, 1H), 7.08 (m, 1H), 6.96 (m, 1H), 5.84 (m, 1H), 5.16 (m, 2H), 3.16 (m, 1H), 3.12 (m, 2H), 2.57 (m, 2H), 1.66 (br.s, 2H). |

EXAMPLE 16

2-(3,4-Dichlorophenyl)-2-mentyl-pent-4-enylamine

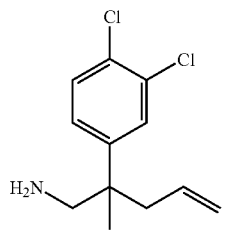

3,4-Dichlorophenylacetonitrile (5 g, 26.87 mmol, 1 eq) in THF (50 mL) was cooled to −78° C. under Ar. LDA (2 M in THF, 16.1 mL, 32.2 mmol, 1.2 eq) was added and the reaction was warmed to 0° C. over 1 h. The reaction was re-cooled to −78° C. and allyl iodide (2.67 mL, 26.87 mmol, 1 eq) was added then the reaction was stirred at −78° C. for a further 2 h. The reaction was diluted with EtOAc (150 mL) and washed with aqueous HCl (1 M, 100 mL), saturated aqueous Na$_2$S$_2$O$_3$ (100 mL) and saturated aqueous NaCl (100 mL). The organic extracts were dried over Na$_2$SO$_4$, filtered and concentrated by rotary evaporation to afford 2-(3,4-dichlorophenyl)-pent-4-ene-nitrile (6.3 g, ~28 mmol) as a yellow oil.

A 1 g (4.4 mmol) portion of 2-(3,4-dichlorophenyl)-pent-4-ene-nitrile in THF is (25 mL) at −78° C. under Ar was treated with LDA (2M in THF, 2.7 mL, 5.4 mmol, 1.2 eq). The reaction was warmed to 0° C. for 1 h, then recooled to −78° C. and methyl iodide (0.28 mL, 4.4 mmol, 1.0 eq) was added. The reaction was stirred at −78 ° C. for 1 h, then diluted with EtOAc and washed with aqueous HCl (1 M, 25 mL), aqueous Na$_2$S$_2$O$_3$ (25 mL) and saturated aqueous NaCl (25 mL). The organic extracts were dried over sodium sulfate, filtered and concentrated by rotary evaporation to afford 2-(3,4-dichlorophenyl)-2-mentyl-pent-4-ene-nitrile (1.04 g, 4.39 mmol, 99.8%) as a yellow oil. $^1$H NMR (300 MHz, CDCl$_3$): δ 7.60 (dd, 1H), 7.35 (m, 2H), 5.77 (m, 1H), 5.28 (m, 2H), 2.72 (m, 2H), 1.8 (s, 3H).

A solution of LiAlH$_4$ (1 M in THF, 18.65 mL, 18.65 mmol,) in THF (25 mL) was cooled to 0° C. under Ar. H$_2$SO$_4$ (95%, 0.51 mL, 9.38 mmol) was added in a dropwise fashion over 10 min. The mixture was stirred at room temperature for 2 h, then a solution of 2-(3,4-dichlorophenyl)-2-mentyl-pent-4-ene-nitrile (1.28 g, 6.22 mmol) in THF (10 mL) was added in a dropwise fashion. The reaction was heated to reflux for 1 h, then cooled to room temperature and stirred for 16 h. The reaction was quenched by careful addition of H$_2$O (0.71 mL, 12.8 mmol), NaOH (15% aqueous solution, 1.34 mL, 25.6 mmol) and H$_2$O (2.05 mL, 38.4 mmol). The resulting slurry was stirred for a further 1 h and then filtered through a pad of celite 545®. The filtered salts were washed with EtOAc (4×20 mL) and the combined organic filtrate was concentrated by rotary evaporation to afford the title compound 1-amino-2-(3,4-dichlorophenyl)-2mentyl-pent-4enylamine (1.22g, 4.99 mmol, 80.2%) as a dark brown oil. $^1$H NMR (300 MHz, CDCl$_3$): δ 7.50 (m, 1H), 7.25 (m, 2H), 5.63 (m, 1H), 5.10 (m, 2H), 2.94 (dd, 2H), 2.54 (m, 2H), 2.03 (br s, NH$_2$), 1.4 (s, 3H).

EXAMPLE 17

(R,S)-2-(3,4-Dichloro-phenyl)-pent-4-enoyl Chloride

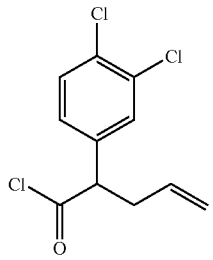

A solution of (3,4-dichlorophenyl)acetic acid (16.12 g, 78.5 mmol) in MeOH (500 mL) was bubbled with HCl gas for 5 min. The mixture was stirred at room temperature for 1 h. The solvent was removed by rotary evaporation and the resulting residue was dissolved in EtOAc (400 mL) and washed with saturated aqueous NaHCO$_3$ (200 mL) and saturated aqueous NaCl (200 mL). The organic extracts were dried over sodium sulfate, filtered and concentrated by rotary evaporation to give (3,4-dichlorophenyl)acetic acid methyl ester (16.22 g, 74.1 mmol, 95%). $^1$H NMR (300 MHz, CDCl$_3$): δ 7.50 (m, 2H), 7.23 (dd, 1H), 3.81 (s, 3H), 3.69 (s, 2H).

(3,4-Dichloro-phenyl)-acetic acid methyl ester (5 g, 22.8 mmol) in THF (50 mL) was cooled to −78° C. under Ar. LDA (2M in THF, 13.7 mL, 27.4 mmol, 1.2 eq) was added in a dropwise fashion and the reaction was warmed to 0° C. for 1 h. The reaction was cooled to −78° C. and allyl iodide (2.1 mL, 22.8 mmol, 1 eq) was added. The reaction was stirred at −78° C. for 4 h and then diluted with EtOAc (200 mL), washed with saturated aqueous Na$_2$S$_2$O$_3$ (100 mL) and saturated aqueous NaCl (100 mL). The combined organic extracts were dried over Na$_2$SO$_4$, filtered and concentrated by rotary evaporation to give crude (R,S)-2-(3,4-dichloro-phenyl)-pent-4-enoic acid methyl ester (6.0 g, ~22 mmol, 100%) as a brown oil. $^1$H NMR (300 MHz, CDCl$_3$): δ 7.51 (m, 2H), 7.26 (dd, 1H), 5.78 (m, 1H), 5.15 (m, 2H), 3.79 (s, 1H), 3.71 (m, 1H), 2.90 (m, 1H), 2.60 (m, 1H).

Lithium hydroxide (1.66 g, 69.3 mmol, 3 eq) was dissolved in H$_2$O (50 mL) and added to a solution of (R,S)-2-(3,4-dichloro-phenyl)-pent-4-enoic acid methyl ester (6 g, 22 mmol) dissolved in THF/MeOH (1.5:1 v:v, 250 mL) and the resulting mixture was stirred at room temperature for 3 h. The solvent was removed by rotary evaporation and the residue was partitioned between EtOAc and H$_2$O. The aqueous layer was acidified to pH 3 with aqueous 6N HCl and extracted with EtOAc (2×100 mL). The combined organic extracts were washed with saturated aqueous NaCl (100 mL) and concentrated by rotary evaporation to give (R,S)-2-(3,4-dichloro-phenyl)-pent-4-enoic acid as a brown solid. $^1$H NMR (300 MHz, CDCl$_3$): δ 7.52 (m, 2H), 7.28 (dd, 1H), 5.79 (m, 1H), 5.17 (m, 2H), 3.73 (t, 1H), 2.91 (m, 1H), 2.62 (m, 1H).

(R,S)-2-(3,4-Dichloro-phenyl)-pent-4-enoic acid (2.5 g, 10.24 mmol, 1 eq) was dissolved in SOCl$_2$ (10 mL). The reaction mixture was heated to reflux for 1 h and then the SOCl$_2$ was removed by rotary evaporation. The residue was co-evaporated from toluene (3×5 mL) and then dried under high vacuum for 1 h. It was redissolved in toluene (1 mL) and concentrated by rotary evaporation and then dried under high vacuum for 4 h to give the title compound (R,S)-2-(3,4-dichloro-phenyl)-pent-4-enoyl chloride (2.69 g, 10.2 mmol, ~100%). The acid chloride was used directly in the solid phase synthesis reactions.

EXAMPLES 18–19 are listed in the following table:

| EXAMPLE | STRUCTURE | $^1$H-NMR (300 MHz, CDCl$_3$) |
|---|---|---|
| 18 | 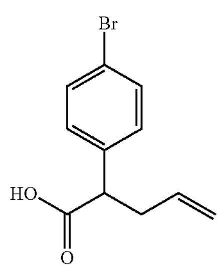 | 7.58 (d, 2H), 7.32 (d, 2H), 5.81 (m, 1H), 5.16 (m, 2H), 3.73 (dd, 1H), 2.90 (m, 1H), 2.63 (m, 1H). |
| 19 | 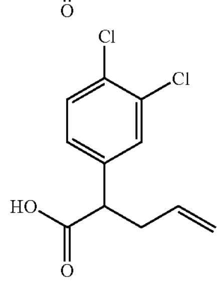 | 7.52 (m, 2H), 7.28 (dd, 1H), 5.79 (m, 1H), 5.17 (m, 2H), 3.73 (t, 1H), 2.91 (m, 1H), 2.62 (m, 1H). |

EXAMPLES 20–33; Illustrate the Synthesis of MCH Active Compounds

EXAMPLE 20

(R,S)-N-[4-Cyclopentylamino-2-(3,4-dichloro-phenyl)-butyl]-3,5-bis-trifluoromethyl-benzamide

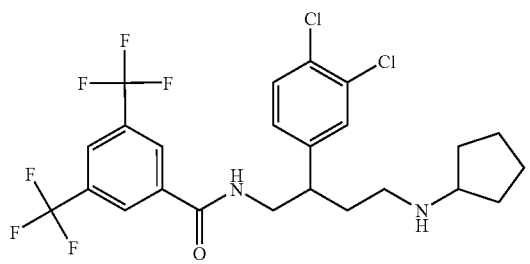

A 1 liter bottle was charged with Argo-Gel-NH$_2$ (30 g, 12 mmol, supplied by Argonaut Technologies, Incorporated, California), CH$_2$Cl$_2$ (200 mL) and DMF (50 mL). A premixed (30 min) solution of 4-(4-formyl-3-methoxy-phenoxy)-butyric acid linker (8.577 g, 36 mmol, 3 eq), HOBt (4.865 g, 36 mmol, 3 eq) and DIC (11.54 mL, 72 mmol, 6 eq) in CH$_2$Cl$_2$ (250 mL) was added to the resin suspension and the mixture was shaken at room temperature for 16 h. The resin was transferred to 2 large shaking vessels, the solution was drained and the resin was washed with DMF (3×), MeOH (3×) and CH$_2$Cl$_2$ (3×) and dried under high vacuum to give the acid cleavable linker containing 4-(4-formyl-3-methoxy-phenoxy)-butyramide resin.

A 100 mg (0.04 mmol) portion of the resin was suspended in ClCH$_2$CH$_2$Cl (1 mL) and a solution of 1-amino-2-(3,4-dichloro-phenyl)-pent-5-ene (0.05 g, 0.2 mmol, 5 eq) in ClCH$_2$CH$_2$Cl (1 mL) was added. The resin was shaken for 20 min at room temperature and then Na(OAc)$_3$BH (0.045 g, 0.2 mmol, 5 eq) was added and the reaction was shaken at room temperature for 16 h. The solution was filtered and the resin was washed with MeOH (1×), DMF (3×), MeOH (3×) and CH$_2$Cl$_2$ (3×). An aliquot of the resin tested positive with chloranil and negative with 2,4-dinitrophenylhydrazine.

The resin was suspended in pyridine (1.5 mL) and 3,5-bis(trifluoromethyl)-benzoyl chloride (1.5 mL of a 1 M solution in CH$_2$Cl$_2$, 1.5 mmol) was added. The resin was shaken at room temperature for 16 h, the solution filtered and the resin washed with CH$_2$Cl$_2$ (3×), DMF (3×), MeOH (2×) and CH$_2$Cl$_2$ (3×). An aliquot of the resin gave a negative chloranil test.

The resin was shaken at room temperature for 14 h with a solution of OsO$_4$ (4% in H$_2$O, 0.052 mL, 0.008 mmol, 0.2 eq) and NMMO (0.05 g, 0.4 mmol, 10 eq) in acetone-H$_2$O (1:1, 3 mL) at room temperature for 14 h. The solution was filtered and the resin was washed with H$_2$O (2×), acetone (2×), pyridine (1×, shake for 30 min), MeOH (2×) and CH$_2$Cl$_2$ (3×). A solution of NaIO$_4$ (0.085 g, 0.4 mmol, 10 eq) in acetone-H$_2$O (1:1, 3 mL) was added and the mixture shaken for 2 h. The solution was filtered and the resin was washed with H$_2$O (2×) and acetone (1×). The resin was treated with a fresh solution of NaIO$_4$ (0.085 g, 0.4 mmol, 10 eq) in acetone-H$_2$O (1:1, 3 mL) and shaken for a further 2 h. The solution was filtered and the resin was washed with H$_2$O (3×), acetone (1×), MeOH (2×) and CH$_2$Cl$_2$ (3×).

The resin was shaken with a solution of cyclopentylamine (0.024 g, 0.2 mmol, 5 eq) in ClCH$_2$CH$_2$Cl (1.5 mL) for 30 min. Na(OAc)$_3$BH (0.05 g, 0.2 mmol, 5 eq) was added and the mixture shaken at room temperature for 14 h. The solution was filtered and the resin washed with MeOH (2×), DMF (3×), MeOH (3×) and CH$_2$Cl$_2$ (3×). An aliquot of the resin gave a positive chloranil test. The resin was treated with a solution of TFA (25% in CH$_2$Cl$_2$, 3 mL) and shaken for 2 h at room temperature, filtered off and the filtrate was purified by Gilson 215 HPLC (10–90% acetonitrile/water) to yield the title compound (0.0050 g, 27%), MS (ESI): 541.1 (M+1), 543.1 (M+3).

EXAMPLE 21

(R,S)-3,4-Dichloro-N-[4-cyclopentylamino-2-(3,4-dichloro-phenyl)-butyl]-benzenesulfonamide

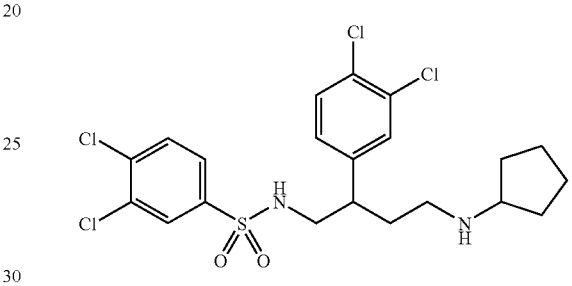

A 100 mg (0.04 mmol) portion of the 4-(4-formyl-3-methoxy-phenoxy)-butyramide resin (see step 1 of EXAMPLE 20) was suspended in ClCH$_2$CH$_2$Cl (1 mL) and a solution of 1-amino-2-(3,4-dichloro-phenyl)-pent-5-ene (0.05 g, 0.2 mmol, 5 eq) in ClCH$_2$CH$_2$Cl (1 mL) was added. The resin was shaken for 20 min at room temperature and then Na(OAc)$_3$BH (0.045 g, 0.2 mmol, 5 eq) was added. The reaction was shaken at room temperature for 16 h. The solution was filtered and the resin was washed with MeOH (1×), DMF (3×), MeOH (3×) and CH$_2$Cl$_2$ (3×). An aliquot of the resin tested positive with chloranil and negative with 2,4-dinitrophenylhydrazine.

The resin was suspended in pyridine (1.5 mL) and 3,4-dichlorobenzenesulfonyl chloride (1.5 mL of a 1 M solution in CH$_2$Cl$_2$, 1.5 mmol) was added. The resin was shaken at room temperature for 16 h, the solution filtered and the resin washed with CH$_2$Cl$_2$ (3×), DMF (3×), MeOH (2×) and CH$_2$Cl$_2$ (3×). An aliquot of the resin gave a negative chloranil test.

The resin was shaken at room temperature for 14 h with a solution of OsO$_4$ (4% in H$_2$O, 0.052 mL, 0.008 mmol, 0.2 eq) and NMMO (0.05 g, 0.4 mmol, 10 eq) in acetone-H$_2$O (1:1, 3 mL) at room temperature for 14 h. The solution was filtered and the resin was washed with H$_2$O (2×), acetone (2×), pyridine (1×, shake for 30 min), MeOH (2×) and CH$_2$Cl$_2$ (3×). A solution of NaIO$_4$ (0.085 g, 0.4 mmol, 10 eq) in acetone-H$_2$O (1:1, 3 mL) was added and the mixture shaken for 2 h. The solution was filtered and the resin was washed with H$_2$O (2×), acetone (1×). The resin was treated with a fresh solution of NaIO$_4$ (0.085 g, 0.4 mmol, 10 eq) in acetone-H$_2$O (1:1, 3 mL) and shaken for a further 2 h. The solution was filtered and the resin was washed with H$_2$O (3×), acetone (1×), MeOH (2×) and CH$_2$Cl$_2$ (3×).

The resin was shaken with a solution of cyclopentylamine (0.024 g, 0.2 mmol, 5 eq) in ClCH$_2$CH$_2$Cl (1.5 mL) for 30 min. Na(OAc)$_3$BH (0.05g, 0.2 mmol, 5 eq) was added and the mixture shaken at room temperature for 14 h. The solution was filtered and the resin washed with MeOH (2×), DMF (3×), MeOH (3×) and CH$_2$Cl$_2$ (3×). An aliquot of the resin gave a positive chloranil test. The resin was treated with a solution of TFA (TFA, 25% in CH$_2$Cl$_2$, 3 mL) and shaken for 2 h at room temperature, filtered off and the filtrate was purified by Gilson 215 HPLC (10–90% acetonitrile/water) to yield the title compound (0.00102 g, 47%). MS (ESI): 509.1 (M+1), 511.0 (M+3), 513.0 (M+5).

EXAMPLE 22

(R,S)-[3-Cyclobutylamino-2-(3,4-dichloro-phenyl)-propyl]-3-(4-fluoro-3-nitro-phenyl)-urea

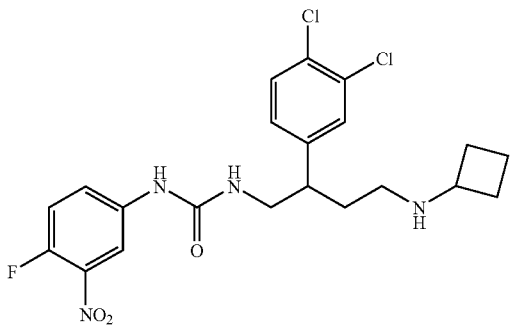

A 100 mg (0.04 mmol) portion of the 4-(4-formyl-3-methoxy-phenoxy)-butyramide resin (see step 1 of EXAMPLE 20) was suspended in ClCH$_2$CH$_2$Cl (1 mL) and a solution of 1-amino-2-(3,4-dichloro-phenyl)-pent-5-ene (0.047 g, 0.2 mmol, 5 eq) in ClCH$_2$CH$_2$Cl (1 mL) was added. The resin was shaken for 20 min at room temperature and then Na(OAc)$_3$BH (0.045 g, 0.2 mmol, 5 eq) was added. The reaction was shaken at room temperature for 16 h. The solution was filtered and the resin was washed with MeOH (1×), DMF (3×), MeOH (3×) and CH$_2$Cl$_2$ (3×). An aliquot of the resin tested positive with chloranil and negative with 2,4-dinitrophenylhydrazine.

The resin was suspended in CH$_2$Cl$_2$ (3.0 mL) and DIEA (0.035 mL, 5 eq) was added, followed by 3-nitro-4-fluorophenyl isocyanate (0.217 mL, 1.5 mmol). The mixture was shaken at room temperature for 16 h, the solution filtered and the resin washed with CH$_2$Cl$_2$ (3×), DMF (3×), MeOH (2×) and CH$_2$Cl$_2$ (3×). An aliquot of the resin gave a negative chloranil test.

The resin was shaken at room temperature for 14 h with a solution of OsO$_4$ (4% in H$_2$O, 0.052 mL, 0.008 mmol, 0.2 eq) and NMMO (0.05 g, 0.4 mmol, 10 eq) in acetone-H$_2$O (1:1, 3 mL) at room temperature for 14 h. The solution was filtered and the resin was washed with H$_2$O (2×), acetone (2×), pyridine (1×, shake for 30 min), MeOH (2×) and CH$_2$Cl$_2$ (3×). A solution of NaIO$_4$ (0.085 g, 0.4 mmol, 10 eq) in acetone-H$_2$O (1:1, 3 mL) was added and the mixture shaken for 2 h. The solution was filtered and the resin was washed with H$_2$O (2×), acetone (1×). The resin was treated with a fresh solution of NaIO$_4$ (0.085 g, 0.4 mmol, 10 eq) in acetone-H$_2$O (1:1, 3 mL) and shaken for a further 2 h. The solution was filtered and the resin was washed with H$_2$O (3×), acetone (1×), MeOH (2×) and CH$_2$Cl$_2$ (3×).

The resin was shaken with a solution of cyclobutylamine hydrochloride (0.022 g, 0.2 mmol, 5 eq) and triethylamine (0.03 mL, 0.2 mmol) in ClCH$_2$CH$_2$Cl (1.5 mL) for 30 min. Na(OAc)$_3$BH (0.05 g, 0.2 mmol, 5 eq) was added and the mixture shaken at room temperature for 14 h. The solution was filtered and the resin washed with MeOH (2×), DMF (3×), MeOH (3×) and CH$_2$Cl$_2$ (3×). An aliquot of the resin gave a positive chloranil test. The resin was treated with a solution of TFA (25% in CH$_2$Cl$_2$, 3 mL) and shaken for 2 h at room temperature, filtered off and the filtrate was purified by Gilson 215 HPLC (10–90% acetonitrile/water) to yield the title compound (0.0062 g, 33%). MS (ESI): 469.0 (M+1), 471.0 (M+3).

EXAMPLE 23

(R,S)-1-[2-(3'-Cyano-biphenyl-4-yl)-4-cyclopentylamino-butyl]-3-(3,5-dichloro-phenyl)-urea

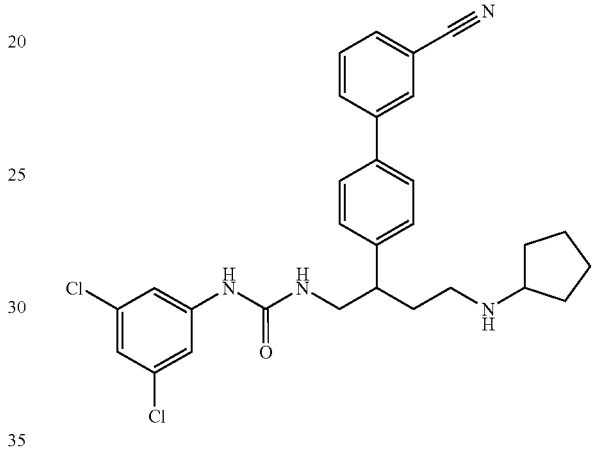

A 100 mg (0.04 mmol) portion of the 4-(4-formyl-3-methoxy-phenoxy) butyramide resin (see step 1 of EXAMPLE 20) was suspended in ClCH$_2$CH$_2$Cl (1 mL) and a solution of 1-amino-2-(4-bromophenyl)-pent-5-ene (0.048 g, 0.2 mmol, 5 eq) in ClCH$_2$CH$_2$Cl (1 mL) was added. The resin was shaken for 20 min at room temperature and then Na(OAc)$_3$BH (0.045 g, 0.2 mmol, 5 eq) was added. The reaction was shaken at room temperature for 16 h. The solution was filtered and the resin was washed with MeOH (1×), DMF (3×), MeOH (3×) and CH$_2$Cl$_2$ (3×). An aliquot of the resin tested positive with chloranil and negative with 2,4-dinitrophenylhydrazine.

The resin was suspended in CH$_2$Cl$_2$ (3.0 mL) and DIEA (0.035 mL, 0.2 mmol, 5 eq) was added, followed by 3,5-dichloro-phenyl isocyanate (0.283 g, 1.5 mmol, to give a 0.5M solution). The mixture was shaken at room temperature for 16 h, the solution filtered and the resin washed with CH$_2$Cl$_2$ (3×), DMF (3×), MeOH (2×) and CH$_2$Cl$_2$ (3×). An aliquot of the resin gave a negative chloranil test.

The resin was mixed with 3-cyanophenylboronic acid (0.024 g, 0.16 mmol, 4 eq), K$_2$CO$_3$ (0.028 g, 0.2 mmol, 5 eq) and Pd(PPh$_3$)$_4$ (0.009 g, 0.008 mmol, 0.2 eq). DMF (2 mL, degassed with Ar) was added and the mixture was heated to 70° C. for 16 h. The solution was filtered and the resin washed with DMF (4×), H$_2$O (4×), MeOH (3×) and CH$_2$Cl$_2$ (4×).

The resin was shaken at room temperature for 14 h with a solution of OsO$_4$ (4% in H$_2$O, 0.052 mL, 0.008 mmol, 0.2 eq) and NMMO (0.05 g, 0.4 mmol, 10 eq) in acetone-H$_2$O (1:1, 3 mL) at room temperature for 14 h. The solution was filtered and the resin was washed with H$_2$O (2×), acetone (2×), pyridine (1×, shake for 30 min), MeOH (2×) and CH$_2$Cl$_2$ (3×). A solution of NaIO$_4$ (0.085 g, 0.4 mmol, 10 eq) in acetone-H$_2$O (1:1, 3 mL) was added and the mixture shaken for 2 h. The solution was filtered and the resin was washed with H$_2$O (2×), acetone (1×). The resin was treated with a fresh solution of NaIO$_4$ (0.085 g, 0.4 mmol, 10 eq) in acetone-H$_2$O (1:1, 3 mL) and shaken for a further 2 h. The solution was filtered and the resin was washed with H$_2$O (3×), acetone (1×), MeOH (2×) and CH$_2$Cl$_2$ (3×).

The resin was shaken with a solution of cyclopentylamine (0.02 mL, 0.2 mmol, 5 eq) in ClCH$_2$CH$_2$Cl (1.5 mL) for 30 min. Na(Oac)$_3$BH (0.05 g, 0.2 mmol, 5 eq) was added and the mixture shaken at room temperature for 14 h. The solution was filtered and the resin washed with MeOH (2×), DMF (3×), MeOH (3×) and CH$_2$Cl$_2$ (3×). An aliquot of the resin gave a positive chloranil test. The resin was treated with a solution of TFA (25% in CH$_2$Cl$_2$, 3 mL) and shaken for 2 h at room temperature, filtered off and the filtrate was purified by Gilson 215 HPLC (10–90% acetonitrile/water) to yield (R,S)-1-[2-(3'-Cyano-biphenyl-4-yl )-4cyclopentylamino-butyl]-3-(3,5-dichloro-phenyl)urea (0.092 g, 44%). $^1$H NMR (300 MHz, CDCl$_3$): δ 7.72 (m, 2H), 7.51 (m, 1H), 7.44 (m, 3H), 7.24 (m, 4H), 6.80 (dd, 1H), 3.26 (m, 3H), 2.84 (m, 1H), 2.65 (m, 2H), 2.05 (m, 1H), 1.88 (m, 3H), 1.65 (m, 2H), 1.47 (m, 3H); MS (ESI): 521.0 (M+1), 523.0 (M+3).

EXAMPLE 24

(R,S)-N-[2-(3'-Cyano-biphenyl-4-yl)-4-methylamino-butyl]-3,4-difluoro-benzamide

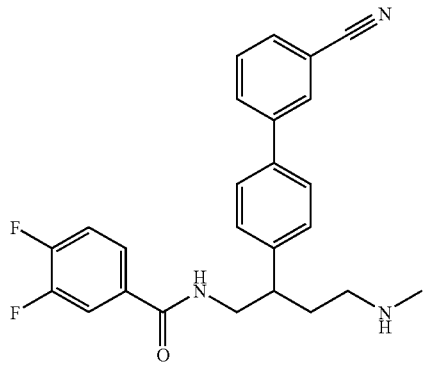

A 100 mg (0.04 mmol) portion of the 4-(4-formyl-3-methoxy-phenoxy) butyramide resin (see step 1 of EXAMPLE 20) was suspended in ClCH$_2$CH$_2$Cl (1 mL) and a solution of 1-amino-2-(4iodophenyl)-pent-5-ene (0.05 g, 0.2 mmol, 5 eq) in ClCH$_2$CH$_2$Cl (1 mL) was added. The resin was shaken for 20 min at room temperature and then Na(Oac)$_3$BH (0.045 g, 0.2 mmol, 5 eq) was added. The reaction was shaken at room temperature for 16 h. The solution was filtered and the resin was washed with MeOH (1×), DMF (3×), MeOH (3×) and CH$_2$Cl$_2$ (3×). An aliquot of the resin tested positive with chloranil and negative with 2,4-dinitrophenylhydrazine.

The resin was suspended in pyridine (1.5 mL) and 3,4difluorobenzoyl chloride (1.5 mL of a 1 M solution in CH$_2$Cl$_2$, 1.5 mmol) was added. The resin was shaken at room temperature for 16 h, the solution filtered and the resin washed with CH$_2$Cl$_2$ (3×), DMF (3×), MeOH (2×) and CH$_2$Cl$_2$ (3×). An aliquot of the resin gave a negative chloranil test.

To the resin was added 3-cyanophenylboronic acid (0.024 g, 0.16 mmol, 4 eq), K$_2$CO$_3$ (0.028 g, 0.2 mmol, 5 eq) and Pd(PPh$_3$)$_4$ (0.009 g, 0.008 mmol, 0.2 eq). DMF (2 mL, degassed with Ar) was added and the mixture was heated to 70° C. for 16 h. The solution was filtered and the resin washed with DMF (4×), H$_2$O (4×), MeOH (3×) and CH$_2$Cl$_2$ (4×).

The resin was shaken at room temperature for 14 h with a solution of OsO$_4$ (4% in H$_2$O, 0.052 mL, 0.008 mmol, 0.2 eq) and NMMO (0.05 g, 0.4 mmol, 10 eq) in acetone-H$_2$O (1:1, 3 mL) at room temperature for 14 h. The solution was filtered and the resin was washed with H$_2$O (2×), acetone (2×), pyridine (1×, shake for 30 min), MeOH (2×) and CH$_2$Cl$_2$ (3×). A solution of NaIO$_4$ (0.085 g, 0.4 mmol, 10 eq) in acetone-H$_2$O (1:1, 3 mL) was added and the mixture shaken for 2 h. The solution was filtered and the resin was washed with H$_2$O (2×), acetone (1×). The resin was treated with a fresh solution of NaIO$_4$ (0.085 g, 0.4 mmol, 10 eq) in acetone-H$_2$O (1:1, 3 mL) and shaken for a further 2 h. The solution was filtered and the resin was washed with H$_2$O (3×), acetone (1×), MeOH (2×) and CH$_2$Cl$_2$ (3×).

The resin was shaken with a solution of methylamine (0.21 mL, 2M solution, 0.4 mmol, 10 eq) in ClCH$_2$CH$_2$Cl (1.5 mL) for 30 min. Na(OAc)$_3$BH (0.05 g, 0.2 mmol, 5 eq) was added and the mixture shaken at room temperature for 14 h. The solution was filtered and the resin washed with MeOH (2×), DMF (3×), MeOH (3×) and CH$_2$Cl$_2$ (3×). An aliquot of the resin gave a positive chloranil test. The resin was treated with a solution of TFA (25% in CH$_2$Cl$_2$, 3 mL) and shaken for 2 h at room temperature, filtered off and the filtrate was purified by Gilson 215 HPLC (10–90% acetonitrile/water) to yield the title compound (0.0019 g, 11%). MS (ESI): 420.1 (M+1),421.1 (M+2).

EXAMPLE 25

(R,S)-3,5-Dichloro-N-[2-(3'-cyano-biphenyl-4-yl)-4-dimethylaminobutyl]-benzenesulfonamide

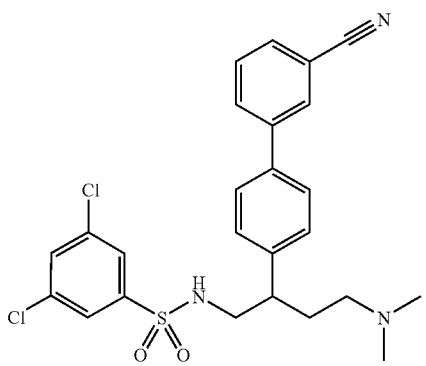

A 100 mg (0.04 mmol) portion of the 4-(4-formyl-3-methoxy-phenoxy) butyramide resin (see step 1 of EXAMPLE 20) was suspended in ClCH$_2$CH$_2$Cl (1 mL) and a solution of 1-amino-2-(4iodophenyl)-pent-5-ene (0.05 g, 0.2 mmol, 5 eq) in ClCH$_2$CH$_2$Cl (1 mL) was added. The resin was shaken for 20 min at room temperature and then Na(OAc)$_3$BH (0.045 g, 0.2 mmol, 5 eq) was added. The reaction was shaken at room temperature for 16 h. The solution was filtered and the resin was washed with MeOH (1×), DMF (3×), MeOH (3×) and CH$_2$Cl$_2$ (3×). An aliquot of the resin tested positive with chloranil and negative with 2,4-dinitrophenylhydrazine.

The resin was suspended in pyridine (1.5 mL) and 3,5-dichlorobenzenesulfonyl chloride (1.5 mL of a 1 M solution in CH$_2$Cl$_2$, 1.5 mmol) was added. The resin was shaken at room temperature for 16 h, the solution filtered and the resin washed with CH$_2$Cl$_2$ (3×), DMF (3×), MeOH (2×) and CH$_2$Cl$_2$ (3×). An aliquot of the resin gave a negative chloranil test.

The resin was shaken at room temperature for 14 h with a solution of OsO$_4$ (4% in H$_2$O, 0.052 mL, 0.008 mmol, 0.2 eq) and NMMO (0.05 g, 0.4 mmol, 10 eq) in acetone-H$_2$O (1:1, 3 mL) at room temperature for 14 h. The solution was filtered and the resin was washed with H$_2$O (2×), acetone (2×), pyridine (1×, shake for 30 min), MeOH (2×) and CH$_2$Cl$_2$ (3×). A solution of NaIO$_4$ (0.085 g, 0.4 mmol, 10 eq) in acetone-H$_2$O (1:1, 3 mL) was added and the mixture shaken for 2 h. The solution was filtered and the resin was washed with H$_2$O (2×), acetone (1×). The resin was treated with a fresh solution of NaIO$_4$ (0.085 g, 0.4 mmol, 10 eq) in acetone-H$_2$O (1:1, 3 mL) and shaken for a further 2 h. The solution was filtered and the resin was washed with H$_2$O (3×), acetone (1×), MeOH (2×) and CH$_2$Cl$_2$ (3×).

The resin was shaken with a solution of dimethylamine (0.10 mL of a 2 M solution in THF, 0.2 mmol, 5 eq) in ClCH$_2$CH$_2$Cl (1.5 mL) for 30 min. Na(OAc)$_3$BH (0.05 g, 0.2 mmol, 5 eq) was added and the mixture shaken at room temperature for 14 h. The solution was filtered and the resin washed with MeOH (2×), DMF (3×), MeOH (3×) and CH$_2$Cl$_2$ (3×). An aliquot of the resin gave a positive chloranil test. The resin was treated with a solution of TFA (TFA, 25% in CH$_2$Cl$_2$, 3 mL) and shaken for 2 h at room temperature, filtered off and the filtrate was purified by Gilson 215 HPLC (10–90% acetonitrile/water) to yield the title compound (0.0024 g, 12%). MS (ESI): 502.1/504.1 (M+1).

EXAMPLE 26

(R,S)-[-2-(3'-Cyano-biphenyl-4-yl)-4-isopropylaminobutyl]-carbamic acid-4-chlorophenyl ester

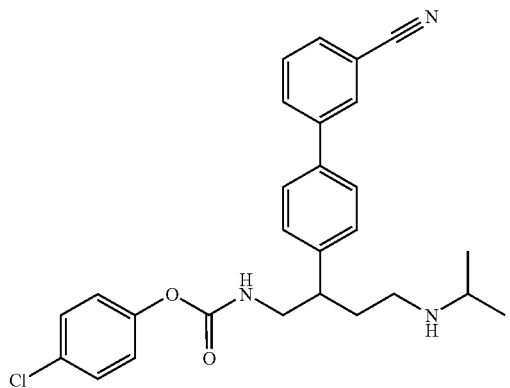

A 100 mg (0.04 mmol) portion of the 4-(4-formyl-3-methoxy-phenoxy) butyramide resin (see step 1 of EXAMPLE 20) was suspended in ClCH$_2$CH$_2$Cl (1 mL) and a solution of 1-amino-2-(4iodophenyl)-pent-5-ene (0.05 g, 0.2 mmol, 5 eq) in ClCH$_2$CH$_2$Cl (1 mL) was added. The resin was shaken for 20 min at room temperature and then Na(OAc)$_3$BH (0.045 g, 0.2 mmol, 5 eq) was added. The reaction was shaken at room temperature for 16 h. The solution was filtered and the resin was washed with MeOH (1×), DMF (3×), MeOH (3×) and CH$_2$Cl$_2$ (3×). An aliquot of the resin tested positive with chloranil and negative with 2,4-dinitrophenylhydrazine.

The resin was suspended in pyridine (1.5 mL) and 4chlorophenyl chloroformate (1.5 mL of a 1 M solution in CH$_2$Cl$_2$, 1.5 mmol) was added. The resin was shaken at room temperature for 16 h, the solution filtered and the resin washed with CH$_2$Cl$_2$ (3×), DMF (3×), MeOH (2×) and CH$_2$Cl$_2$ (3×). An aliquot of the resin gave a negative chloranil test.

The resin was shaken at room temperature for 14 h with a solution of OsO$_4$ (4% in H$_2$O, 0.052 mL, 0.008 mmol, 0.2 eq) and NMMO (0.05 g, 0.4 mmol, 10 eq) in acetone-H$_2$O (1:1, 3 mL) at room temperature for 14 h. The solution was filtered and the resin was washed with H$_2$O (2×), acetone (2×), pyridine (1×, shake for 30 min), MeOH (2×) and CH$_2$Cl$_2$ (3×). A solution of NaIO$_4$ (0.085 g, 0.4 mmol, 10 eq) in acetone-H$_2$O (1:1, 3 mL) was added and the mixture shaken for 2 h. The solution was filtered and the resin was washed with H$_2$O (2×), acetone (1×). The resin was treated with a fresh solution of NaIO$_4$ (0.085 g, 0.4 mmol, 10 eq) in acetone-H$_2$O (1:1, 3 mL) and shaken for a further 2 h. The solution was filtered and the resin was washed with H$_2$O (3×), acetone (1×), MeOH (2×) and CH$_2$Cl$_2$ (3×).

The resin was shaken with a solution of isopropylamine (0.02 mL, 0.2 mmol, 5 eq) in ClCH$_2$CH$_2$Cl (1.5 mL) for 30 min. Na(OAc)$_3$BH (0.05g, 0.2 mmol, 5 eq) was added and the mixture shaken at room temperature for 14 h. The solution was filtered and the resin washed with MeOH (2×), DMF (3×), MeOH (3×) and CH$_2$Cl$_2$ (3×). An aliquot of the resin gave a positive chloranil test. The resin was treated with a solution of TFA (TFA, 25% in CH$_2$Cl$_2$, 3 mL) and shaken for 2 h at room temperature, filtered off and the filtrate was purified by Gilson 215 HPLC (10–90% acetonitrile/water) to yield the title compound (0.0027 g, 15%). MS (ESI): 460.1/462.2 (M+1).

EXAMPLE 27

(R,S)-1-1-{3-(3'-Cyano-biphenyl-4-yl)-4-[3 (3,5-dichloro-phenyl)-ureido]-butyl}-pyrrolidin-3-yl)-3-ethyl-urea

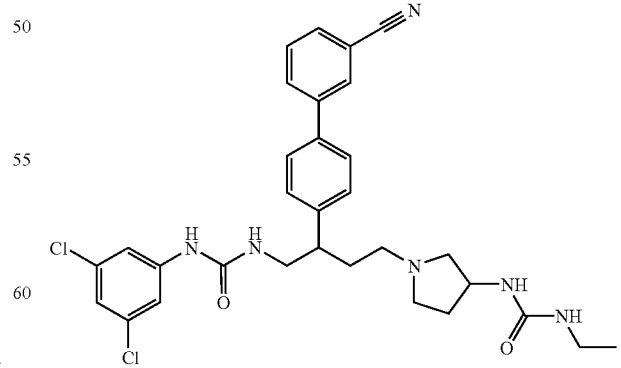

A 100 mg (0.04 mmol) portion of the 4-(4-formyl-3-methoxy-phenoxy)-butyramide resin (see step 1 of EXAMPLE 20) was suspended in ClCH$_2$CH$_2$Cl (1 mL) and a solution of 1-amino-2-(4-bromophenyl)-pent-5-ene (0.048 g, 0.2 mmol, 5 eq) in ClCH₂CH₂Cl (1 mL) was added. The resin was shaken for 20 min at room temperature and then Na(OAc)₃BH (0.045 g, 0.2 mmol, 5 eq) was added. The reaction was shaken at room temperature for 16 h. The solution was filtered and the resin was washed with MeOH (1×), DMF (3×), MeOH (3×) and CH₂Cl₂ (3×). An aliquot of the resin tested positive with chloranil and negative with 2,4-dinitrophenylhydrazine.

The resin was suspended in CH₂Cl₂ (3.0 mL) and DIEA (0.035 mL, 0.2 mmol, 5 eq) was added followed by 3,5-dichloro-phenyl isocyanate (10.283 g, 1.5 mmol, to give a 0.5 M solution). The resin was shaken at room temperature for 16 h, the solution filtered and the resin washed with CH₂Cl₂ (3×), DMF (3×), MeOH (2×) and CH₂Cl₂ (3×). An aliquot of the resin gave a negative chloranil test.

To the resin was added 3-cyanophenylboronic acid (0.024 g, 0.16 mmol, 4 eq), K₂CO₃ (0.028 g, 0.2 mmol, 5 eq) and Pd(PPh₃)₄ (0.009 g, 0.008 mmol, 0.2 eq). DMF (2 mL, degassed with Ar) was added and the mixture was heated to 70° C. for 16 h. The solution was filtered and the resin washed with DMF (4×), H₂O (4×), MeOH (3×) and CH₂Cl₂ (4×).

The resin was shaken at room temperature for 14 h with a solution of OsO₄ (4% in H₂O, 0.052 mL, 0.008 mmol, 0.2 eq) and NMMO (0.05 g, 0.4 mmol, 10 eq) in acetone-H₂O (1:1, 3 mL) at room temperature for 14 h. The solution was filtered and the resin was washed with H₂O (2×), acetone (2×), pyridine (1×, shake for 30 min), MeOH (2×) and CH₂Cl₂ (3×). A solution of NaIO₄ (0.085 g, 0.4 mmol, 10 eq) in acetone-H₂O (1:1, 3 mL) was added and the mixture shaken for 2 h. The solution was filtered and the resin was washed with H₂O (2×), acetone (1×). The resin was treated with a fresh solution of NaIO₄ (0.085 g, 0.4 mmol, 10 eq) in acetone-H₂O (1:1, 3 mL) and shaken for a further 2 h. The solution was filtered and the resin was washed with H₂O (3×), acetone (1×), MeOH (2×) and CH₂Cl₂ (3×).

The resin was shaken with a solution of pyrrolidin3-yl-carbamic acid tert-butyl ester (0.037 g, 0.2 mmol, 5 eq) in ClCH₂CH₂Cl (1.5 mL) for 30 min. Na(OAc)₃BH (0.05 g, 0.2 mmol, 5 eq) was added and the mixture shaken at room temperature for 14 h. The solution was filtered and the resin washed with MeOH (2×), DMF (3×), MeOH (3×) and CH₂Cl₂ (3×).

The resin was suspended in CH₂Cl₂ (3 mL) and treated with 2,6-lutidine (0.52 mL, 4.5 mmol, 1.5M final concentration) and TMSOTf (0.54 mL, 3 mmol, 1M final concentration). The mixture was shaken at room temperature for 1 h. The mixture was drained and the resin washed with CH₂Cl₂ (3×), MeOH (3×) and CH₂Cl₂ (3×). An aliquot of the resin gave a positive ninhydrin test.

The resin was suspended in CH₂Cl₂ (3 mL) and treated with ethyl isocyanate (0.19 mL, 1.5 mmol, 0.5M final concentration) and DIEA (0.035 mL, 0.2 mmol, 5 eq). The mixture was shaken at room temperature for 14 h and then the solution was filtered and the resin was washed with DMF (3×), MeOH (3×) and CH₂Cl₂ (3×).

The resin was treated with a solution of TFA (25% in CH₂Cl₂, 3 mL) and shaken for 2 h at room temperature, filtered off and the filtrate was purified by Gilson 215 HPLC (10–90% acetonitrile/water) to yield the title compound (0.0011 g, 5%). MS(ESI): 593.1 (M+1), 595.1 (M+3).

EXAMPLE 28

(R,S)-3,5-Dichloro-N-(1-{3-(3'-cyano-biphenyl-4-yl)-4-[3-(3,5-dichloro-phenyl)-ureido]-butyl}-pyrrolidin-3-yl)-benzamide

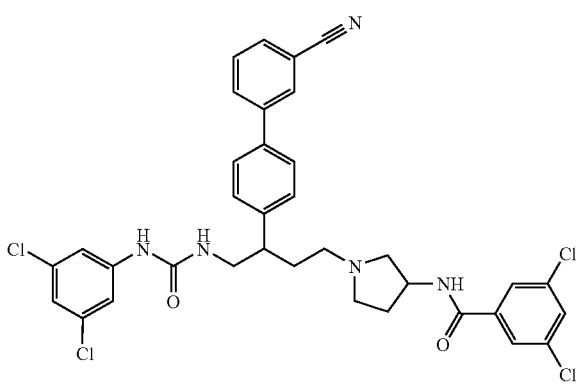

A 100 mg (0.04 mmol) portion of the 4-(4-formyl-3-methoxy-phenoxy) butyramide resin (see step 1 of EXAMPLE 20) was suspended in ClCH₂CH₂Cl (1 mL) and a solution of 1-amino-2-(4-bromophenyl)-pent-5-ene (0.048 g, 0.2 mmol, 5 eq) in ClCH₂CH₂Cl (1 mL) was added. The resin was shaken for 20 min at room temperature and then Na(OAc)₃BH (0.045 g, 0.2 mmol, 5 eq) was added. The reaction was shaken at room temperature for 16 h. The solution was filtered and the resin was washed with MeOH (1×), DMF (3×), MeOH (3×) and CH₂Cl₂ (3×). An aliquot of the resin tested positive with chloranil and negative with 2,4-dinitrophenylhydrazine.

The resin was suspended in CH₂Cl₂ (3.0 mL) and DIEA (0.035 mL, 0.2 mmol, 5 eq) was added followed by 3,5-dichloro-phenyl isocyanate (10.283 g, 1.5 mmol, to give a 0.5 M solution). The resin was shaken at room temperature for 16 h, the solution filtered and the resin washed with CH₂Cl₂ (3×), DMF (3×), MeOH (2×) and CH₂Cl₂ (3×). An aliquot of the resin gave a negative chloranil test.

To the resin was added 3-cyanophenylboronic acid (0.024 g, 0.16 mmol, 4 eq), K₂CO₃ (0.028 g, 0.2 mmol, 5 eq) and Pd(PPh₃)₄ (0.009 g, 0.008 mmol, 0.2 eq). DMF (2 mL, degassed with Ar) was added and the mixture was heated to 70° C. for 16 h. The solution was filtered and the resin washed with DMF (4×), H₂O (4×), MeOH (3×) and CH₂Cl₂ (4×).

The resin was shaken at room temperature for 14 h with a solution of OsO₄ (4% in H₂O, 0.052 mL, 0.008 mmol, 0.2 eq) and NMMO (0.05 g, 0.4 mmol, 10 eq) in acetone-H₂O (1:1, 3 mL) at room temperature for 14 h. The solution was filtered and the resin was washed with H₂O (2×), acetone (2×), pyridine (1×, shake for 30 min), MeOH (2×) and CH₂Cl₂ (3×). A solution of NaIO₄ (0.085 g, 0.4 mmol, 10 eq) in acetone-H₂O (1:1, 3 mL) was added and the mixture shaken for 2 h. The solution was filtered and the resin was washed with H₂O (2×), acetone (1×). The resin was treated with a fresh solution of NaIO₄ (0.085 g, 0.4 mmol, 10 eq) in acetone-H₂O (1:1, 3 mL) and shaken for a further 2 h. The solution was filtered and the resin was washed with H₂O (3×), acetone (1×), MeOH (2×) and CH₂Cl₂ (3×).

The resin was shaken with a solution of pyrrolidin3-yl-carbamic acid tert-butyl ester (0.037 g, 0.2 mmol, 5 eq) in ClCH₂CH₂Cl (1.5 mL) for 30 min. Na(OAc)₃BH (0.05 g, 0.2 mmol, 5 eq) was added and the mixture shaken at room temperature for 14 h. The solution was filtered and the resin washed with MeOH (2×), DMF (3×), MeOH (3×) and CH$_2$Cl$_2$ (3×).

The resin was suspended in CH$_2$Cl$_2$ (3 mL) and treated with 2,6-lutidine (0.52 mL, 4.5 mmol, 1.5M final concentration) and TMSOTf (0.54 mL, 3 mmol, 1M final concentration). The mixture was shaken at room temperature for 1 h. The mixture was drained and the resin washed with CH$_2$Cl$_2$ (3×), MeOH (3×) and CH$_2$Cl$_2$ (3×). An aliquot of the resin gave a positive ninhydrin test.

The resin was suspended in CH$_2$Cl$_2$ (1.5 mL) and treated with 3,5-dichloro-benzoyl chloride (0.315 g, 1.5 mmol) and pyridine (1.5 mL). The mixture was shaken at room temperature for 14 h and then the solution was filtered and the resin was washed with DMF (3×), MeOH (3×) and CH$_2$Cl$_2$ (3×).

The resin was treated with a solution of TFA (25% in CH$_2$Cl$_2$, 3 mL) and shaken for 2 h at room temperature, filtered off and the filtrate was purified by Gilson 215 HPLC (10–90% acetonitrile/water) to yield the title compound (0.0023 g, 9%). MS(ESI): 693.9/695.9/697.9 (M+1).

EXAMPLE 29

(R,S)-N-(1-{3-(3'-Cyano-biphenyl-4-yl)-4-[3-(3,5-dichloro-phenyl)-ureido]- butyl}-piperidin-4-yl) methane-sulfonamide

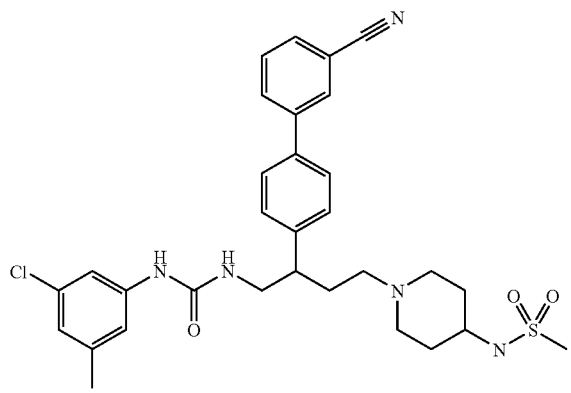

A 100 mg (0.04 mmol) portion of the 4-(4-formyl-3-methoxy-phenoxy)-butyramide resin (see step 1 of EXAMPLE 20) was suspended in ClCH$_2$CH$_2$Cl (1 mL) and a solution of 1-amino-2-(4-bromophenyl)-pent-5-ene (0.048 g, 0.2 mmol, 5 eq) in ClCH$_2$CH$_2$Cl (1 mL) was added. The resin was shaken for 20 min at room temperature and then Na(OAc)$_3$BH (0.045 g, 0.2 mmol, 5 eq) was added. The reaction was shaken at room temperature for 16 h. The solution was filtered and the resin was washed with MeOH (1×), DMF (3×), MeOH (3×) and CH$_2$Cl$_2$ (3×). An aliquot of the resin tested positive with chloranil and negative with 2,4-dinitrophenylhydrazine.

The resin was suspended in CH$_2$Cl$_2$ (3.0 mL) and DIEA (0.035 mL, 0.2 mmol, eq) was added followed by 3,5-dichloro-phenyl isocyanate (0.283g, 1.5 mmol, to give a 0.5 M solution). The resin was shaken at room temperature for 16 h, the solution filtered and the resin washed with CH$_2$Cl$_2$ (3×), DMF (3×), MeOH (2×) and CH$_2$Cl$_2$ (3×). An aliquot of the resin gave a negative chloranil test.

The resin was added 3-cyanophenylboronic acid (0.024 g, 0.16 mmol, 4 eq), K$_2$CO$_3$ (0.028 m, 0.2 mmol, 5 eq) and Pd(PPh$_3$)$_4$ (0.009 g, 0.008 mmol, 0.2 eq). DMF (2 mL, degassed with Ar) was added and the mixture was heated to 70° C. for 16 h. The solution was filtered and the resin washed with DMF (4×), H$_2$O (4×), MeOH (3×) and CH$_2$Cl$_2$ (4×).

The resin was shaken at room temperature for 14 h with a solution of OsO$_4$ (4% in H$_2$O, 0.052 mL, 0.008 mmol, 0.2 eq) and NMMO (0.05 g, 0.4 mmol, 10 eq) in acetone-H$_2$O (1:1, 3 mL) at room temperature for 14 h. The solution was filtered and the resin was washed with H$_2$O (2×), acetone (2×), pyridine (1×, shake for 30 min), MeOH (2×) and CH$_2$Cl$_2$ (3×). A solution of NaIO$_4$ (0.085 g, 0.4 mmol, 10 eq) in acetone-H$_2$O (1:1, 3 mL) was added and the mixture shaken for 2 h. The solution was filtered and the resin was washed with H$_2$O (2×), acetone (1×). The resin was treated with a fresh solution of NaIO$_4$ (0.085 g, 0.4 mmol, 10 eq) in acetone-H$_2$O (1:1, 3 mL) and shaken for a further 2 h. The solution was filtered and the resin was washed with H$_2$O (3×), acetone (1×), MeOH (2×) and CH$_2$Cl$_2$ (3×).

The resin was shaken with a solution of piperidin4-yl-carbamic acid tert-butyl ester (0.043 g, 0.2 mmol, 5 eq) in ClCH$_2$CH$_2$Cl (1.5 mL) for 30 min. Na(OAc)$_3$BH (0.05 g, 0.2 mmol, 5 eq) was added and the mixture shaken at room temperature for 14 h. The solution was filtered and the resin washed with MeOH (2×), DMF (3×), MeOH (3×) and CH$_2$Cl$_2$ (3×).

The resin was suspended in CH$_2$Cl$_2$ (3 mL) and treated with 2,6-lutidine (0.52 mL, 4.5 mmol, 1.5M final concentration) and TMSOTf (0.54 mL, 3 mmol, 1M final concentration). The mixture was shaken at room temperature for 1 h. The solution was filtered and the resin was washed with CH$_2$Cl$_2$ (3×), MeOH (3×) and CH$_2$Cl$_2$ (3×). An aliquot of the resin gave a positive ninhydrin test.

The resin was suspended in pyridine (1.5 mL) and treated with methanesulfonyl chloride (1.5 mL of a 1.0M solution in CH$_2$Cl$_2$). The mixture was is shaken at room temperature for 14 h. The solution was filtered and the resin was washed DMF (3×), MeOH (3×) and CH$_2$Cl$_2$ (3×).

The resin was treated with a solution of TFA (25% in CH$_2$Cl$_2$, 3 mL) and shaken for 2 h at room temperature, filtered off and the filtrate was purified by Gilson 215 HPLC (10–90% acetonitrile/water) to yield the title compound (0.0012 g, 5%). MS (ESI): 614.1 (M+1), 616.1 (M+3).

EXAMPLE 30

(R,S)-N-(3,5-Bistrifluoromethyl-benzyl)-4-(cyclo-hexyl-methyl-amino)-2-(3,4-dichloro-phenyl)-bu-tyramide

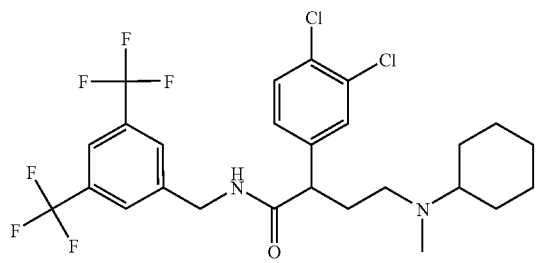

A 100 mg (0.04 mmol) portion of the 4-(4-formyl-3-methoxy-phenoxy)-butyramide resin (see step 1 of EXAMPLE 20) was suspended in ClCH$_2$CH$_2$Cl (1 mL) and a solution of 3,5bistrifluoromethylbenzyl amine (0.05 g, 0.2 mmol, 5 eq) in ClCH$_2$CH$_2$Cl (1 mL) was added. The resin was shaken for 20 min at room temperature and then NaBH(OAc)$_3$ (0.045 g, 0.2 mmol, 5 eq) was added. The mixture was shaken at room temperature for 16 h. The solution was filtered and the resin was washed with MeOH (1×), DMF (3×), MeOH (3×) and CH$_2$Cl$_2$ (3×). An aliquot of the resin tested positive with chloranil and negative with 2,4-dinitrophenylhydrazine.

The resin was suspended in pyridine (1 mL) and a solution of 2-(3,4-dichloro-phenyl)-pent-4-enoyl chloride (~0.054 g, 0.2 mmol, 5 eq) in CH$_2$Cl$_2$ (1 mL) was added. The resin was shaken at room temperature for 16 h. The solution was filtered and the resin was washed with MeOH (3×), DMF (3×), MeOH (3×) and CH$_2$Cl$_2$ (3×). This procedure was repeated using the same reaction and washing conditions. An aliquot of the resin gave a negative bead test with chloranil. The resin was shaken at room temperature for 14 h with a solution of OsO$_4$ (4% in H$_2$O, 0.052 mL, 0.008 mmol, 0.2 eq) and NMMO (0.05 g, 0.4 mmol, 10 eq) in acetone-H$_2$O (1:1, 3 mL) at room temperature for 14 h. The solution was filtered and the resin was washed with H$_2$O (2×), acetone (2×), pyridine (1×, shake for 30 min), MeOH (2×) and CH$_2$Cl$_2$ (3×). A solution of NaIO$_4$ (0.085 g, 0.4 mmol, 10 eq) in acetone-H$_2$O (1:1, 3 mL) was added and the mixture shaken for 2 h. The solution was filtered and the resin was washed with H$_2$O (2×), acetone (1×). The resin was treated with a fresh solution of NaIO$_4$ (0.085 g, 0.4 mmol, 10 eq) in acetone-H$_2$O (1:1, 3 mL) and shaken for a further 2 h. The solution was filtered and the resin was washed with H$_2$O (3×), acetone (1×), MeOH (2×) and CH$_2$Cl$_2$ (3×).

The resin was shaken with a solution of N-methylcyclohexylamine 0.026 mL, 0.2 mmol, 5 eq) in ClCH$_2$CH$_2$Cl (1.5 mL) for 30 min. Na(OAc)$_3$BH (0.05 g, 0.2 mmol, 5 eq) was added and the mixture shaken at room temperature for 14 h. The solution was filtered and the resin washed with MeOH (2×), DMF (3×), MeOH (3×) and CH$_2$Cl$_2$ (3×). An aliquot of the resin gave a positive chloranil test. The resin was treated with a solution of TFA (25% in CH$_2$Cl$_2$, 3 mL) and shaken for 2 h at room temperature, filtered off and the filtrate was concentrated and purified by Gilson 215 HPLC (10–90% acetonitrile/water) to yield the title compound (0.0039 g, 15%). MS(ESI): 569.1 (M+1), 571.2 (M+3).

EXAMPLE 31

2-(3'-Cyano-biphenyl-4-yl)-N-(3,5-dichloro-phenyl)-4-methylamino-butyramide

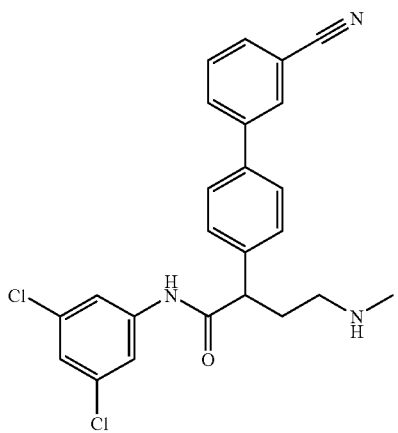

To a solution of 4-bromophenylpent-4-enoyl chloride (1.0 g, 3.7 mmol, EXAMPLE 18) in CH$_2$Cl$_2$ (15 mL) was added 3,5-dichloroaniline (0.74 g, 4.5 mmol, 1.2 eq) and Et$_3$N (1.5 mL, 11.1 mmol, 3 eq). The reaction mixture was stirred at r.t. for 16 h. The mixture was washed with 10% NaHCO$_3$ (10 mL), H$_2$O (10 mL), 1N HCl (10 mL) and saturated brine, dried (Na$_2$SO$_4$), and concentrated. Chromatography on silica gel (10% EtOAc/hexanes) gave 2-(4-bromophenyl)-pent-4-enoic acid (3,5-dichloro-phenyl)-amide as a yellow oil (1.5 g, 100%). $^1$H NMR (300 MHz, CDCl$_3$): δ 7.62 (d, 2H), 7.53 (d, 2H), 7.33 (d, 2H), 7.19 (t, 1H), 5.83 (m, 1H), 5.17 (m, 2H), 3.62 (t, 1H), 3.03 (m, 1H), 2.65 (m, 1H).

To an Argon-purged solution of 2-(4-bromophenyl)-pent-4-enoic acid (3,5-dichloro-phenyl)-amide (1.5 g, 3.7 mmol) in toluene/EtOH (2:1 v/v, 30 mL) was added 3-cyanophenylboronic acid (0.99 g, 6.7 mmol, 1.8 eq), Pd(PPh$_3$)$_4$ (160 mg, 0.44 mmol, 12%), and a solution of Na$_2$CO$_3$ (2.12 g, 20 mmol, 5.4 eq) in 10 mL of water. The reaction mixture was heated at 90° C. for 16 h. The mixture was partitioned between EtOAc (50 mL) and 10% NaHCO$_3$ (50 mL) and the organic phase separated. The organic phase was washed with 10% NaHCO$_3$ (30 mL) and saturated brine (30 mL), dried (Na$_2$SO$_4$), and concentrated. Chromatography on silica gel (20% EtOAc/hexanes) gave 2-(3'-cyano-biphenyl-4-yl)-pent-4-enoic acid (3,5-dichloro-phenyl)-amide as a yellow oil (685 mg, 44%). $^1$H NMR (300 MHz, CD$_3$OD): δ 7.93 (m, 2H), 7.81 (m, 2H), 7.66 (m, 4H), 7.49 (m, 2H), 7.12 (t, 1H), 5.89 (m, 1H), 5.21 (m, 2H), 3.76 (t, 1H), 3.11 (m, 1H), 2.73 (m, 1H).

To a solution of 2-(3'-cyano-biphenyl-4-yl)-pent-4-enoic acid (3,5-dichloro-phenyl)-amide (680 mg, 1.6 mmol) in 9 mL of acetone/H$_2$O (2:1 v/v) was added OsO$_4$ (4% in H$_2$O, 100 L, 1 mmol %) and NaIO$_4$ (860 mg, 4.0 mmol, 2.5 eq). The reaction mixture was stirred at r.t. for 6 h. The mixture was then partitioned between CH$_2$Cl$_2$ (20 mL) and 10% NaHCO$_3$ (20 mL) and the organic layer separated. The aqueous layer was extracted with CH$_2$Cl$_2$ (10 mL×3) and the combined organic layer was washed with saturated brine (10 mL), dried (Na$_2$SO$_4$), and concentrated. Chromatography on silica gel (20% EtOAc/hexanes) gave 2-(3'-cyano-biphenyl-4-yl)-N-(3,5-dichloro-phenyl)-4-oxobutyramide as a light yellow oil (300 mg, 44%). MS(ESI): 423.0 (M+1).

A mixture of 2-(3'-cyano-biphenyl-4-yl)-N-(3,5-dichloro-phenyl)-4oxo-butyramide (300 mg, 0.71 mmol) and MeNH$_2$ (2M in THF, 1.77 mL, 3.54 mmol, 5 eq) in 1,2-dichloroethane (3.5 mL) was stirred at r.t. for 1 h and then Na(AcO)$_3$BH (299 mg, 1.4 mmol, 2 eq) was added. The reaction mixture was stirred at r.t. for 16 h. The mixture was then partitioned between EtOAc (20 mL) and 10% NaHCO$_3$ (10 mL) and the organic phase separated. The organic phase was washed with 10% NaHCO$_3$ (10 mL×2), saturated brine (10 mL), dried (Na$_2$SO$_4$), and concentrated. Chromatography on silica gel (Et$_3$N/MeOH/CH$_2$Cl$_2$ 1:10:90) gave 56.5 mg (18%) of the title compound as a yellowish gum. $^1$H NMR (300 MHz, CDCl$_3$): δ 7.89 (m, 2H), 7.72 (m, 1H), 7.61 (m, 7H), 7.14 (t, 1H), 4.04 (dd, 1H), 2.85 (t, 2H), 2.59 (s, 3H), 2.50 (m, 1H), 2.16 (m, 1H). MS(ESI): 438.0 (M+1), 440.0 (M+3).

EXAMPLE 32

4'-{1-[3-(3,5-Dichlorophemyl)-2-oxoimidazolidin-1-ylmethyl]-3-dimethylaminopropyl}-biphenyl-3-carbonitrile

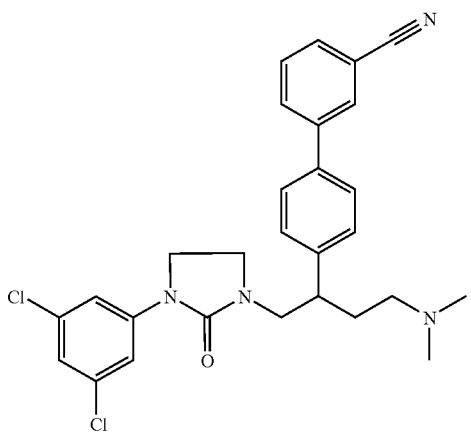

A solution of 3,5-dichloro-phenyl isocyanate (5 g, 26.6 mmol) in t-BuOH (100 mL) was heated at 80° C. for 16 h. The mixture was concentrated by rotary evaporation to give a white solid which was triturated with toluene and evaporated to dryness. Addition of toluene and concentration under vacuum gave (3,5-dichloro-phenyl)carbamic acid-tert-butyl ester as a white solid (6 g, 22.9 mmol, 84%). $^1$H NMR (300 MHz, CDCl$_3$): δ 7.42 (s, 2H), 7.18 (s, 1H), 6.6 (br s, NH), 1.62 (s, 9H).

To a solution of (3,5-dichloro-phenyl)-carbamic acid-tert-butyl ester (6 g, 22.89 mmol) in DMF (130 mL) at 0° C. under Ar was added NaH (60% dispersion in mineral oil, 1.725 g, 45 mmol, 2 eq). The mixture was stirred at 0° C. for 30 min and then allyl iodide (13.32 mL, 110 mmol, 5 eq) was added over 5 min. The mixture was warmed to room temperature and stirred for 2 h. The mixture was then diluted with EtOAc (200 mL) and washed with saturated aqueous NaHCO$_3$ (200 mL). The aqueous phase was washed with EtOAc (3×60 mL) and the combined organic extracts were washed with saturated aqueous NaCl (200 mL), dried over Na$_2$SO$_4$, filtered and concentrated to give a brown oil which was purified by flash column chromatography eluting with 2% EtOAc/hexanes to give allyl(3,5-dichloro-phenyl)-carbamic acid-tert-butyl ester as a clear oil (4.632 g, 15.33 mmol, 67%).). $^1$H NMR (300 MHz, CDCl$_3$): δ 7.41 (s, 1H), 7.24 (m, 2H), 6.00 (m, 1H), 5.30 (m, 2H), 4.30 (m, 2H), 1.59 (s, 9H).

A stirred solution of allyl-(3,5-dichloro-phenyl)-carbamic acid-tert-butyl ester (2.32 g, 7.68 mmol) in CH$_2$Cl$_2$ (75 mL) was cooled to –78° C. Ozone was bubbled through for ~5 min (reaction monitored by tlc). Oxygen was then bubbled through for 5 min. Me$_2$S (5 mL, 77 mmol, 10 eq) was added and the mixture was warmed to room temperature and stirred for 6 h. Following a further addition of Me$_2$S (5 mL, 77 mmol, 10 eq) the mixture was stirred at room temperature for 14 h. The mixture was concentrated by rotary evaporation and the resulting residue was purified by flash column chromatography eluting with 25% EtOAc/hexanes to yield (3,5-dichloro-phenyl)-(2-oxo-ethyl)-carbamic acid-tert-butyl ester (1.61 g, 5.3 mmol, 69%) as a pale oil. $^1$H NMR (300 MHz, CDCl$_3$): δ 9.80 (s, 1H), 7.30 (m, 3H), 4.45 (s, 2H), 1.56 (s, 9H).

To a stirred solution of (3,5-dichloro-phenyl)-(2-oxoethyl)-carbamic acid-tert-butyl ester (0.75 g, 2.46 mmol) in MeOH (15 mL) under Ar at room temperature was added a solution of (R,S) 2-(4-iodophenyl)-pent-4-enylamine (0.741 g, 2.58 mmol, 1.05 eq) in MeOH (5 mL). The mixture was stirred at room temperature for 5 h. NaBH$_4$ (0.140 g, 3.69 mmol, 1.5 eq) was added and the resulting mixture was stirred for a further 1 h, quenched by the addition of NaOH (1 M aqueous solution, 20 mL). The mixture was extracted twice with Et$_2$O (50 mL total) and the combined organic extracts were washed with saturated aqueous NaCl and dried over Na$_2$SO$_4$. Filtration and concentration of the filtrate by rotary evaporation gave the crude product which was purified by flash column chromatography eluting 12% EtOAc/hexanes to give (3,5-Dichloro-phenyl)-{2-[2-(4-iodo-phenyl)-pent-4-enylamino]-ethyl}-carbamic acid tert-butyl ester (0.493 g, 0.85 mmol, 35%) as a pale oil. $^1$H NMR (300 MHz, CDCl$_3$): δ 7.75 (d, 2H), 7.29 (td, 2H), 7.18 (d, 2H), 7.04 (d, 2H), 5.74 (m, 1H), 5.06 (m, 2H), 3.74 (td, 2H), 2.82 (m, 5H), 2.44 (m, 2H), 1.52 (s, 9H).

To a stirred solution of (3,5-dichloro-phenyl)-{2-[2-(4-iodophenyl)-pent-4-enylamino]-ethyl}-carbamic acid tert-butyl ester (0.493 g, 0.85 mmol) in CH$_2$Cl$_2$ (20 mL) at 0° C. was added TFA (5 mL). The mixture was stirred and warmed to room temperature for 4 h. The solvent was removed by rotary evaporation and the residue was dissolved in EtOAc and washed twice with NaHCO$_3$ (10% in H$_2$O). The organic extracts were dried over sodium sulfate, filtered and concentrated by rotary evaporation to give N-(3,5-dichloro-phenyl)-N'-[2-(4-iodo-phenyl)-pent-4-enyl]-ethane-1,2-diamine (0.386 g, 0.81 mmol, 95%) as a brown oil. $^1$H NMR (300 MHz, CDCl$_3$): δ 7.73 (d, 2H), 7.03 (d, 2H), 6.56 (t, 1H), 6.50 (d, 2H), 5.75 (m, 1H), 5.08 (m, 2H), 4.42 (br s, NH), 3.15 (m, 2H), 3.40 (m, 5H), 2.44 (m, 2H).

To a stirred solution of N-(3,5-dichloro-phenyl)-N'-[2-(4-iodo-phenyl)-pent-4-enyl]-ethane-1,2-diamine (0.386 g, 0.81 mmol) in toluene (10 mL) was added CDI (0.18 g, 1.1 mmol, 1.4 eq). The mixture was heated to 100° C. for 16 h, then cooled to room temperature, diluted with EtOAc (25 mL) and washed twice with saturated aqueous NaCl (25 mL). The organic extracts were dried over sodium sulfate, filtered and concentrated by rotary evaporation to give a dark brown oil. The crude product was purified by flash column chromatography eluting with 10% EtOAc/hexanes to give 1-(3,5-dichloro-phenyl)-3-[2-(4-iodo-phenyl)-pent-4-enyl]-imidazolidin-2-one (0.128 g, 0.255 mmol, 30%) as a pale foam. $^1$H NMR (300 MHz, CDCl$_3$): δ 7.74 (d, 2H), 7.54 (d, 2H), 7.20 (m, 3H), 5.75 (m, 1H), 5.10 (m, 2H), 3.74 (m, 3H), 3.38 (m, 2H), 3.22 (m, 1H), 3.08 (m, 1H), 2.50 (m, 2H).

A solution of 1-(3,5-dichloro-phenyl)-3-[2-(4-iodo-phenyl)-pent-4-enyl]-imidazolidin-2-one (0.128 g, 0.255 mmol), 3-cyanophenyl boronic acid (0.113 g, 0.766 mmol, 3 eq), tris(dibenzylidene-acetone)-dipalladium(O) (0.025g, 0.0255 mmol, 10 mol %), triphenylarsine (0.031 g, 0.1 mmol, 40 mol %) and cesium fluoride (0.075 g, 0.51 mmol, 2 eq) in DME (13 mL) and ethanol (3 mL) was microwaved at 50W for 7 h and then at 100W for 1 h. The mixture was diluted with EtOAc (50 mL), filtered through a pad of celite 545® and the filtrate washed with saturated aqueous Na$_2$CO$_3$ solution (25 mL). The aqueous layer was extracted twice with EtOAc (50 mL). The combined organic extracts were washed with saturated aqueous Na$_2$CO$_3$ solution (25 mL) and saturated aqueous sodium chloride solution (25 mL).

The organic layer was separated, dried over sodium sulfate, filtered and concentrated to give a dark oil. Purification by flash column chromatography eluting 15–20% EtOAc/hexanes gave 4'-{1-[3-(3,5-dichloro-phenyl)-2-oxo-imidazolidin-1-ylmethyl]-but-3-enyl}-biphenyl-3-carbonitrile (0.059 g, 0.125 mmol, 49%) as a dark foam. $^1$H NMR (300 MHz, CDCl$_3$): δ 7.98 (m, 1H), 7.92 (m, 1H), 7.74 (m, 1H), 7.64 (m, 3H), 7.58 (d, 2H), 7.45 (d, 2H), 7.11 (dd, 1H), 5.80 (m, 1H), 5.12 (m, 2H), 3.75 (m, 3H), 3.55 (m, 1H), 4.42 (m, 1H), 3.26 (m, 2H), 2.58 (dd, 2H).

Ozone was bubbled through a solution of 4'-{1-[3-(3,5-dichloro-phenyl)-2-oxoimidazolidin-1-ylmethyl]-but-3-enyl}-biphenyl-3-carbonitrile (0.059g, 0.124 mmol) in CH$_2$Cl$_2$ (15 mL) at −78° C. After 5 min, oxygen was bubbled through followed by the addition of DMS (0.1 mL, 12.5 mmol, 10 eq). The mixture was warmed to room temperature and stirred for 18 h. The solvent was removed by rotary evaporation and the resulting residue was dissolved in ClCH$_2$CH$_2$Cl (2 mL) and dimethylamine (2M in THF, 0.06 mL, 0.12 mmol, 1 eq) was added. The mixture was stirred at room temperature for 1 h and then Na(OAc)$_3$BH (0.033 g, 0.16 mmol, 1.3 eq) was added. The mixture was stirred at room temperature for 16 h and then partitioned between saturated aqueous NaHCO$_3$ (10 mL) and EtOAc (20 mL). The organic layer was washed with saturated aqueous NaCl, dried over Na$_2$SO$_4$, filtered and concentrated to yield the crude product. Purification by HPLC gave the title compound 4'-{1-[3-(3,5-dichlorophemyl)-2-oxo-imidazolidin-1-ylmethyl]-3-dimethylaminopropyl}-biphenyl-3-carbonitrile (0.016 g, 0.02 mmol, 16%) as a pale yellow oil. $^1$H NMR (300 MHz, CDCl$_3$): δ 7.96 (m, 1H), 7.92 (dt, 1H), 7.76 (dt, 1H), 7.68 (m, 3H), 7.56 (d, 2H), 7.46 (d, 2H), 7.14 (t, 1H), 3.82 (m, 3H), 3.44 (m, 3H), 3.4 (m, 2H), 2.94 (br s, 6H), 2.30 (m, 2H); MS(ESI): 507.1 (M+1), 509.0 (M+3).

EXAMPLE 33

(3,5-Dichloro-phenyl)-carbamic acid 3-dimethylamino-1-(4-pyridin-4-yl-phenyl)-propyl ester

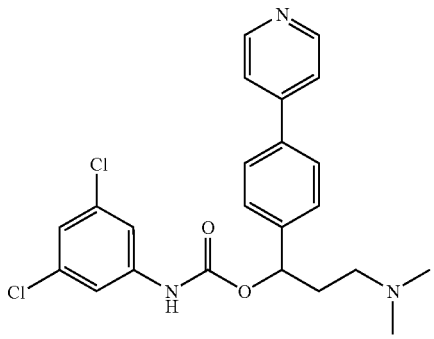

A mixture of 2-(4-iodo-phenyl)-pent-4-enenitrile (2.8 g, 9.9 mmol, intermediate for preparing EXAMPLE 2), OsO$_4$ (0.7 mL, 4% in water, 0.10 mmol), and NaIO$_4$ (4.44 g, 20.8 mmol) in 2:1 acetone/H$_2$O (100 mL) was stirred at room temperature for 16 h. TLC (1:1 hexanes/EtOAc) showed no starting material left. The mixture was diluted with H$_2$O (50 mL) and extracted with CH$_2$Cl$_2$ (50 mL×4). The organic layer was washed with brine, dried (Na$_2$SO$_4$) and concentrated by rotary evaporation. Purification by silica gel chromatography (1:1 hexanes/EtOAc) gave 2-(4-iodo-phenyl)-4-oxo-butyronitrile as a yellowish oil, 1.9 g (68%). $^1$H NMR (300 MHz, CDCl$_3$): δ 9.85 (s, 1H), 7.84 (d, 2H), 7.24 (d, 2H), 4.44 (t, 1H), 3.33 (dd, 1H), 3.14 (dd, 1H).

To a solution of 2-(4iodophenyl)-4oxobutyronitrile (2.03 g, 7.1 mmol) in ClCH$_2$CH$_2$Cl (50 mL) was added dimethylamine (14.3 mL, 2M in THF, 28.6 mmol, 4 eq) and the mixture was left stirring at room temperature for 1 h. Na(OAc)$_3$BH (6.04 g, 28.6 mmol, 4 eq) was added and the mixture was stirred at room temperature for 16 h. The reaction was quenched by adding aqueous saturated NaHCO$_3$ (50 mL) and the mixture was extracted with EtOAc (50 mL×3). The organic layer was washed with saturated aqueous NaCl, dried over Na$_2$SO$_4$ and concentrated. The crude product was purified by silica gel chromatography (50% EtOAc/hexanes) to give 4dimethylamino-2-(4iodophenyl)-butyronitrile as a dark brown solid, 2.09 g (94%). $^1$H NMR (300 MHz, CDCl$_3$): δ 7.83 (d, 2H), 7.22 (d, 2H), 4.10 (t, 1H), 2.56 (m, 1H), 2.41 (m, 1H), 2.34 (s, 6H), 2.20 (m, 1H), 2.05 (m, 1H).

To a solution of 4-dimethylamino-2-(4-iodo-phenyl)-butyronitrile (1.02 g, 3.2 mmol) in 2:1 toluene/EtOH (30 mL) was added 2M Na$_2$CO$_3$ (10 mL, 20 mmol), pyridine-4-boronic acid pinacol cyclic ester (1.0 g, 4.9 mmol), and Pd(PPh$_3$)$_4$ (116 mg, 0.31 mmol). The resulting mixture was heated at 90° C. under Ar for 16 h. TLC (10% MeOH/CH$_2$Cl$_2$) showed no starting material left. The mixture was diluted with EtOAc (100 mL), washed with saturated aqueous NaHCO$_3$ (50 mL×3), saturated aqueous NaCl (50 mL×3), dried over Na$_2$SO$_4$ and concentrated by rotary evaporation. The crude residue was purified using silica gel chromatography (2–10% MeOH/CH$_2$Cl$_2$ gradient) to give 4-dimethylamino-2-(4-pyridin-4-yl-phenyl)-butyronitrile as a brown oil, 680 mg (80%). $^1$H NMR (300 MHz, CDCl$_3$): δ 8.79 (dd, 2H), 7.78 (d, 2H), 7.60 (m, 4H), 4.22 (dd, 1H), 2.61 (m, 1H), 2.46 (m, 1H), 2.37 (s, 6H), 2.24 (m, 1H), 2.15 (m, 1H).

To a solution of 4-dimethylamino-2-(4-pyridin-4-yl-phenyl)-butyronitrile (680 mg, 2.56 mmol) in THF (5 mL) was added LiAlH$_4$ (1M in THF, 26 mL, 26 mmol) and the mixture was stirred at room temperature for 16 h. TLC (10% MeOH/CH$_2$Cl$_2$) showed no starting material left and a new low Rf spot was formed. The mixture was treated with 1.74 mL of H$_2$O, followed by 3.48 mL of 1N aqueous NaOH, and then 5.2 mL of H$_2$O. After 30 min of stirring, the mixture was filtered and the filtrate was dried over Na$_2$SO$_4$ and concentrated to give 3-dimethylamino-1-(4-pyridin-4-yl-phenyl)-propan-1-ol as a yellowish solid, 300 mg (46%). $^1$H NMR (300 MHz, CDCl$_3$): δ 8.75 (dd, 2H), 7.74 (m, 2H), 7.62 (m, 4H), 5.12 (dd, 1H), 2.82 (m, 1H), 2.64 (m, 1H), 2.44 (s, 6H), 1.97 (m, 2H).

To a solution of 3-dimethylamino-1-(4-pyridin-4-yl-phenyl)-propan-1-ol (100 mg, 0.37 mmol) in CH$_2$Cl$_2$ (2 mL) was added 3,5-dichloro-phenylisocyanate (70 mg, 0.37 mmol) and the mixture was stirred at room temperature for 16 h. The mixture was concentrated to give a light brown oil, which was then purified by silica gel chromatography (5–10% MeOH/DCM gradient) to afford the title compound (3,5-dichloro-phenyl)-carbamic acid 3-dimethylamino-1-(4-pyridin-4-yl-phenyl)-propyl ester as a white solid, 131 mg (91%). $^1$H NMR (300 MHz, CD$_3$OD): δ 8.77 (dd, 2H), 7.72 (d, 2H), 7.58 (m, 3H), 7.48 (d, 2H), 7.12 (t, 1H), 5.94 (m, 1H), 2.49 (m, 2H), 2.36 (s, 6H), 2.33 (m, 1H), 2.21 (m, 1H); MS(ESI): 444.1 (M+1), 446.1 (M+3).

Table I provides additional Examples (#34–457) of MCH active compounds that were prepared using the methods as described for Examples 20–33.

MCH Assay PCOP Protocol

A reaction mixture of 10 μg hMCHR-CHO overexpressing membranes (from Receptor Biology, Inc., Beltsville, Md., or internally produced) and 100 μg/well WGA-SPA beads (from Amersham Pharmacia Biotech, Inc., Piscataway, N.J.)/100 μl was prepared in MCHR assay buffer (25 mM HEPES, pH 7.4, 10 mM NaCl, 10 mM $MgCl_2$, 5 mM $MnCl_2$, 0.1% BSA). A 2.0 nM stock of ligand, [$^{125}$I]-MCH (from Perkin Elmer Life Sciences, Inc., Boston, Mass.) was prepared in the MCHR assay buffer. 40×stock solutions of test compounds were prepared in DMSO and then added to a 96well assay plate (Corning #3604, Corning, N.Y.) as follows: 5 μl test compound, test compound or DMSO, 45 μl MCHR assay buffer, 100 -μl of reaction mixture, 50 μl of ligand stock (Final [Ligand]=0.5 nM). The assay plates were shaken for 5 minutes on a plate shaker, then incubated for 2 hours before cpm/well were determined in a Microbeta Trilux counter (from PerkinElmer Wallac, Inc., Gaithersburg, Md.). Percent inhibition of total binding-non-specific binding (2.5 μM MCH) was determined for $IC_{50}$ values.

TABLE I

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 20 | 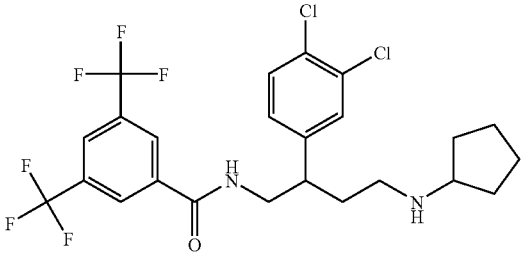 | 540.1169 | 541.1, 543.1 | C |
| 21 | 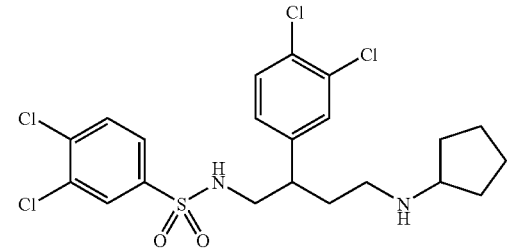 | 508.0312 | 509.1, 511.0, 513.0 | C |
| 22 | 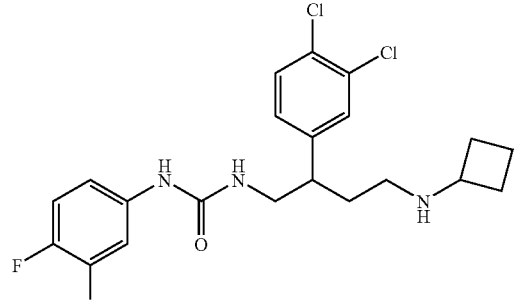 | 468.1131 | 469.0, 471.0 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 23 | 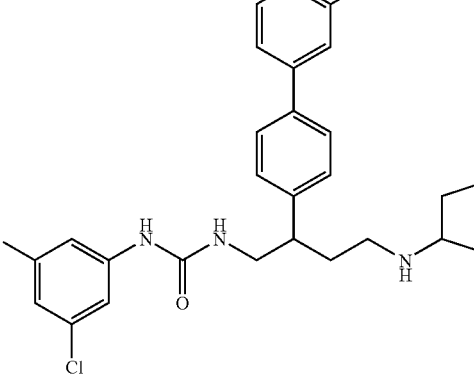 | 520.1796 | 521.0, 523.0 | C |
| 24 | 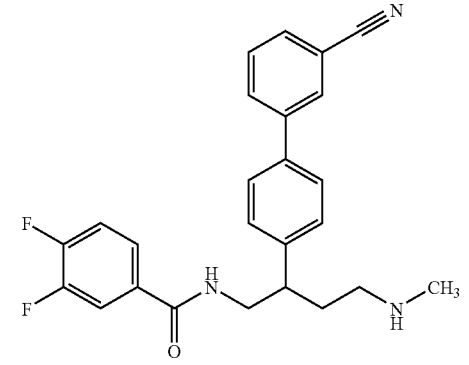 | 419.1809 | 420.1, 421.1 | C |
| 25 | 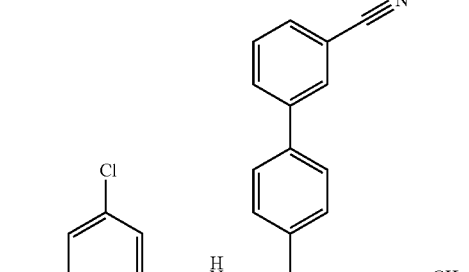 | 501.1044 | 502.1, 504.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 26 | 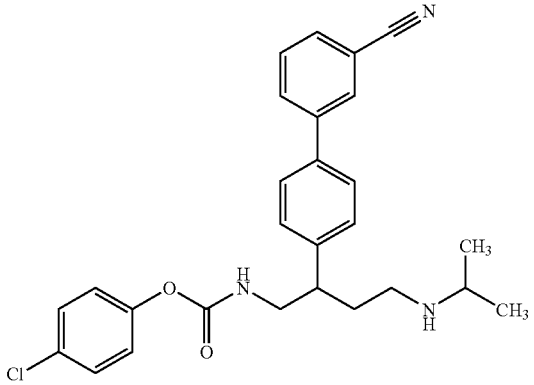 | 461.1870 | 462.2 | C |
| 27 | 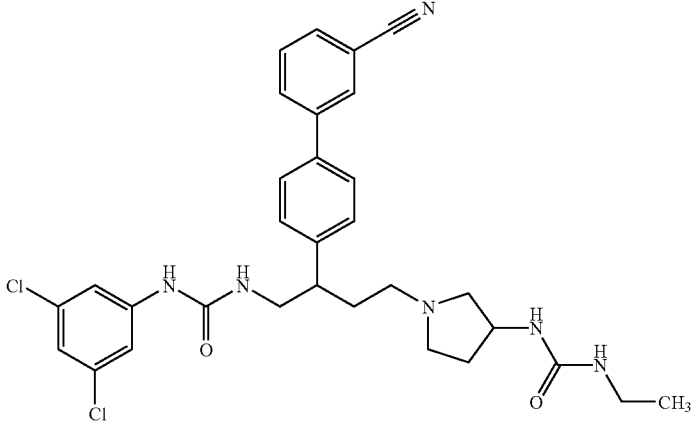 | 592.2120 | 593.1, 595.1 | C |
| 28 | 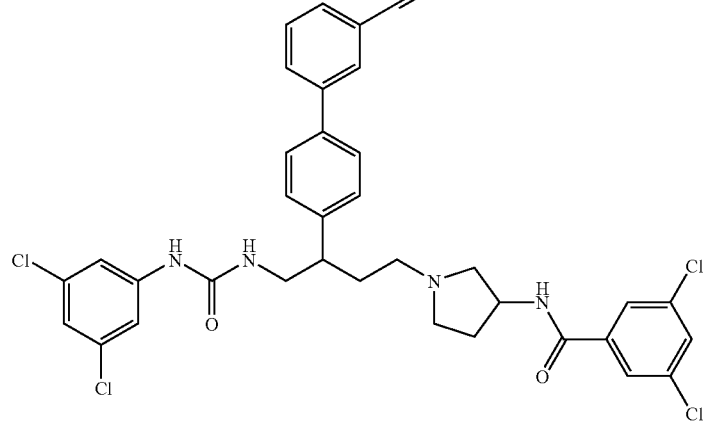 | 693.1231 | 693.9, 695.9, 697.9 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 29 | | 613.1681 | 614.1, 616.1 | C |
| 30 | | 568.1482 | 569.1, 571.2 | C |
| 31 | | 437.1061 | 438.0, 440.0 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 32 | | 506.1640 | 507.1, 509.0 | C |
| 33 | | 443.1167 | 444.1, 446.1 | C |
| 34 | | 496.1796 | 497.1, 499.1 | A |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 35 | 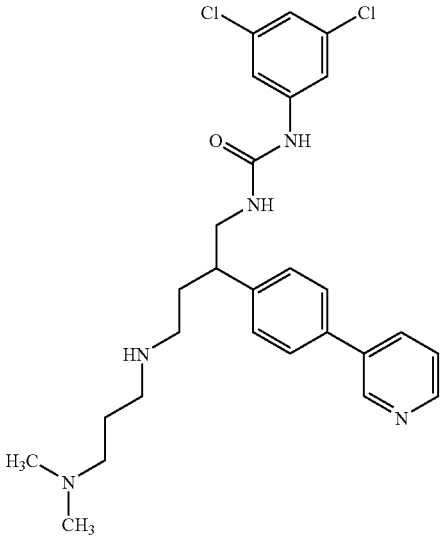 | 513.2062 | 514.1, 516.0 | A |
| 36 | 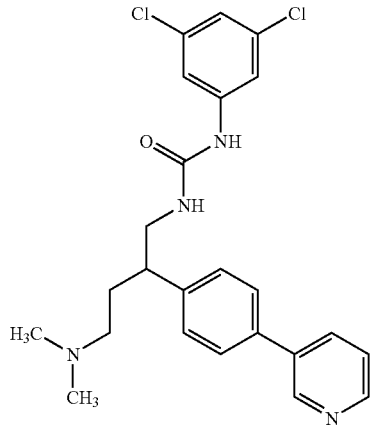 | 456.1483 | 457.2, 459.2 | A |
| 37 | 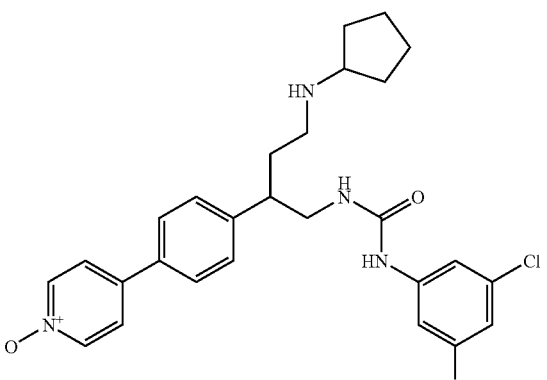 | 512.1745 | 513.2, 515.3 | A |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 38 | 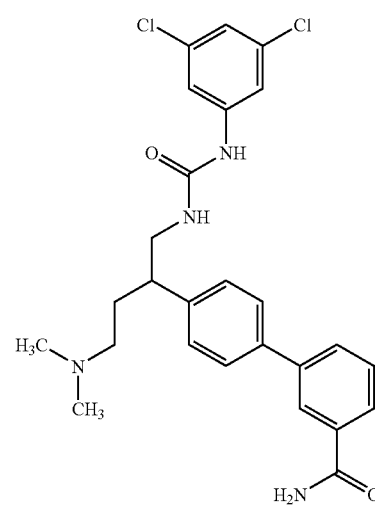 | 498.1589 | 499.2, 501.1 | A |
| 39 | 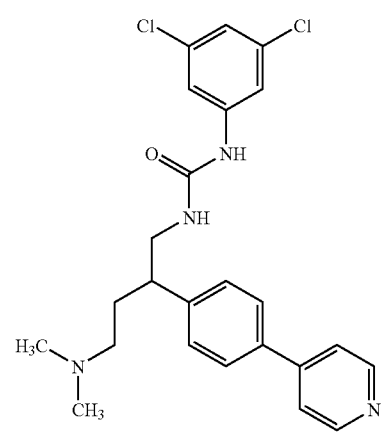 | 456.1483 | 457.2, 459.2 | B |
| 40 | 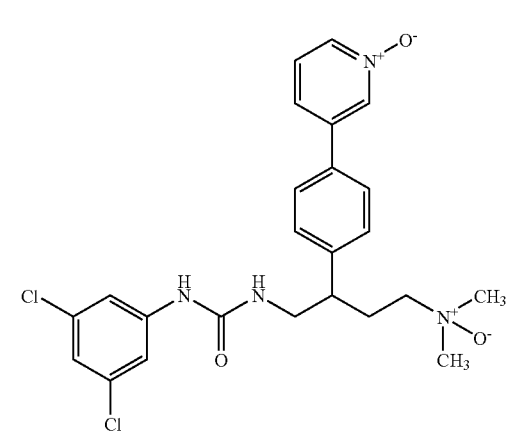 | 488.1382 | 489.1, 491.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 41 | | 488.1382 | 489.1, 491.1 | C |
| 42 | | 443.1167 | 444.1, 446.1 | C |
| 43 | | 458.1873 | 459.0, 461.1 | A |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 44 | | 434.1918 | 435.0, 436.1 | A |
| 45 | | 432.1717 | 432.9, 435.0 | A |

US 7,034,056 B2
73 74
TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 46 | 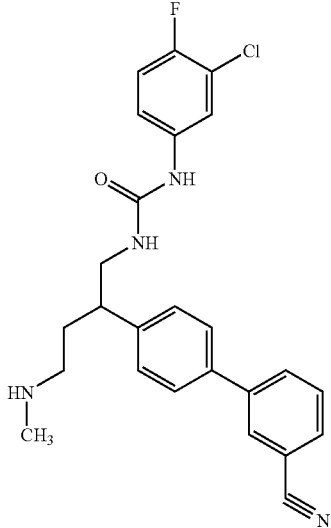 | 450.1622 | 451.0, 453.0 | A |
| 47 | 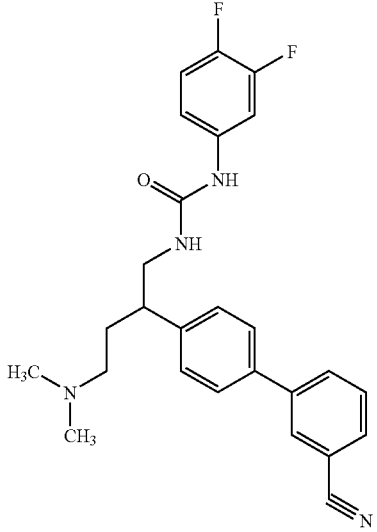 | 448.2074 | 449.1, 450.2 | A |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 48 | | 448.2074 | 449.1, 450.0 | A |
| 49 | | 416.2012 | 417.0, 418.1 | A |
| 50 | | 464.1779 | 465.0 | A |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 51 | 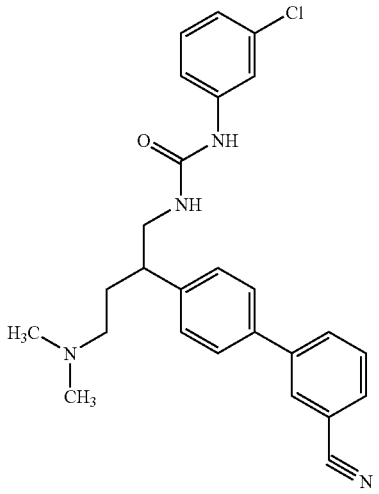 | 446.1873 | 447.1, 449.1 | A |
| 52 | 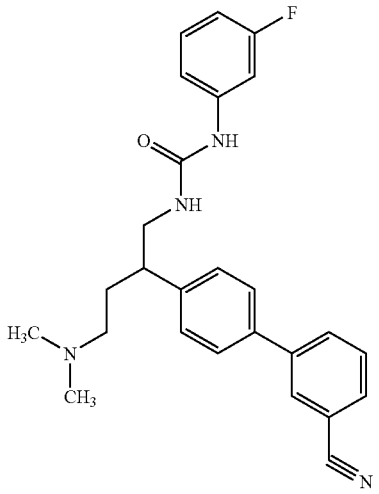 | 430.2169 | 431.1, 432.1 | A |
| 53 | 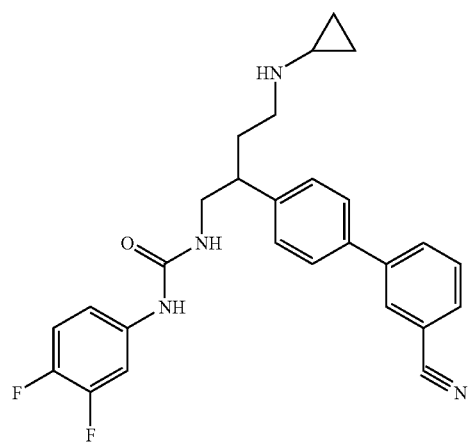 | 460.2074 | 461.0, 462.1 | A |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 54 | 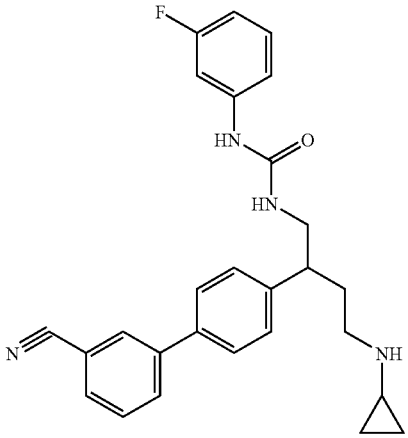 | 442.2169 | 443.1 | A |
| 55 | 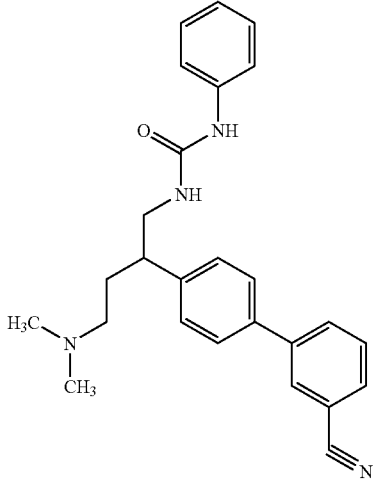 | 412.2263 | 413.1, 414.1 | A |
| 56 | 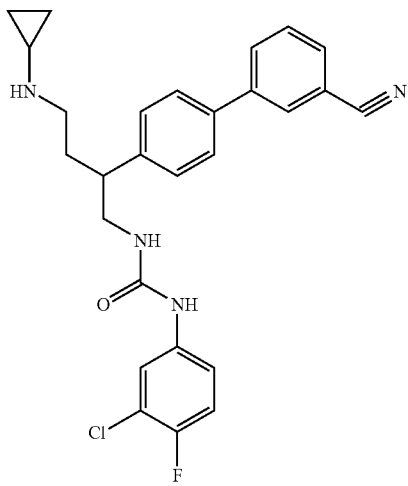 | 476.1779 | 477.0, 479.1 | A |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 57 | 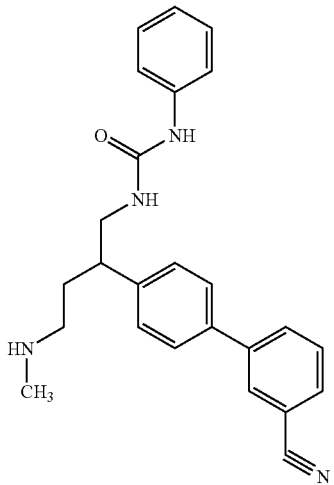 | 398.2106 | 399.0, 400.0 | A |
| 58 | 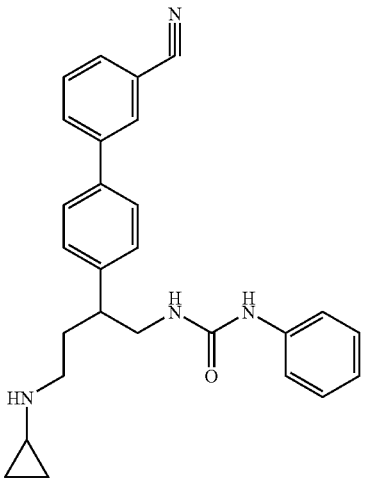 | 424.2263 | 425.0, 426.2 | A |
| 59 | 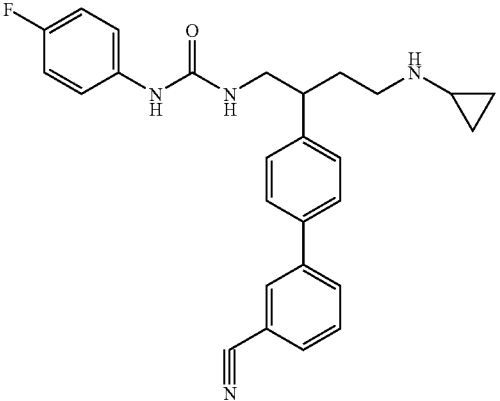 | 442.2169 | 443.0, 444.1 | A |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 60 | | 416.2012 | 417.0, 418.1 | A |
| 61 | | 430.2169 | 431.1, 432.1 | A |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 62 | 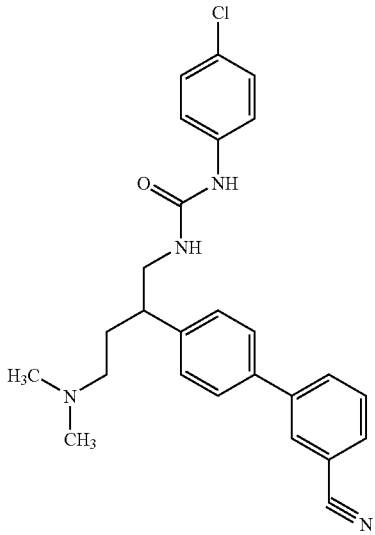 | 446.1873 | 447.1, 449.1 | A |
| 63 | 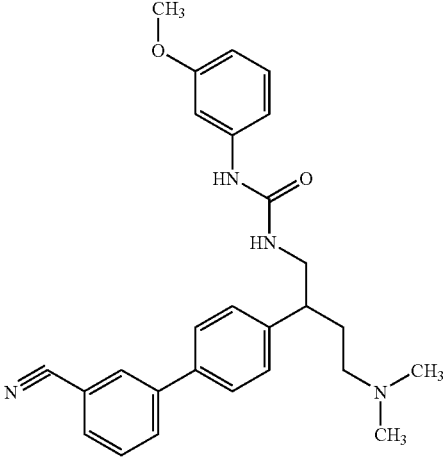 | 442.2369 | 443.1 | A |
| 64 | 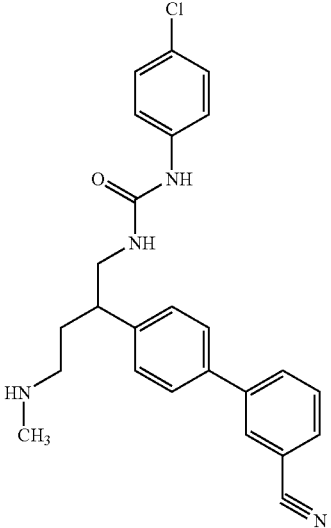 | 432.1717 | 433.0, 434.0 | A |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 65 | 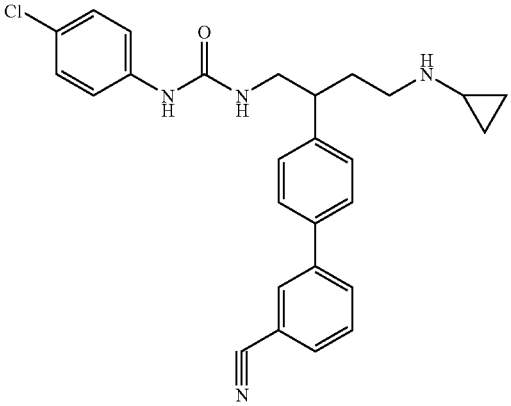 | 458.1873 | 459.1, 461.0 | A |
| 66 | 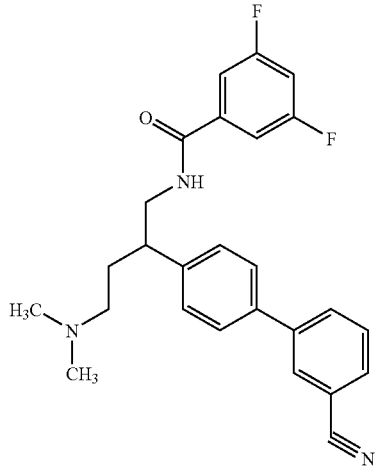 | 433.1965 | 434.1, 335.2 | A |
| 67 | 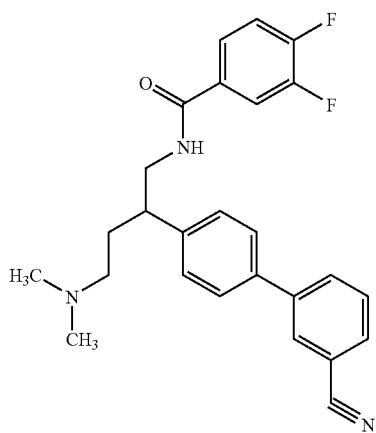 | 433.1965 | 434.1, 435.1 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 68 | | 445.1965 | 446.1, 447.1 | B |
| 69 | | 445.1965 | 446.1, 447.1 | B |
| 70 | | 419.1809 | 420.1, 421.1 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 71 | 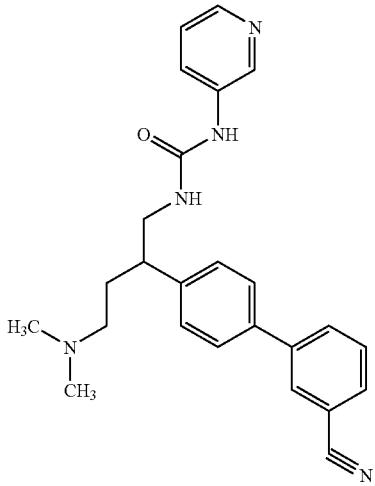 | 413.2215 | 414.0 | B |
| 72 | 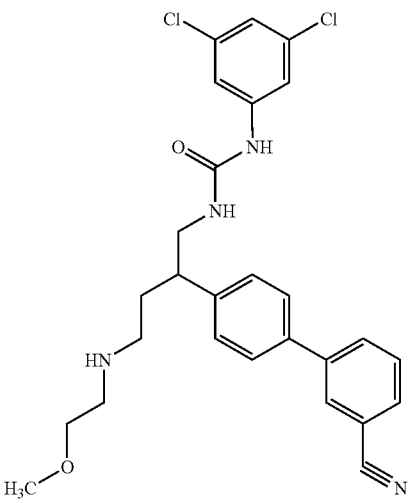 | 510.1589 | 511.1, 513.0 | A |
| 73 | 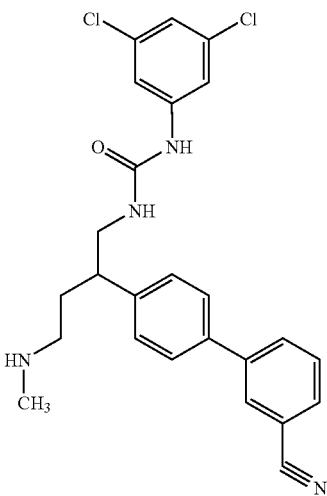 | 466.1327 | 467.4, 469.1 | A |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 74 | 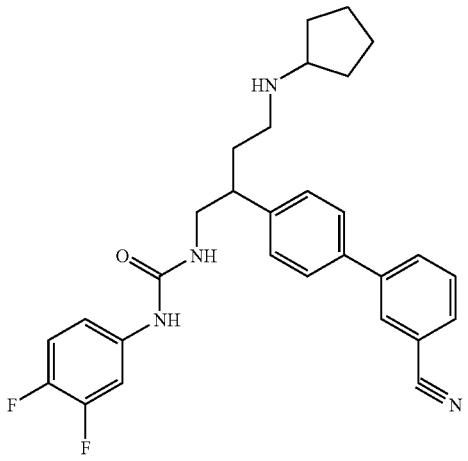 | 488.2387 | 489.1, 490.1 | A |
| 75 | 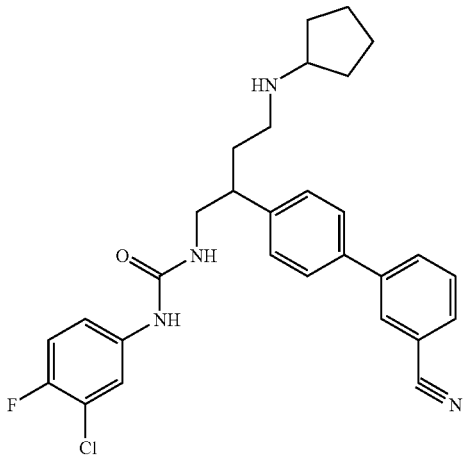 | 504.2092 | 505.1, 507.1 | A |
| 76 | 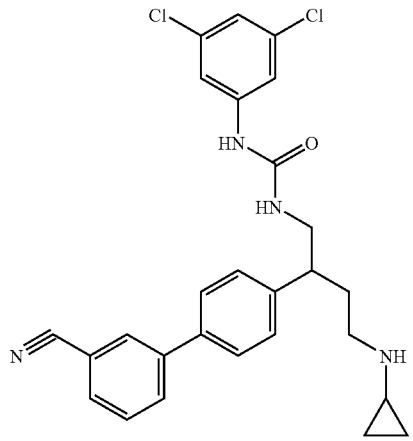 | 492.1483 | 493.0, 494.0, 495.0, 496.0 | A |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 77 | 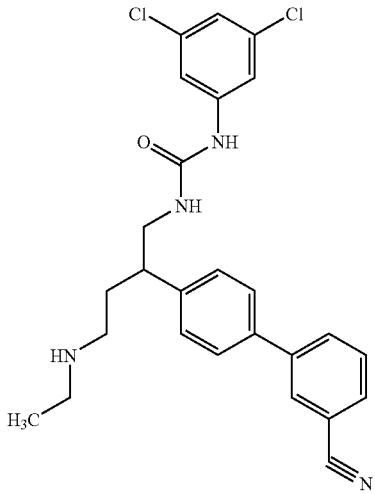 | 480.1483 | 481.0, 483.0 | A |
| 78 | 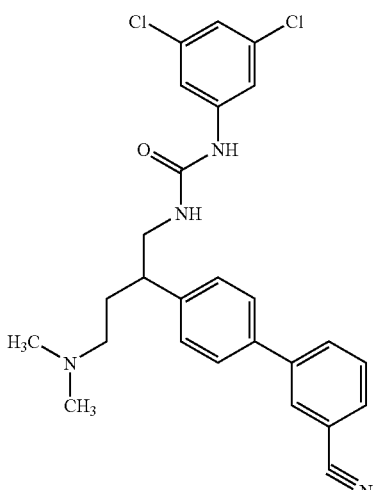 | 480.1483 | 481.1, 483.1 | A |
| 79 | 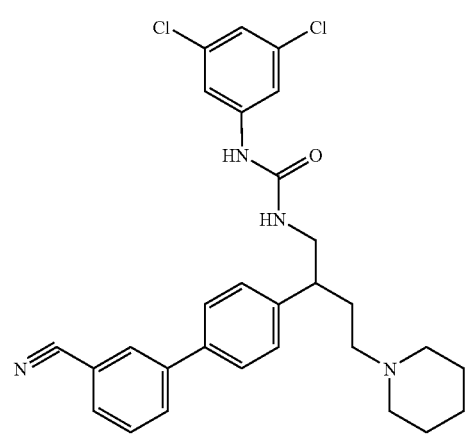 | 520.1796 | 521.1, 523.1 | A |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 80 | 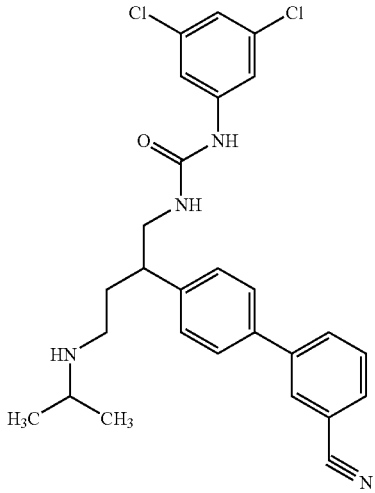 | 494.1640 | 495.0, 497.1 | A |
| 81 | 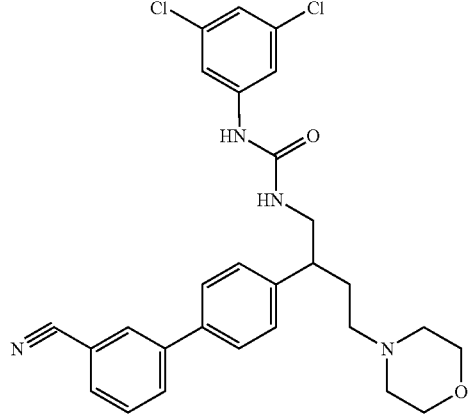 | 522.1589 | 523.1, 525.1 | A |
| 82 | 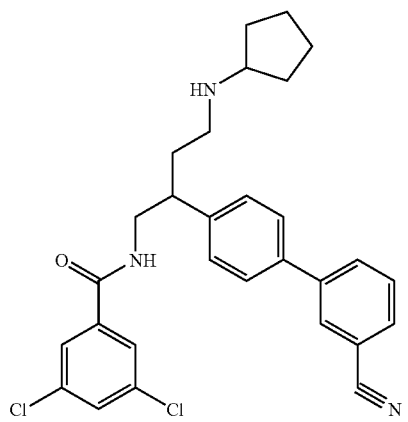 | 505.1687 | 506.1, 508.1 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 83 | | 473.2278 | 474.1, 475.2 | B |
| 84 | | 455.2373 | 456.1, 457.2 | B |
| 85 | | 471.2077 | 472.1, 473.1 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 86 | | 558.1259 | 558.9, 560.8 | B |
| 87 | | 598.1572 | 598.9, 601.0 | C |
| 88 | | 596.1932 | 597.1, 599.0 | A |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 89 | 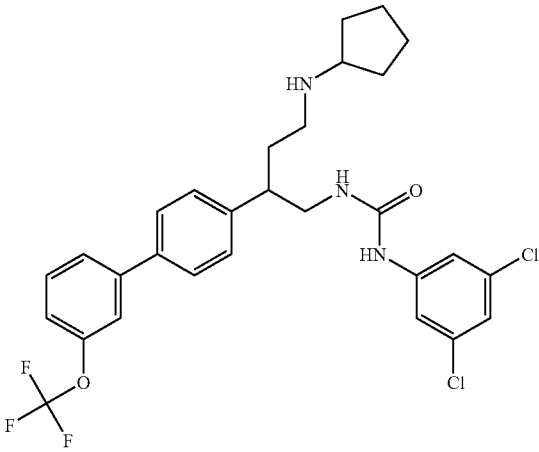 | 579.1667 | 579.9, 582.1 | A |
| 90 | 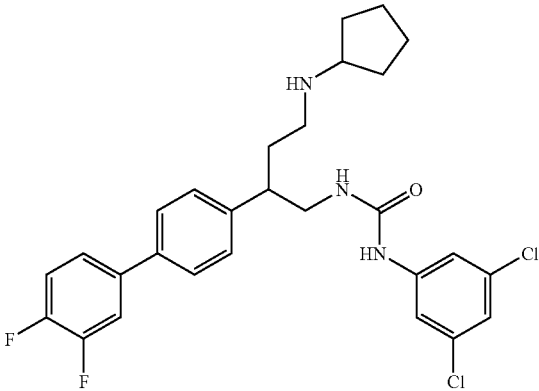 | 531.1655 | 532.0, 534.1 | A |
| 91 | 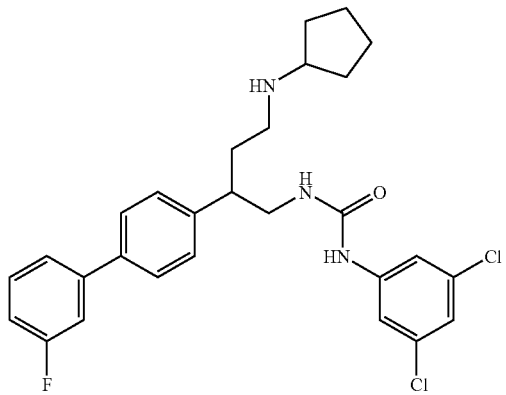 | 513.1750 | 514.1, 516.0 | A |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 92 | 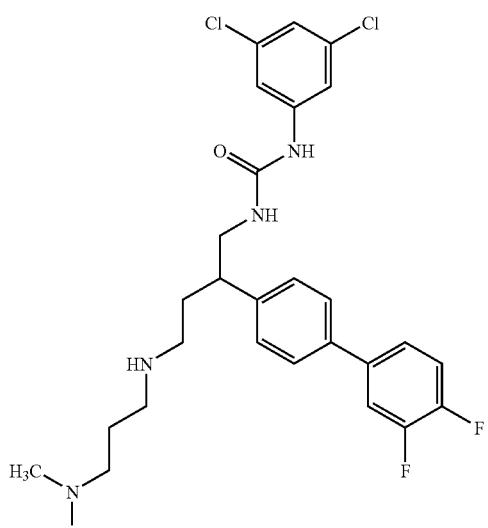 | 548.1921 | 549.0, 551.1 | A |
| 93 | 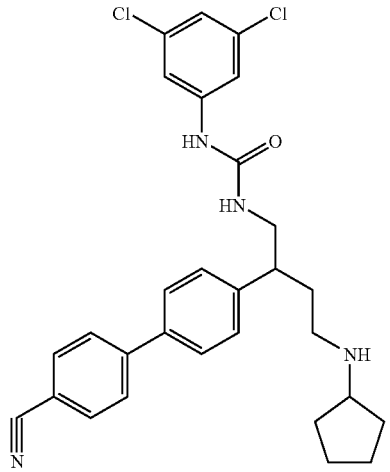 | 520.1796 | 521.0, 523.1 | A |
| 94 | 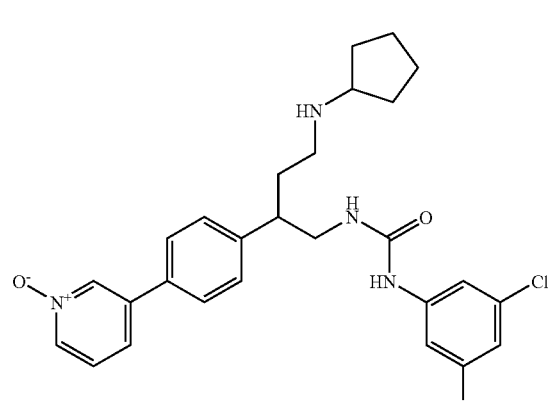 | 512.1745 | 513.0, 515.1 | A |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 95 | 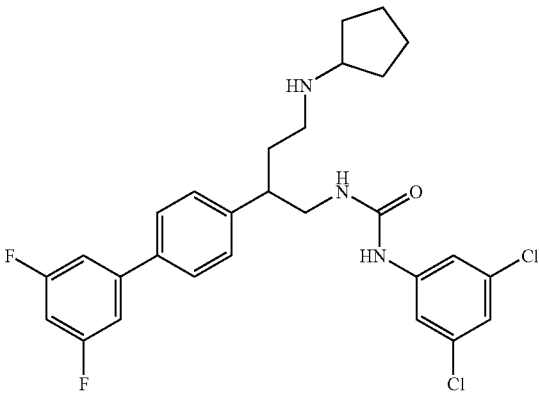 | 531.1655 | 532.0, 534.1 | A |
| 96 | 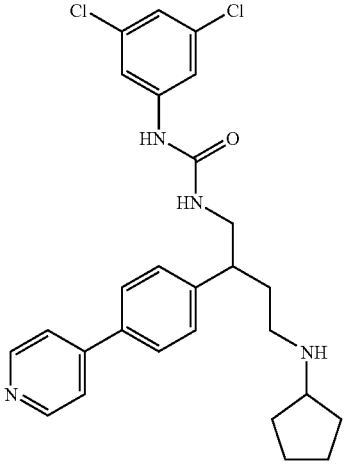 | 496.1796 | 497.3, 499.3 | B |
| 97 | 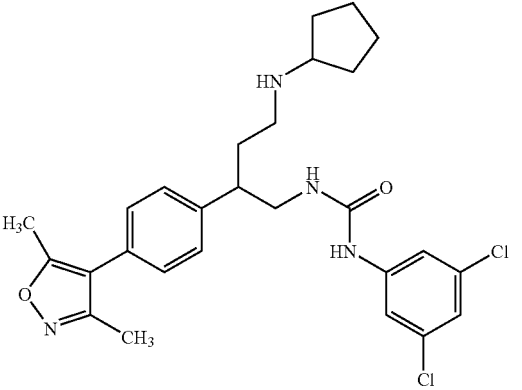 | 514.1902 | 515.0, 517.3 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 98 | 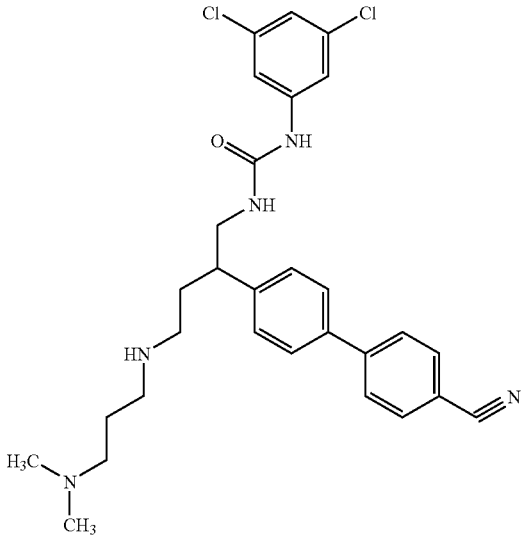 | 537.2062 | 538.1, 540.1 | B |
| 99 | 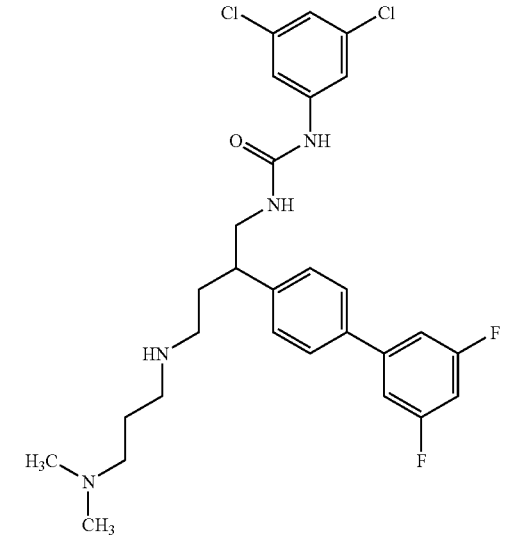 | 548.1921 | 549.0, 551.1 | B |
| 100 | 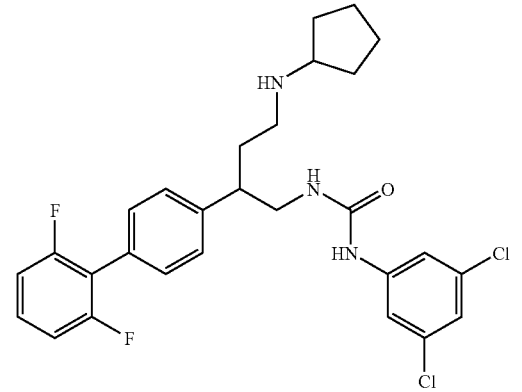 | 531.1655 | 532.0, 534.0 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 101 | 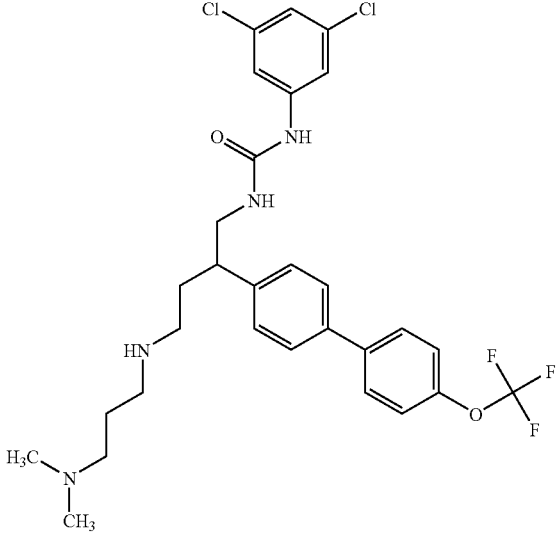 | 596.1932 | 597.0, 599.2 | B |
| 102 | 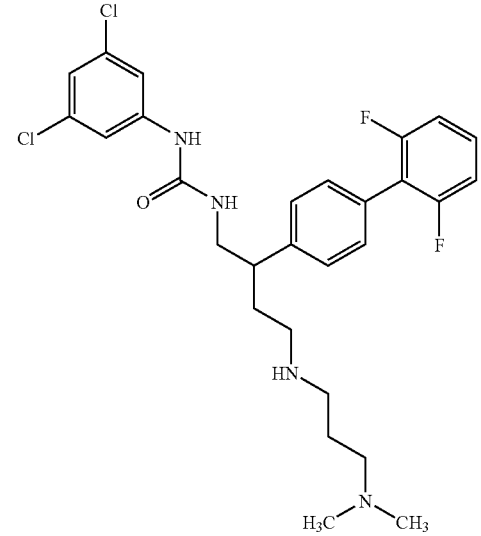 | 548.1921 | 549.0, 551.1 | C |
| 103 | 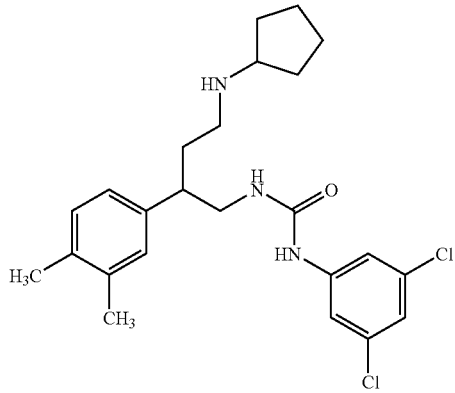 | 447.1844 | 448.1, 450.1 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 104 | | 474.1670 | 475.1, 477.0 | B |
| 105 | | 512.1148 | 513.0, 515.1, 517.1 | B |
| 106 | | 463.1429 | 464.1, 466.0 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 107 | 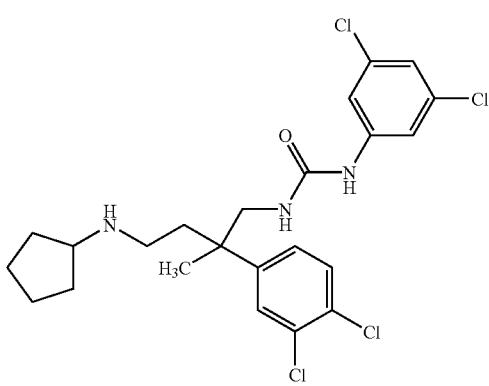 | 501.0908 | 502.0, 503.9, 505.1 | B |
| 108 | 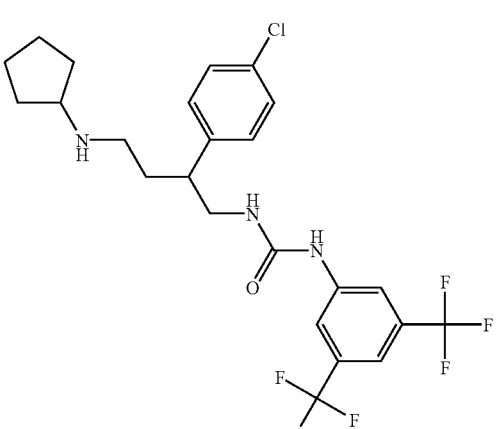 | 521.1668 | 522.1, 523.0 | B |
| 109 | 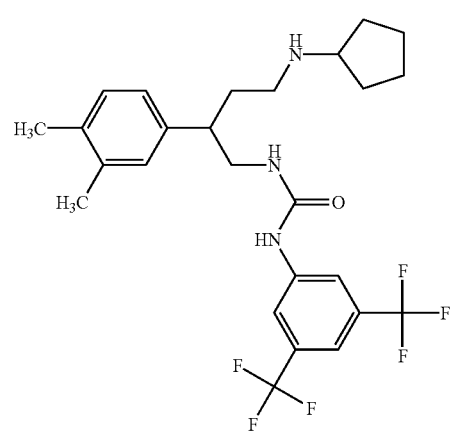 | 515.2371 | 516.1 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 110 | 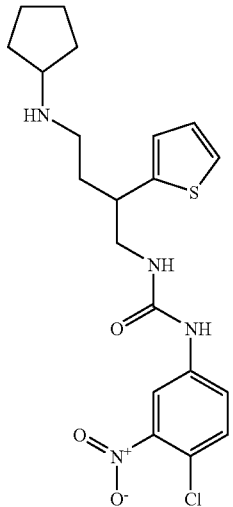 | 436.1336 | 437.0, 439.0 | B |
| 111 | 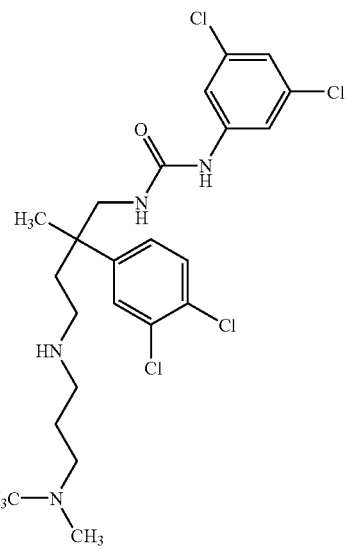 | 518.1173 | 518.9, 520.9, 523.0 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 112 | 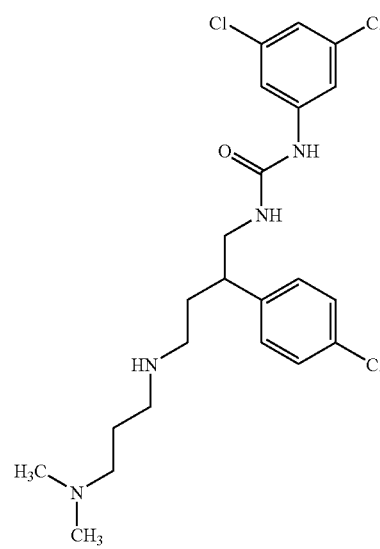 | 470.1407 | 470.9, 472.9 | C |
| 113 | 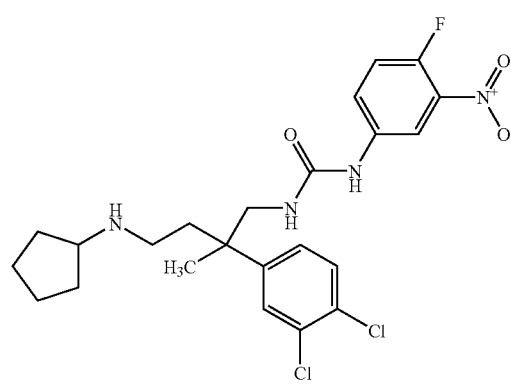 | 496.1444 | 497.0, 499.0 | C |
| 114 | 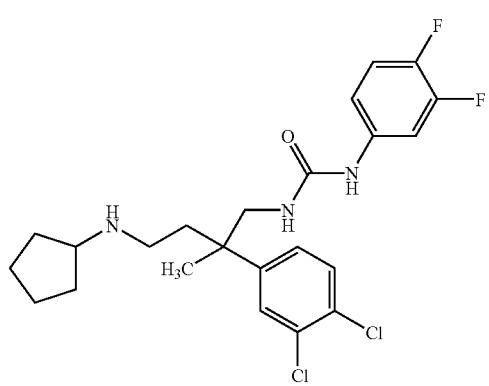 | 469.1499 | 470.0, 472.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 115 | 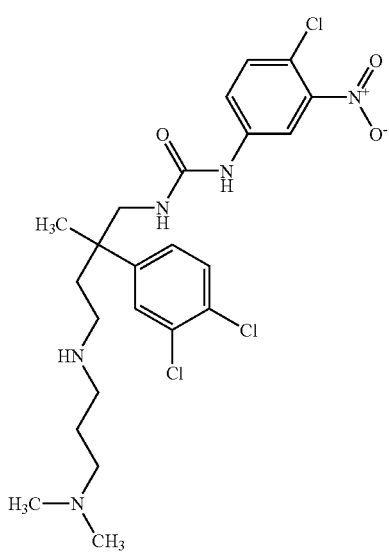 | 529.1414 | 530.0, 532.1 | C |
| 116 | 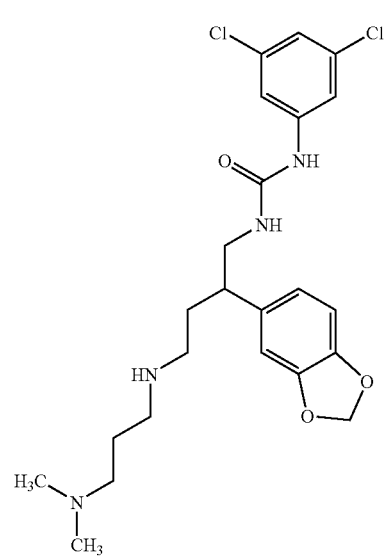 | 480.1695 | 481.0, 483.0 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 117 | 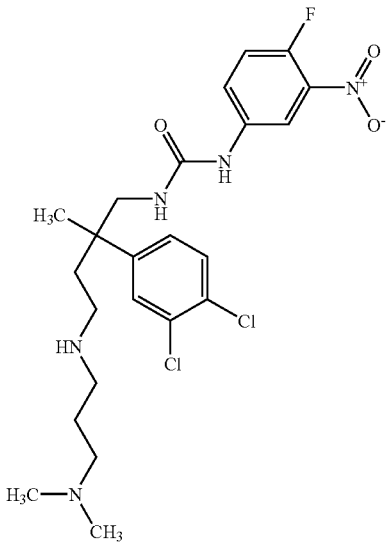 | 513.1709 | 514.0, 516.0 | C |
| 118 | 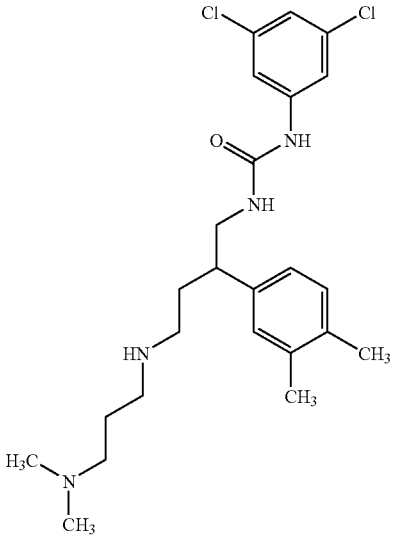 | 464.2109 | 465.1, 467.0 | C |

125
126
TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 119 | 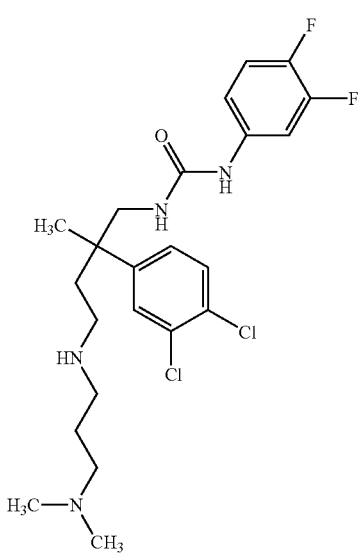 | 486.1764 | 487.1, 489.0 | C |
| 120 | 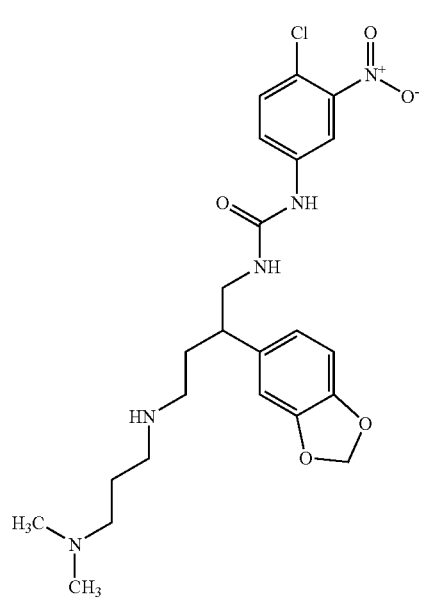 | 491.1935 | 492.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 121 | | 458.1965 | 459.1 | C |
| 122 | | 540.1461 | 541.0, 543.0, 545.1 | B |
| 123 | | 520.2008 | 521.1, 523.0 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 124 | 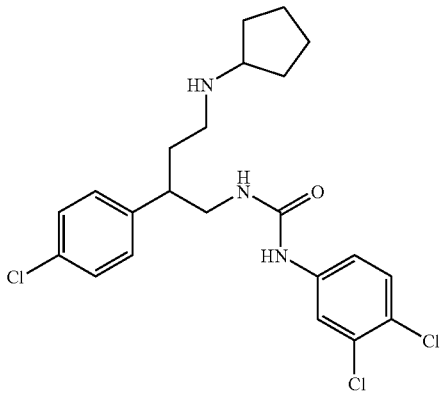 | 453.1141 | 454.0, 456.0 | B |
| 125 | 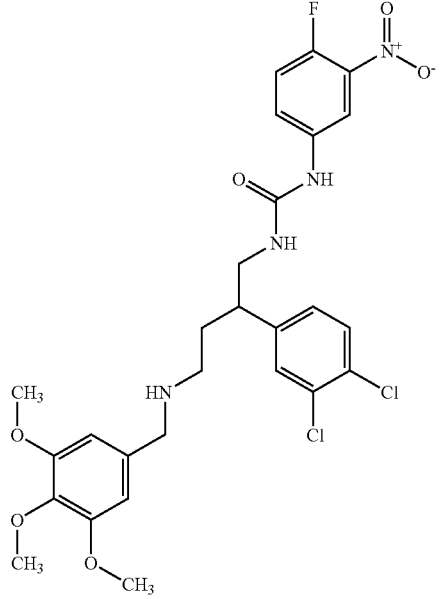 | 594.1448 | 594.8, 596.8, 597.9 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 126 | 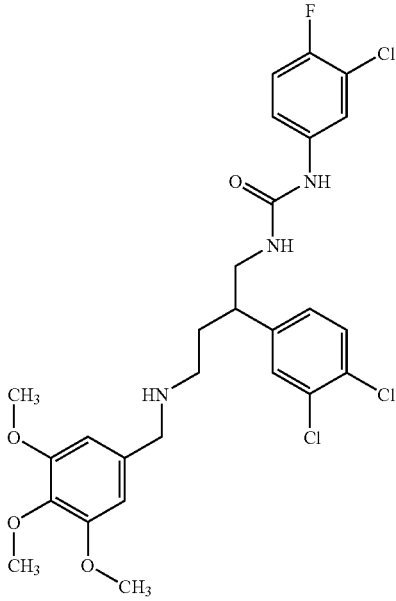 | 583.1207 | 583.8, 585.8, 587.1 | B |
| 127 | 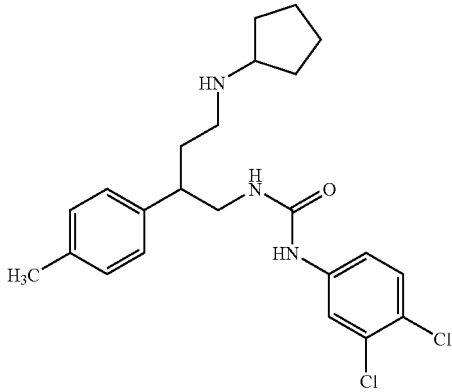 | 433.1687 | 434.1, 436.1, 438.0 | B |
| 128 | 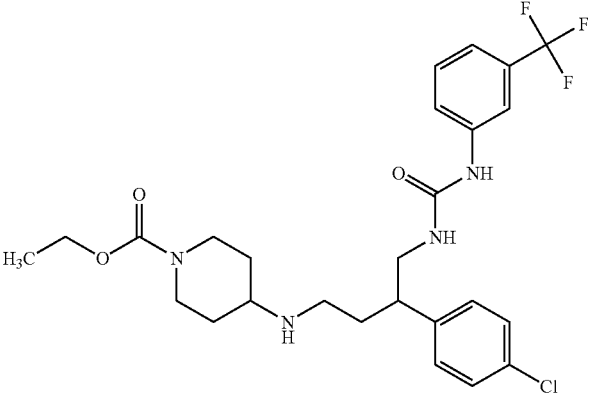 | 540.2115 | 541.0, 543.1, 544.1 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 129 | 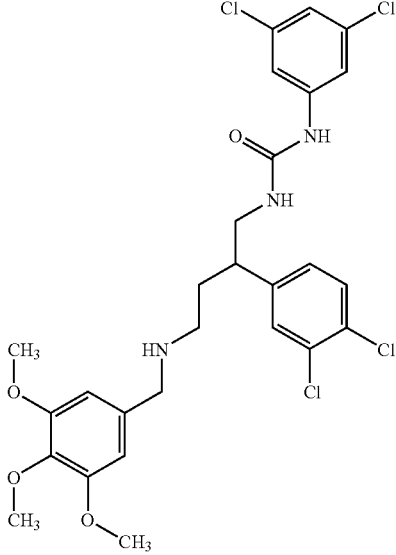 | 599.0912 | 599.8, 601.8, 603.8 | B |
| 130 | 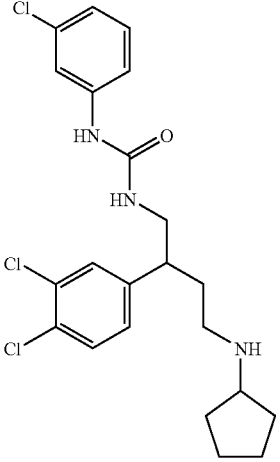 | 453.1141 | 454.0, 455.9, 458.0 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 131 | | 567.1503 | 567.8, 569.9, 570.9 | B |
| 132 | | 599.1565 | 599.8, 601.9, 602.9 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 133 | 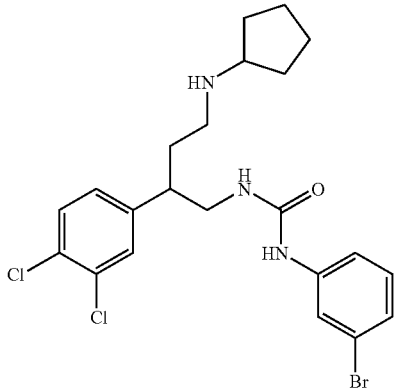 | 497.0636 | 497.9, 499.9, 502.0 | B |
| 134 | 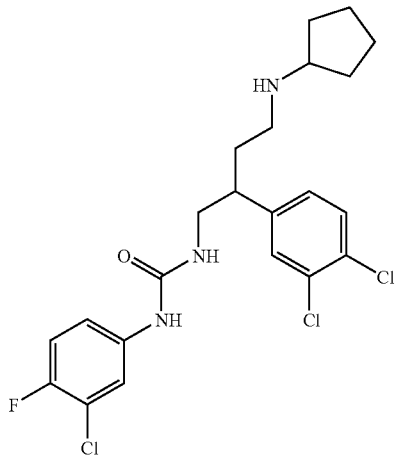 | 471.1047 | 472.0, 475.0, 476.0 | B |
| 135 | 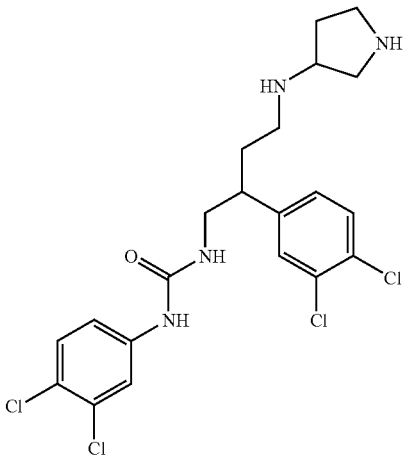 | 488.0704 | 488.9, 490.9, 493.0 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 136 | | 463.1025 | 464.0, 466.0, 468.1 | B |
| 137 | | 520.2661 | 521.1, 522.2 | B |
| 138 | | 534.1236 | 535.0, 537.0 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 139 | | 419.1531 | 420.0, 421.9, 423.1 | C |
| 140 | | 507.1292 | 508.0, 510.0, 511.1 | C |
| 141 | | 482.1287 | 483.0, 485.0 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 142 | 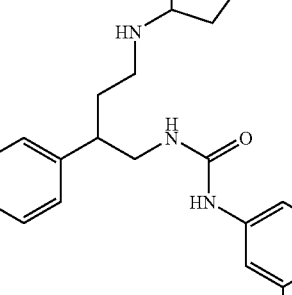 | 399.2077 | 400.0, 402.1 | C |
| 143 | 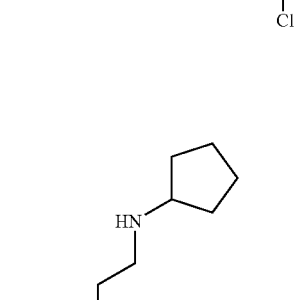 | 443.1572 | 444.1, 447.0 | C |
| 144 | 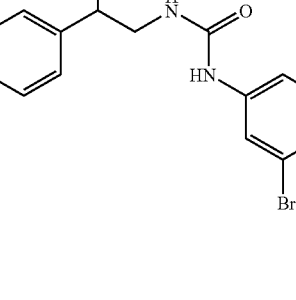 | 455.1342 | 456.0, 458.0 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 145 | 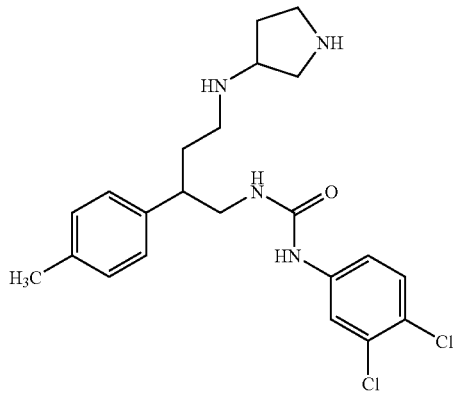 | 434.1640 | 435.0, 437.0 | C |
| 146 | 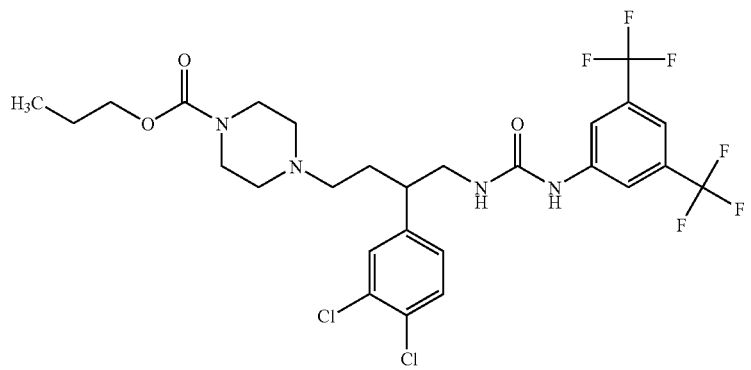 | 642.1599 | 643.0 | B |
| 147 | 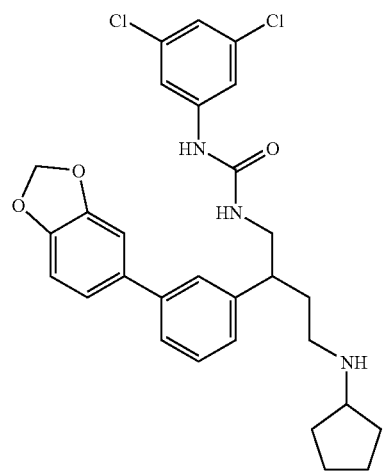 | 539.1742 | 540.1, 542.0 | B |

//
TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 148 | 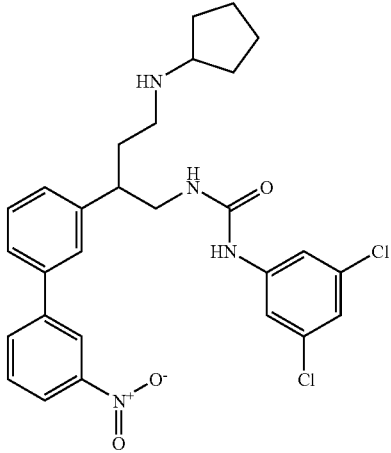 | 540.1695 | 541.0, 543.2 | B |
| 149 | 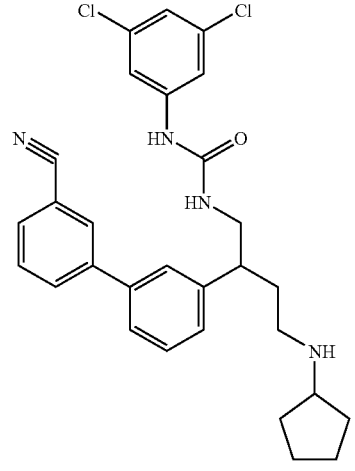 | 520.1796 | 521.0, 523.1 | B |
| 150 | 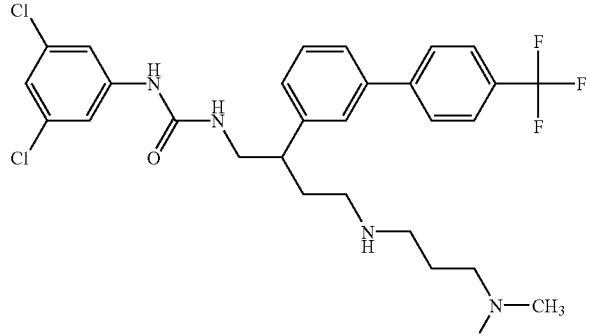 | 580.1983 | 581.1, 583.0 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 151 | 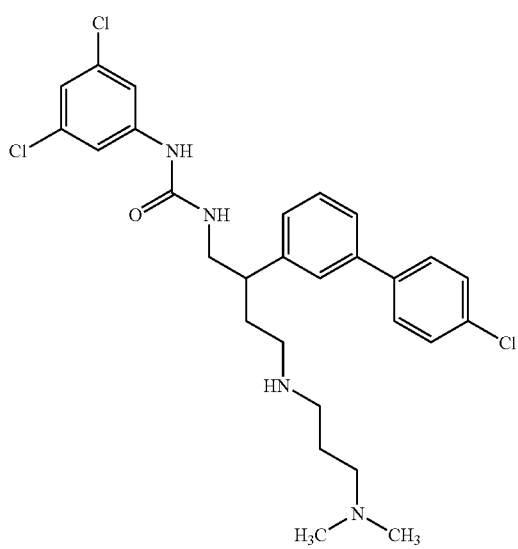 | 546.1720 | 547.0, 549.0 | B |
| 152 | 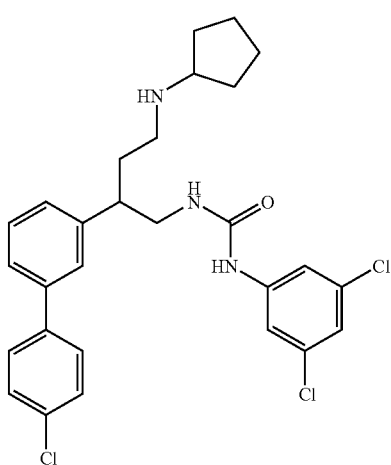 | 529.1454 | 530.0, 532.0 | B |
| 153 | 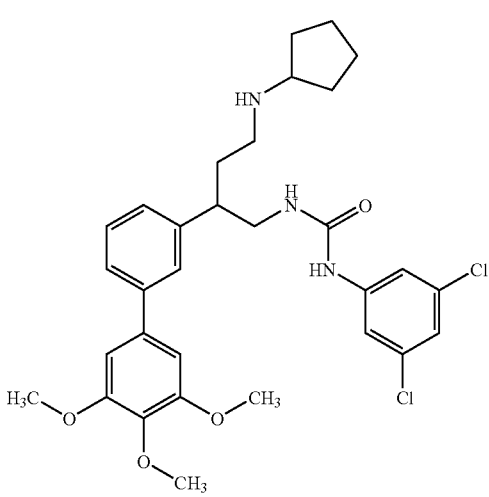 | 585.2161 | 586.0, 588.0 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 154 | 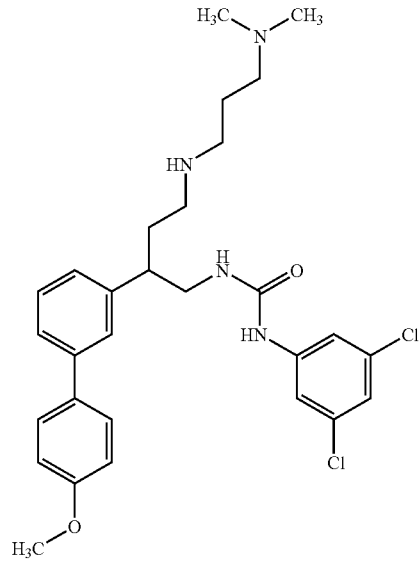 | 542.2215 | 543.1, 545.1 | B |
| 155 | 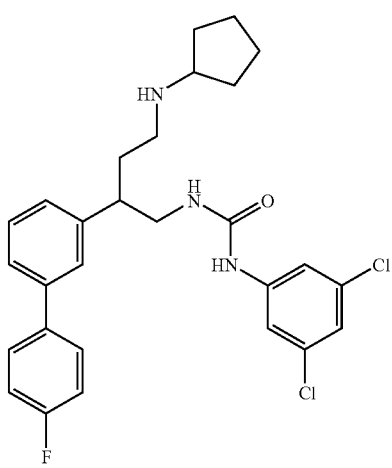 | 513.1750 | 514.1, 516.0 | B |
| 156 | 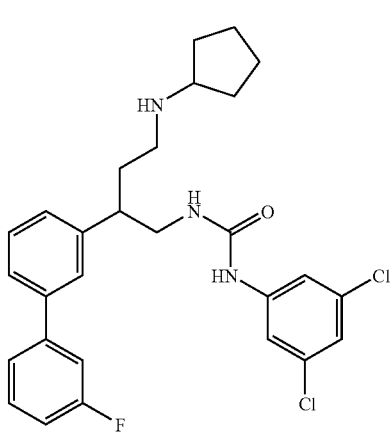 | 513.1750 | 514.0, 516.1 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 157 | 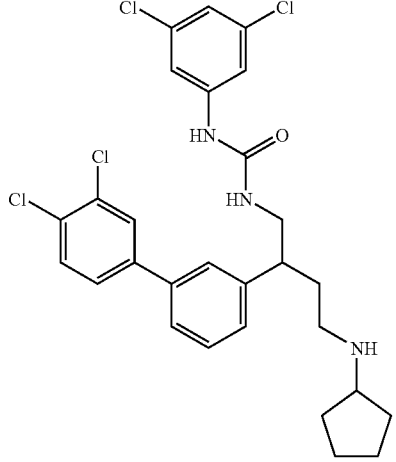 | 563.1064 | 564.1, 566.0, 568.0 | B |
| 158 | 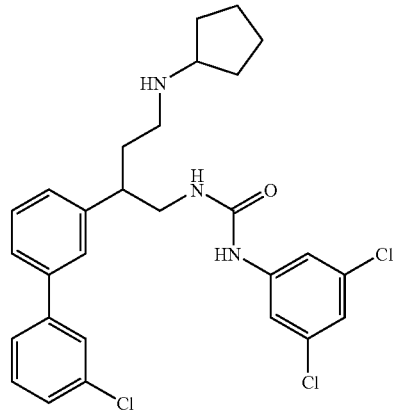 | 529.1454 | 530.0, 532.0 | B |
| 159 | 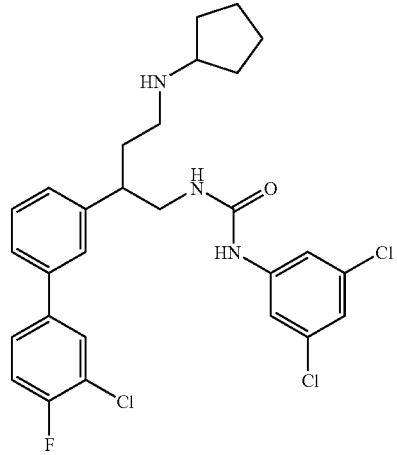 | 547.1360 | 548.0, 550.1 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 160 | | 459.1844 | 460.1, 462.2 | B |
| 161 | | 509.2000 | 510.0, 512.1, 514.1 | C |
| 162 | | 526.2266 | 527.0, 529.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 163 | | 556.2008 | 557.1, 559.1 | C |
| 164 | | 525.1950 | 526.1, 528.1 | C |
| 165 | | 530.2015 | 531.0, 533.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 166 | 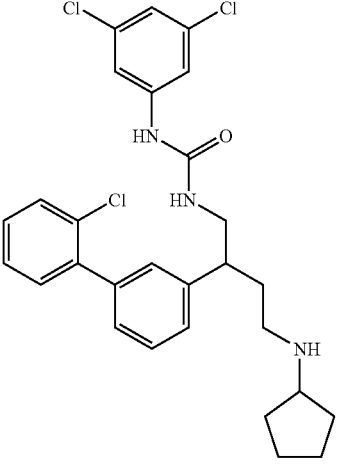 | 529.1454 | 530.0, 532.0 | C |
| 167 | 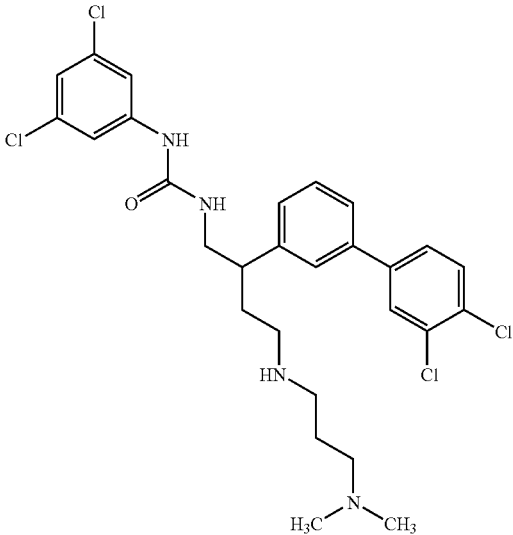 | 580.1330 | 581.0, 582.9, 585.0 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 168 | | 569.2324 | 570.1, 572.2 | C |
| 169 | | 537.2062 | 538.1, 540.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 170 | 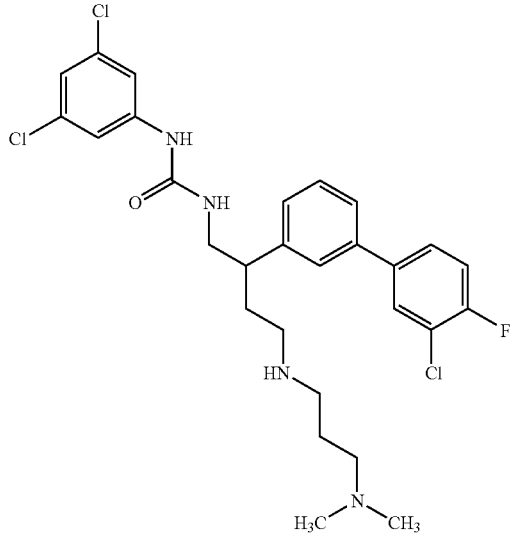 | 564.1625 | 565.0, 567.0 | C |
| 171 | 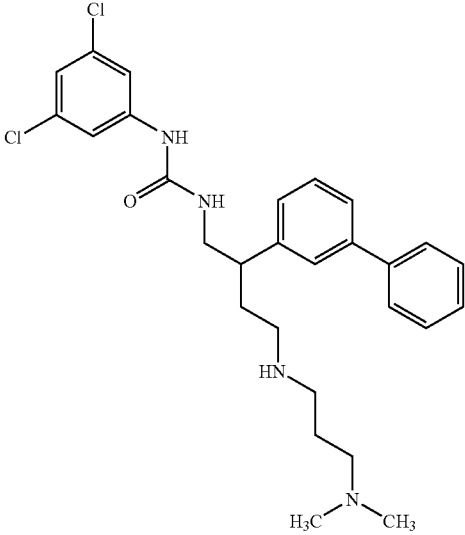 | 512.2109 | 513.1, 515.0 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 172 | 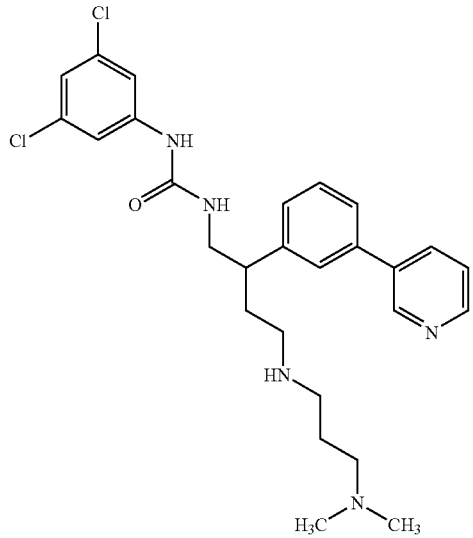 | 513.2062 | 514.0, 516.2 | C |
| 173 | 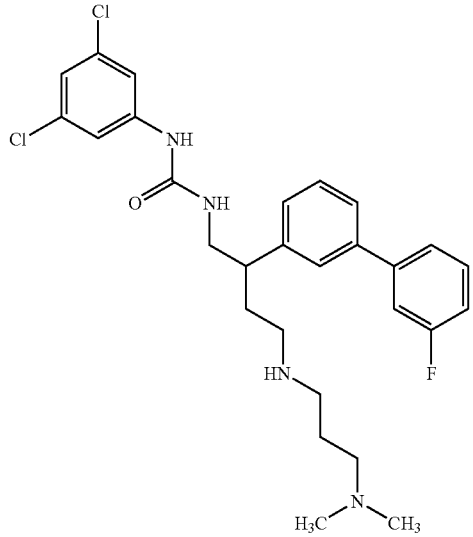 | 530.2015 | 531.1, 533.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 174 | 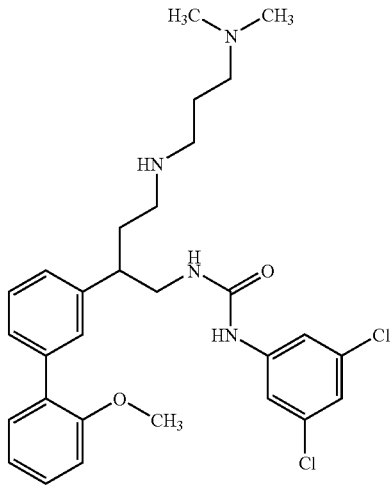 | 542.2215 | 543.1, 545.1 | C |
| 175 | 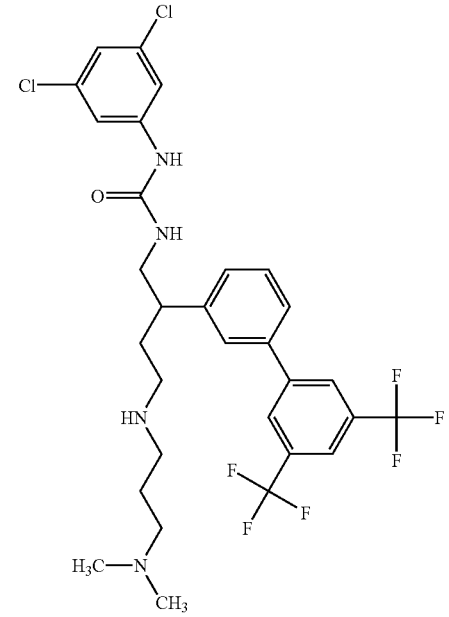 | 648.1857 | 649.0, 651.0 | C |
| 176 | 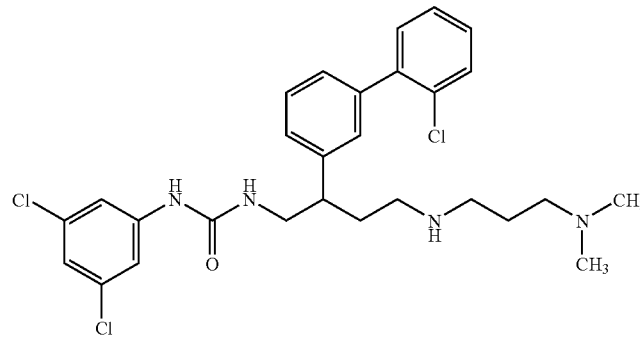 | 546.1720 | 547.0, 549.0 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 177 | 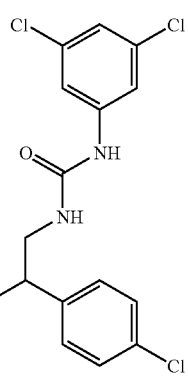 | 525.1465 | 525.9, 527.9, 530.0 | B |
| 178 | 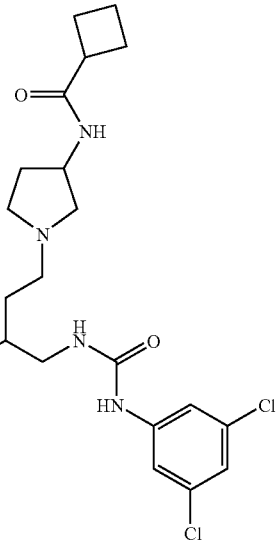 | 536.1512 | 537.1, 539.1, 541.2 | B |
| 179 | 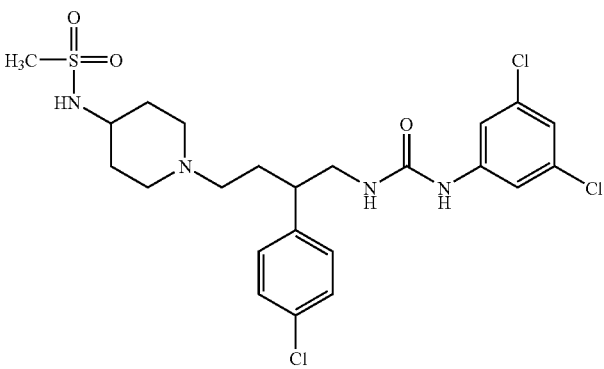 | 546.1026 | 547.1, 551.1 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 180 | | 505.2011 | 506.0, 508.1 | B |
| 181 | | 570.1122 | 571.0, 573.0, 575.1 | B |
| 182 | | 559.1075 | 559.9, 562.0, 563.9 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 183 | 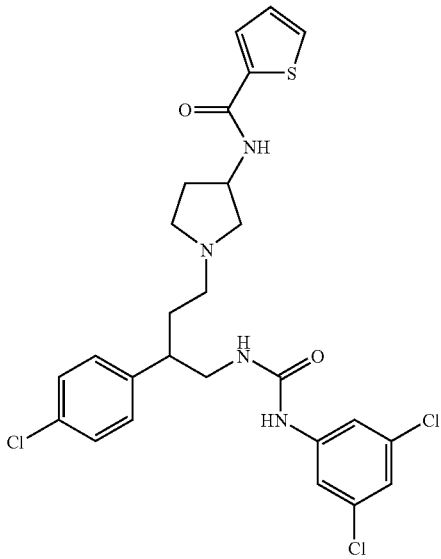 | 564.0920 | 565.0, 567.0, 569.1 | B |
| 184 | 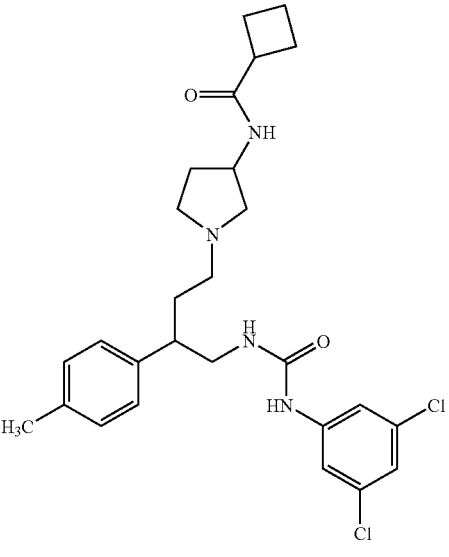 | 516.2058 | 517.1, 519.3 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 185 | 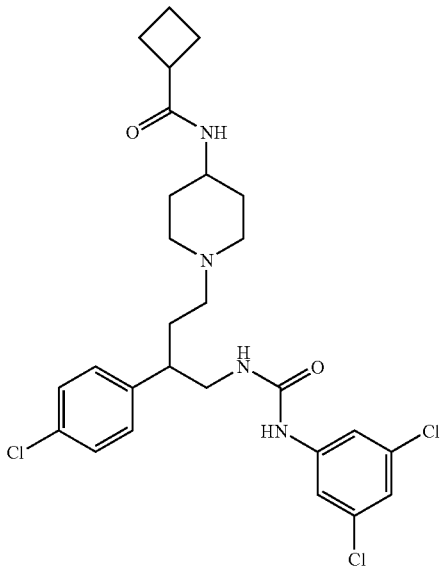 | 550.1669 | 551.0, 553.1 | B |
| 186 | 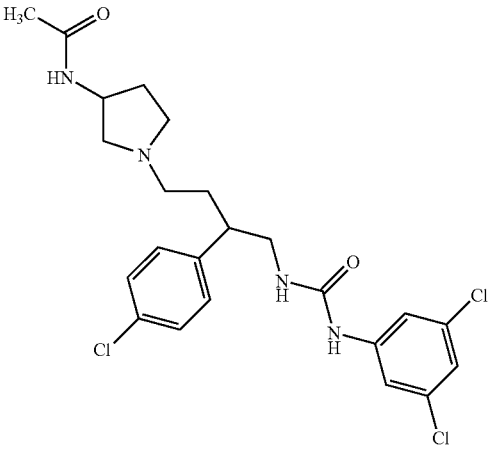 | 496.1199 | 497.1, 501.1 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 187 | 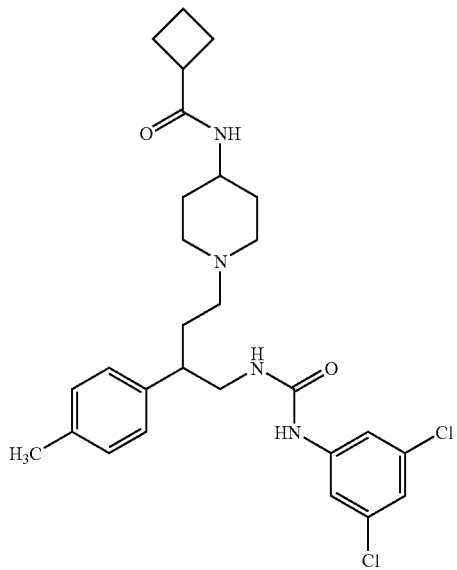 | 530.2215 | 531.1, 533.2 | B |
| 188 | 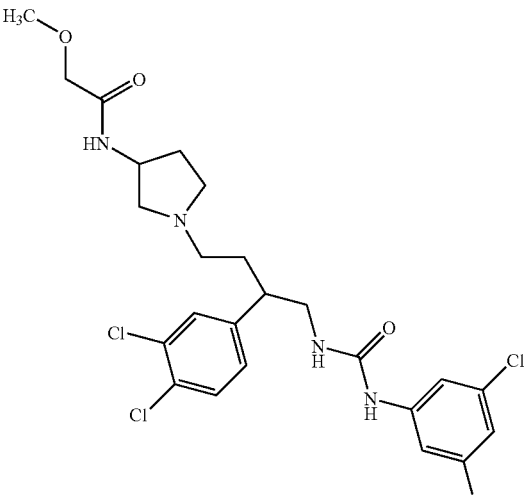 | 560.0915 | 561.0, 563.0, 565.1 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 189 | 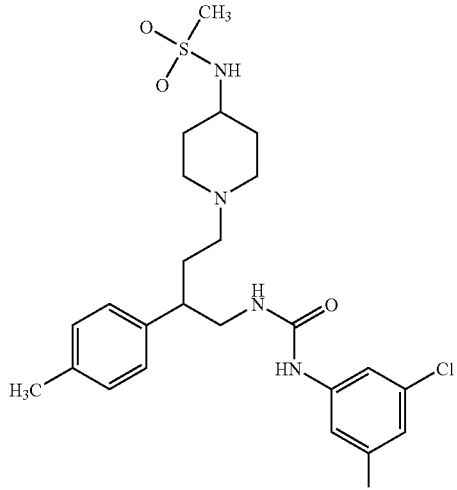 | 526.1572 | 527.0, 529.1 | B |
| 190 | 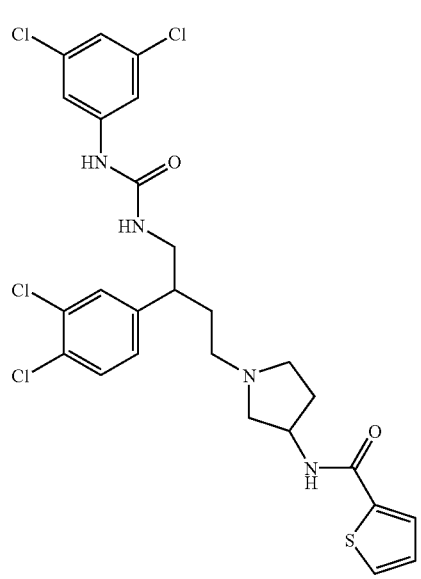 | 598.0530 | 598.9, 601.0, 603.0 | B |
| 191 | 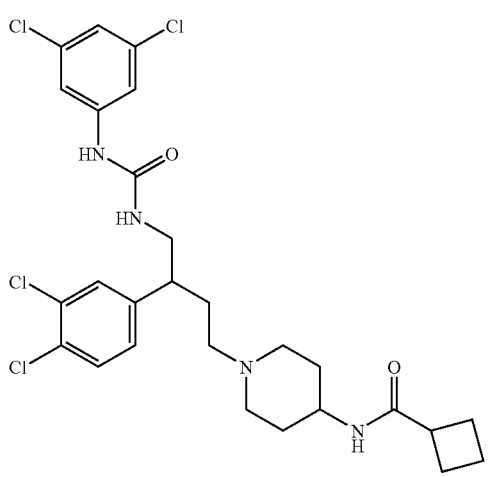 | 584.1279 | 585.2, 587.1, 589.1 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 192 | 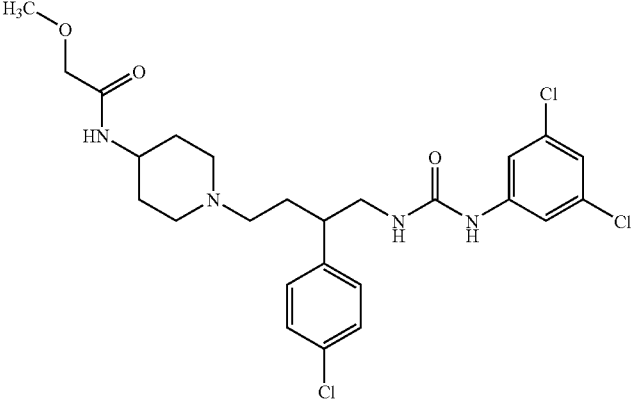 | 540.1461 | 541.0, 543.0 | B |
| 193 | 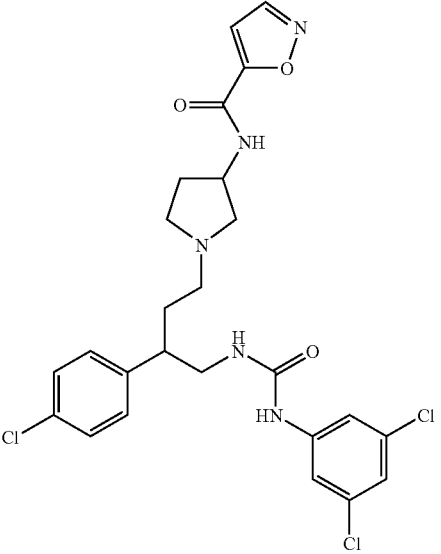 | 549.1101 | 552.0, 554.1 | B |
| 194 | 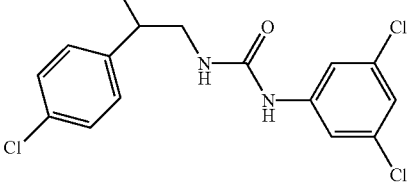 | 526.1305 | 527.1, 529.0 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 195 | 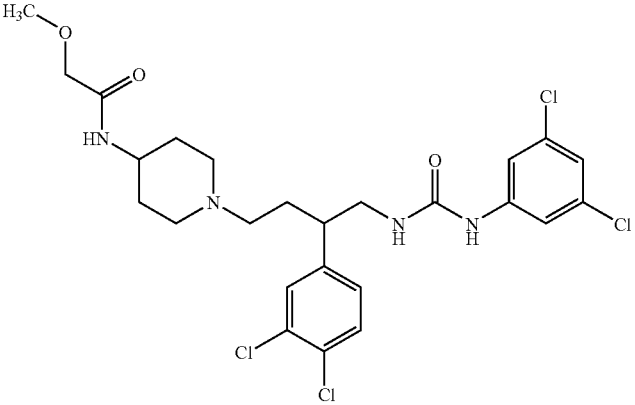 | 574.1072 | 575.1, 577.0, 579.1 | B |
| 196 | 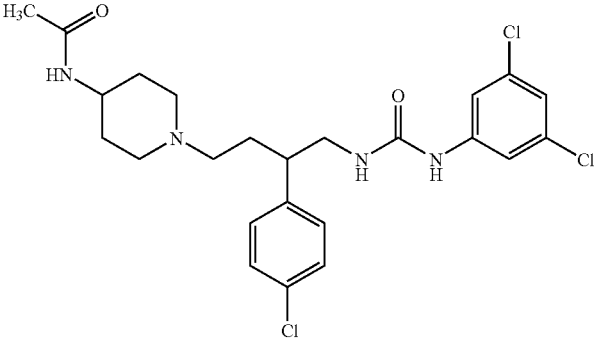 | 510.1356 | 511.0, 513.1 | B |
| 197 | 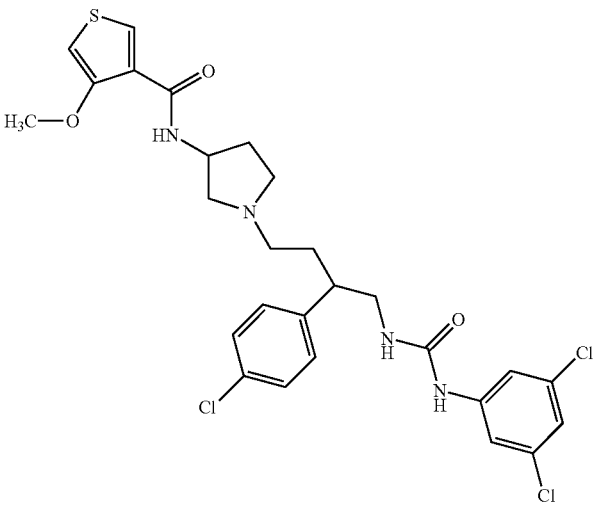 | 594.1026 | 597.0, 599.1 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 198 | 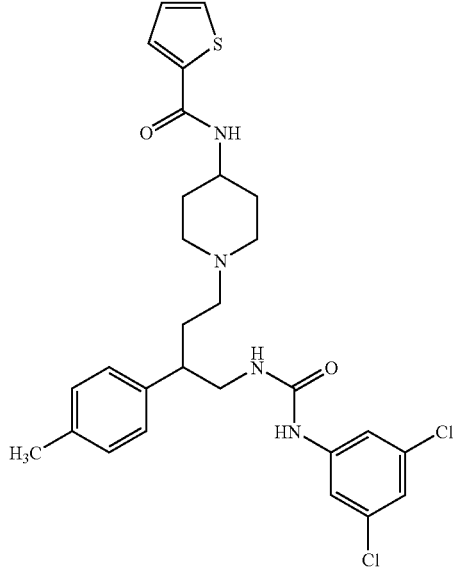 | 558.1623 | 559.1, 561.2 | B |
| 199 | 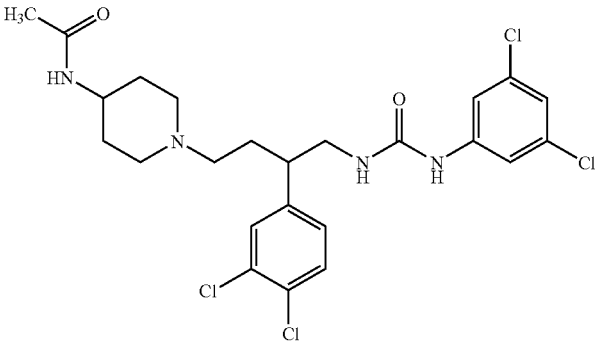 | 544.0966 | 545.0, 547.0, 549.0 | B |
| 200 | 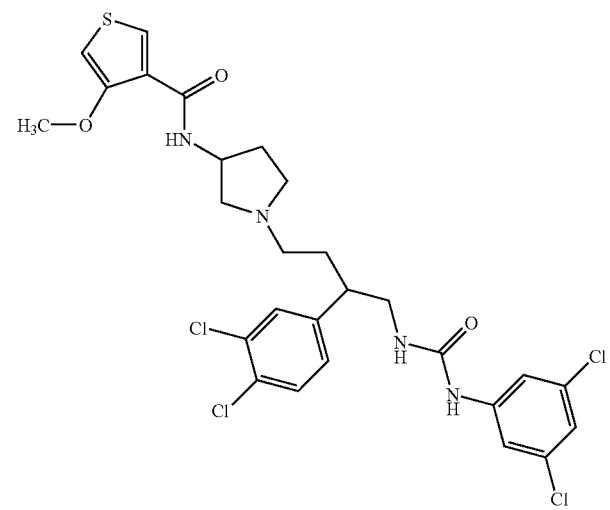 | 628.0636 | 629.0, 631.0, 632.9 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 201 | 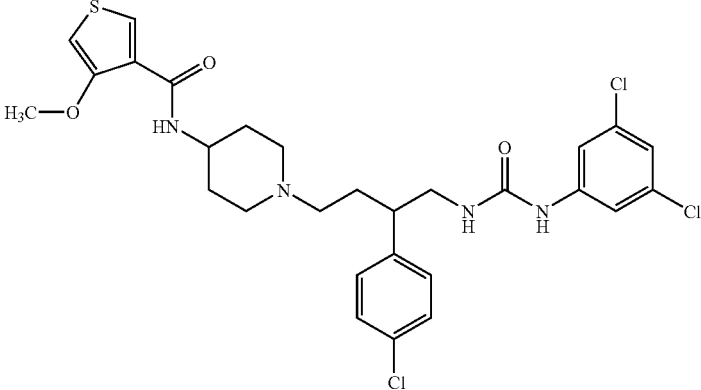 | 608.1182 | 609.1, 611.0 | C |
| 202 | 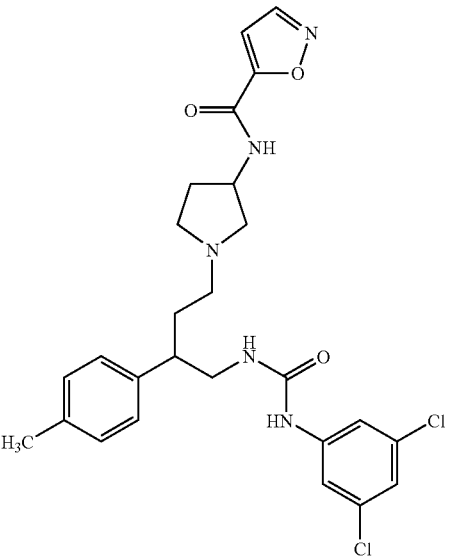 | 529.1647 | 530.1, 532.1 | C |
| 203 | 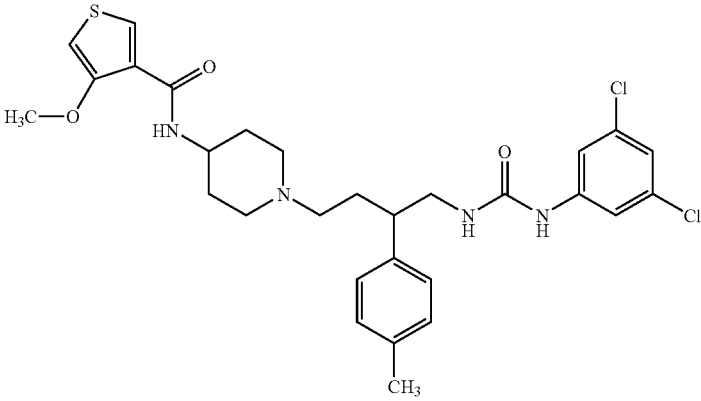 | 588.1728 | 589.0, 591.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 204 | 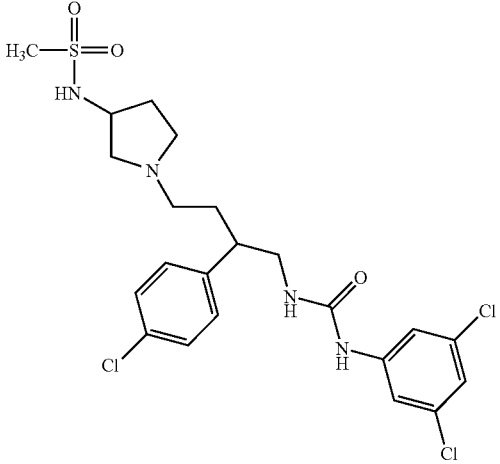 | 532.0869 | 533.0, 535.0 | C |
| 205 | 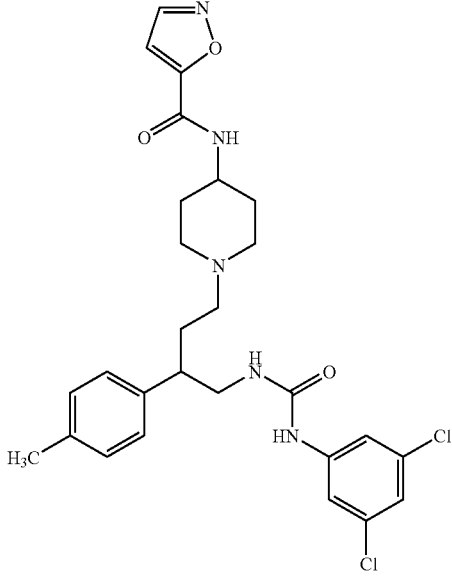 | 543.1804 | 544.1, 546.2 | C |
| 206 | 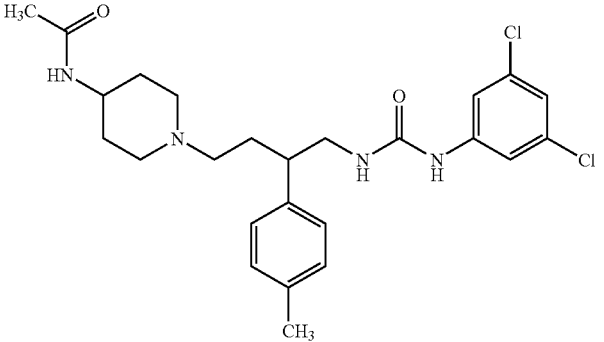 | 490.1902 | 491.1, 493.2 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 207 | 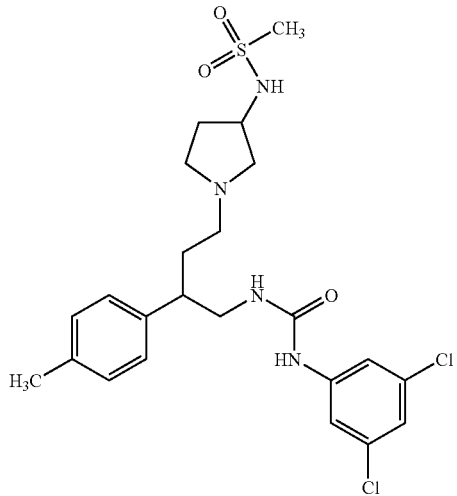 | 512.1415 | 513.0, 515.0 | C |
| 208 | 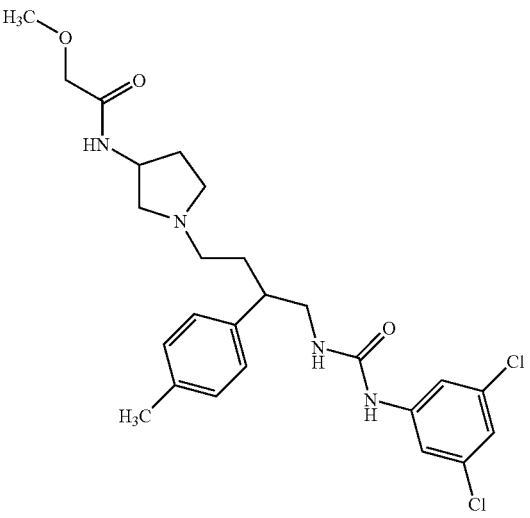 | 506.1851 | 507.1, 509.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 209 | 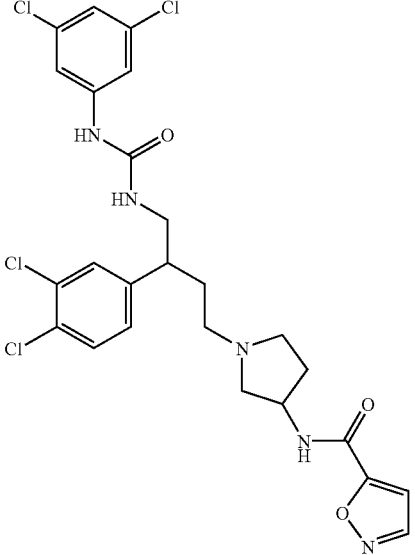 | 583.0711 | 584.0, 586.0, 588.0 | C |
| 210 | 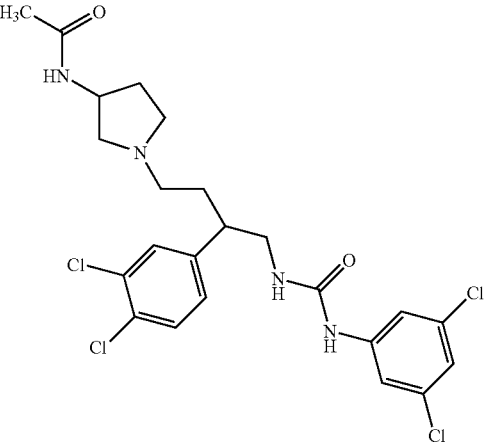 | 530.0809 | 531.0, 533.0, 535.0 | C |
| 211 | 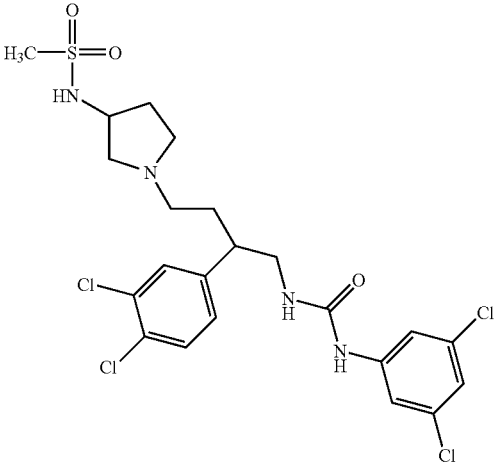 | 566.0479 | 567.0, 569.0, 571.0 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 212 | 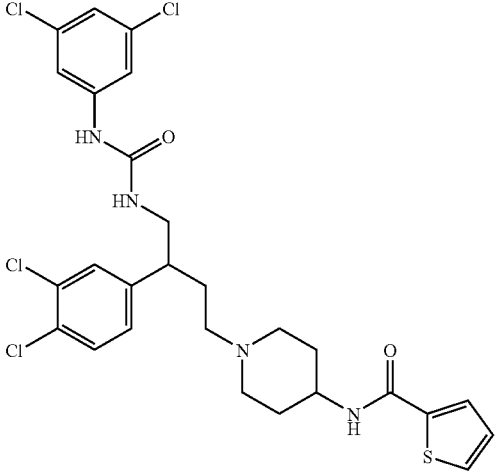 | 612.0687 | 613.2, 615.0 | C |
| 213 | 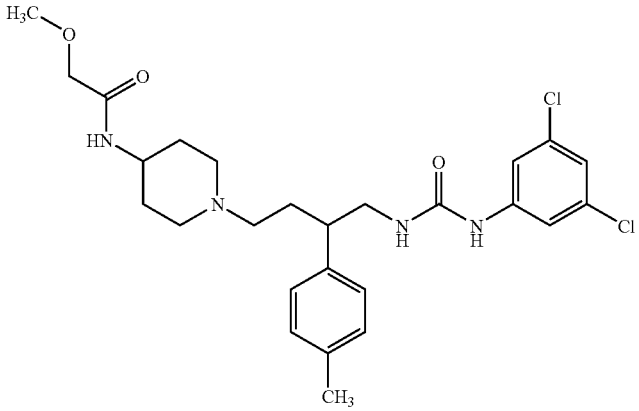 | 520.2008 | 521.1, 523.1 | C |
| 214 | 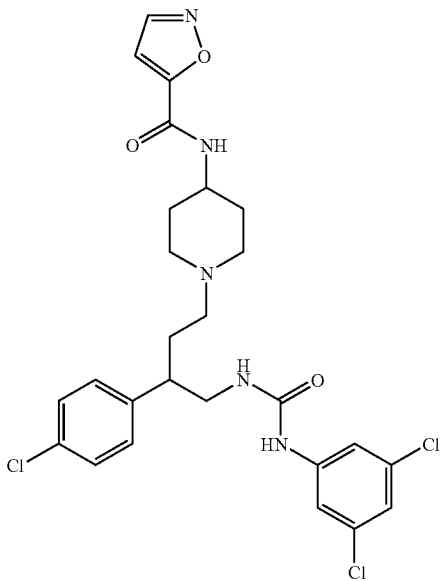 | 563.1257 | 564.0, 566.1, 568.0 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---------|-----------|-----------------|----------------|----------|
| 215 | 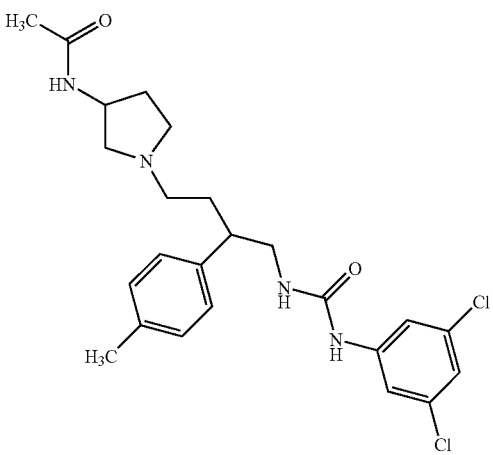 | 476.1745 | 477.1, 479.1 | C |
| 216 | 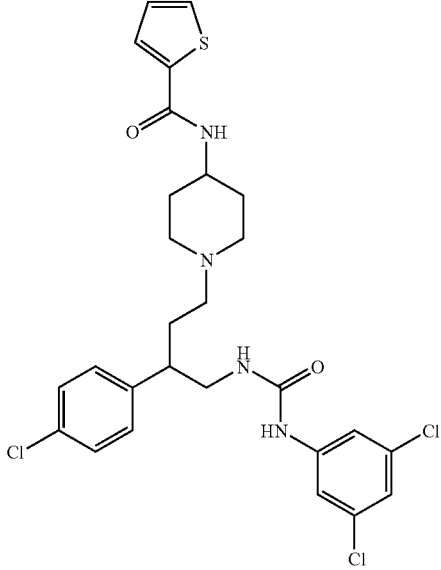 | 578.1076 | 579.1, 581.0 | C |
| 217 | 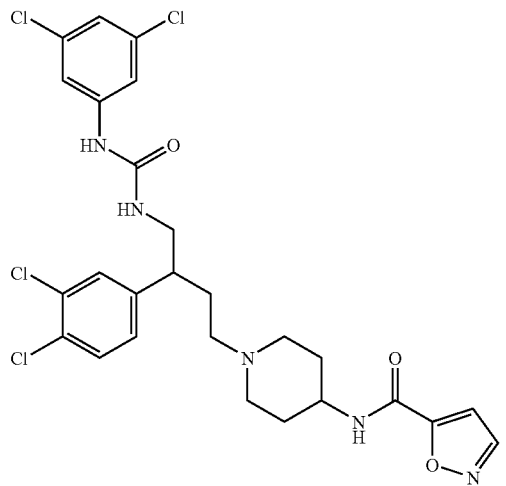 | 597.0868 | 598.0, 600.1, 602.2 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 218 | | 537.2062 | 538.0, 548.1 | A |
| 219 | | 540.1695 | 541.1, 543.0 | A |
| 220 | | 557.1960 | 558.0, 568.1 | A |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 221 | | 546.1720 | 547.0, 549.0 | A |
| 222 | | 529.1454 | 530.0, 532.1 | A |
| 223 | | 556.2008 | 557.0, 559.0 | A |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 224 | | 564.1625 | 565.0, 567.0, 569.1 | A |
| 225 | | 495.1844 | 496.1, 498.1 | A |
| 226 | | 547.1360 | 548.1, 550.0, 552.0 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 227 | | 539.1742 | 540.0, 542.0 | B |
| 228 | | 585.2161 | 586.2, 588.1 | B |
| 229 | | 501.1408 | 502.1, 504.0 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 230 | 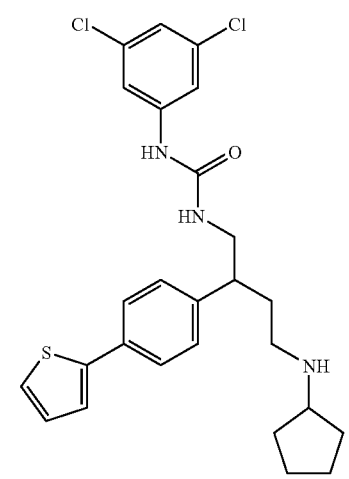 | 501.1408 | 502.1, 504.0 | B |
| 231 | 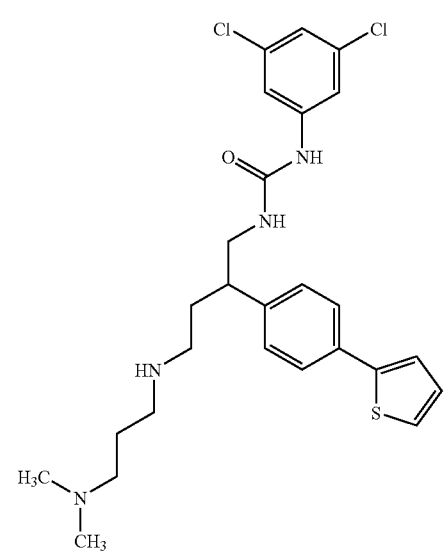 | 518.1674 | 519.0, 521.0 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 232 | 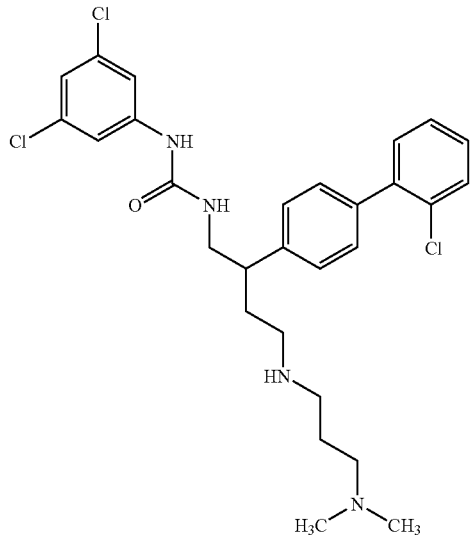 | 546.1720 | 547.1, 549.0, 551.0 | B |
| 233 | 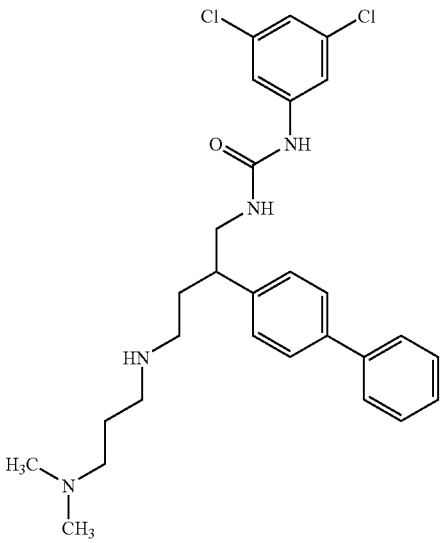 | 512.2109 | 513.1, 515.1 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 234 | 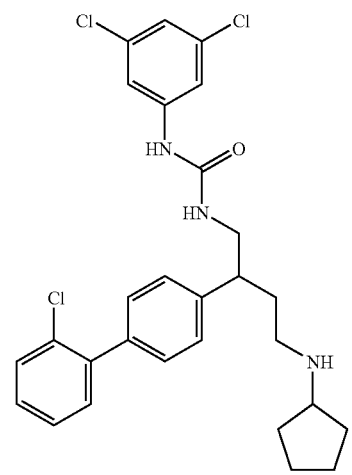 | 529.1454 | 530.0, 532.1 | B |
| 235 | 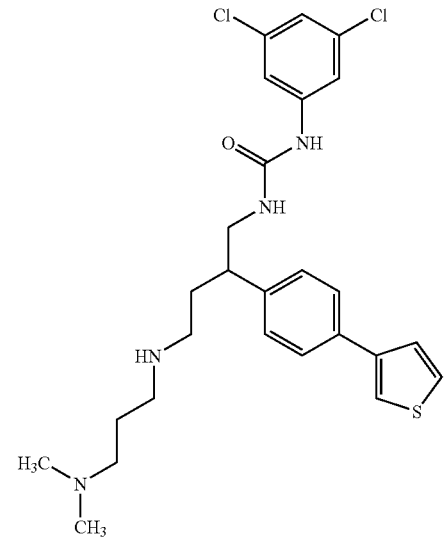 | 518.1674 | 519.1, 521.0 | B |
| 236 | 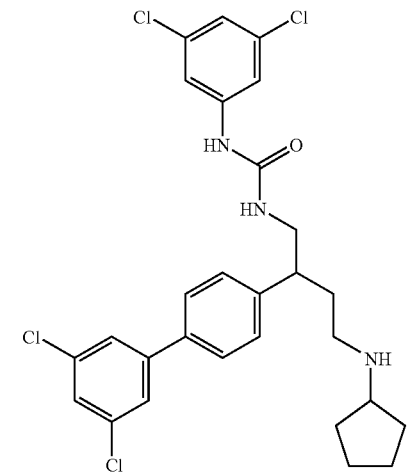 | 563.1064 | 564.0, 565.9, 568.0 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---------|-----------|-----------------|----------------|----------|
| 237 | 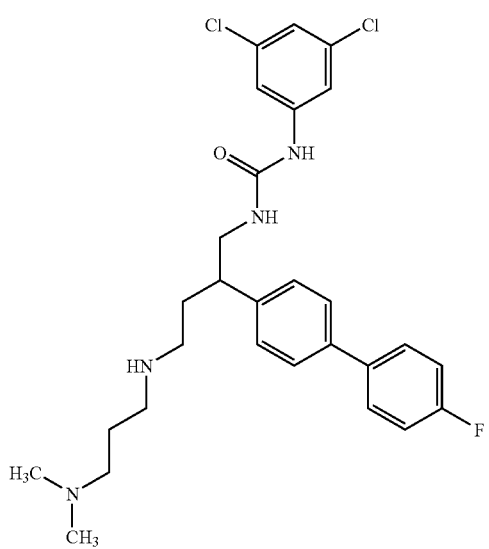 | 530.2015 | 531.0, 533.0 | B |
| 238 | 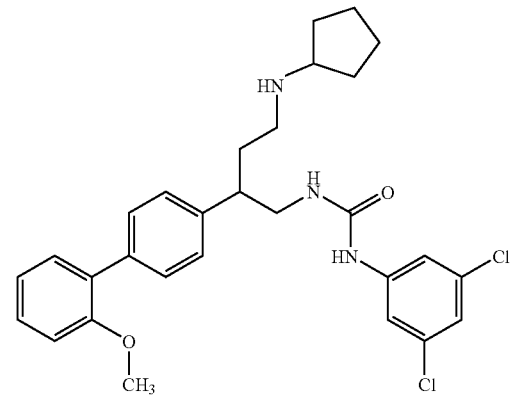 | 525.1950 | 526.1, 528.1 | B |
| 239 | 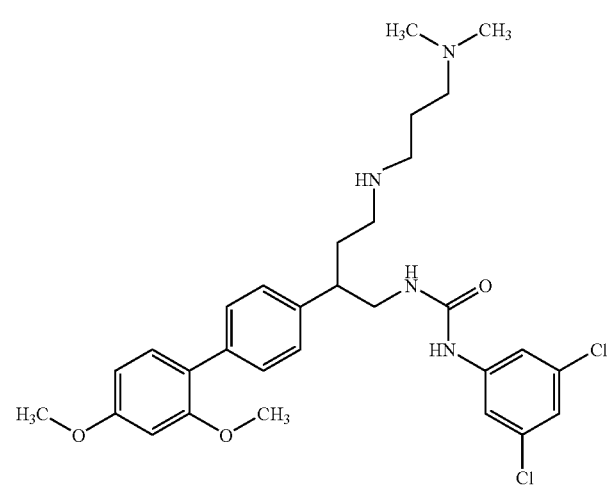 | 572.2321 | 573.1, 575.1 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 240 | 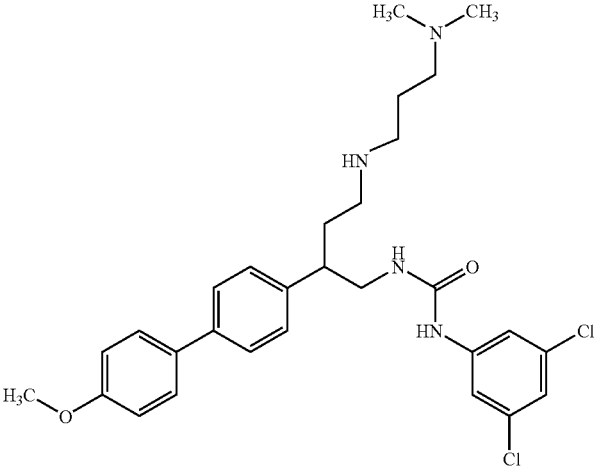 | 542.2215 | 543.1, 545.1 | B |
| 241 | 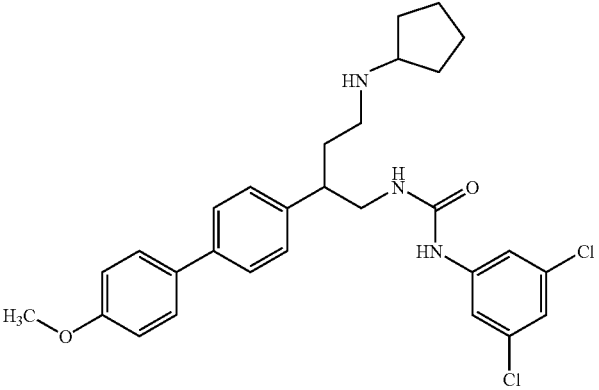 | 525.1950 | 526.0, 528.0 | B |
| 242 | 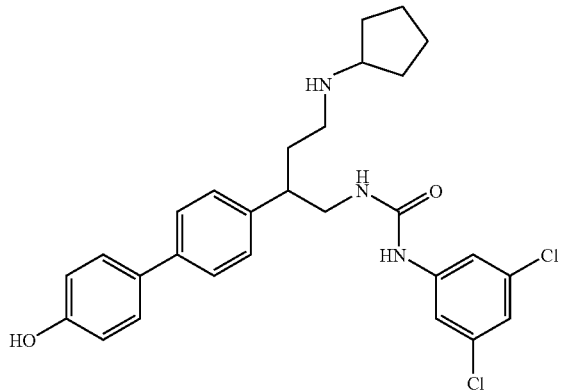 | 511.1793 | 512.0, 514.0 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 243 | | 513.1750 | 514.1, 516.0 | B |
| 244 | | 529.1454 | 530.0, 532.0, 534.0 | B |
| 245 | | 563.1064 | 564.0, 566.0, 568.0, 570.0 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 246 | 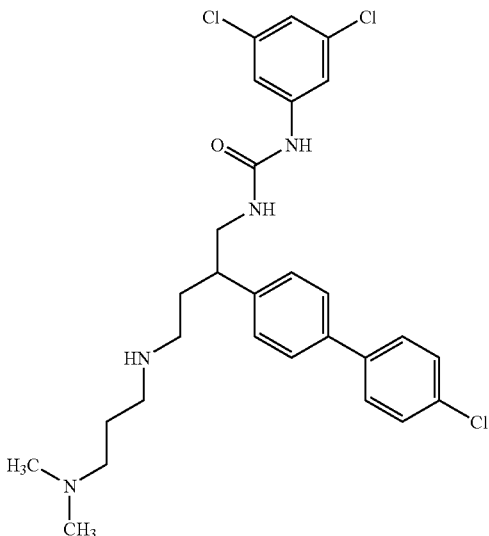 | 546.1720 | 547.0, 549.0 | B |
| 247 | 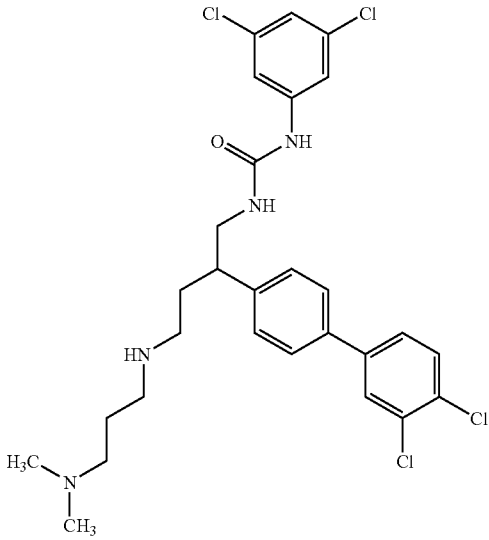 | 580.1330 | 581.0, 583.0, 585.0 | B |
| 248 | 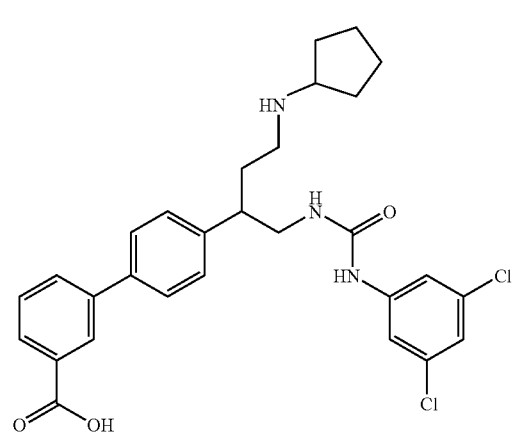 | 539.1742 | 540.1, 542.1 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 249 | 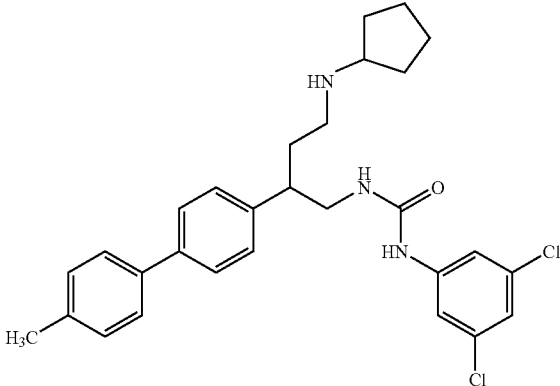 | 509.2000 | 510.1, 512.1 | B |
| 250 | 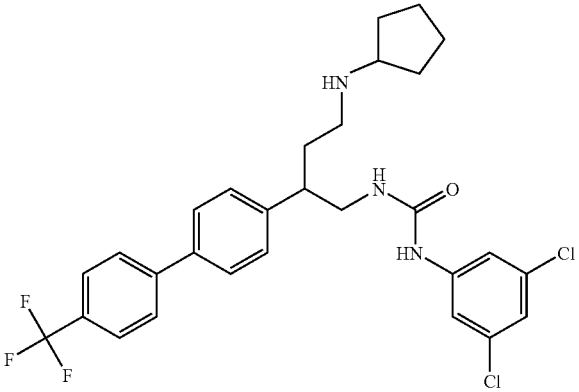 | 563.1718 | 564.0, 566.0 | B |
| 251 | 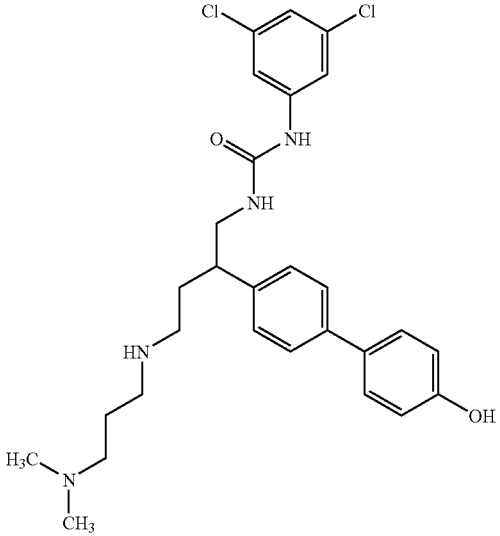 | 528.2058 | 529.1, 531.1 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 252 | 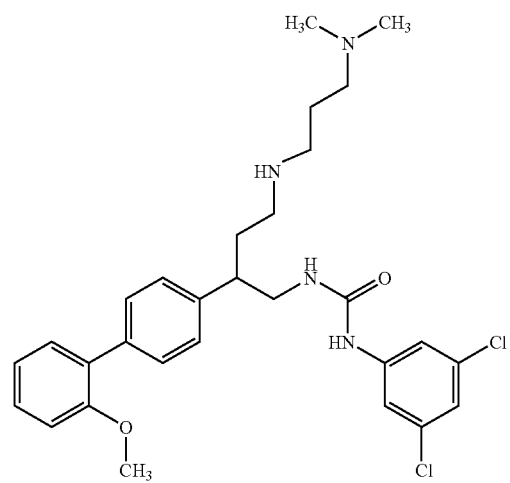 | 542.2215 | 543.1, 545.1 | B |
| 253 | 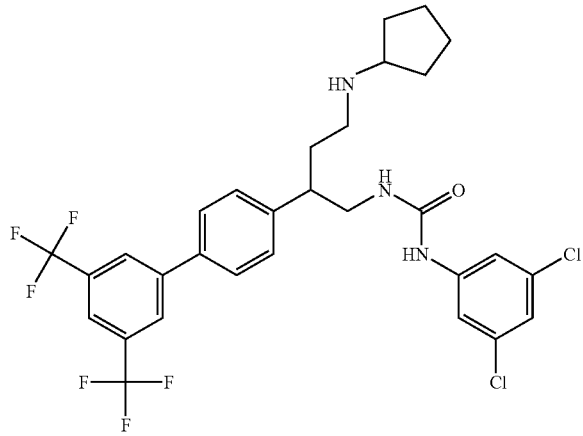 | 631.1591 | 632.1, 634.1 | C |
| 254 | 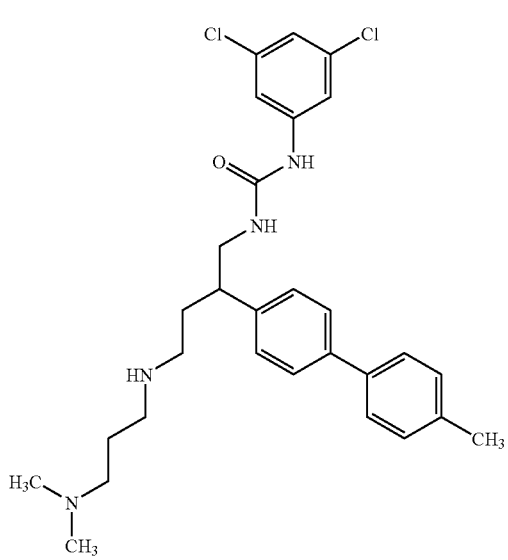 | 526.2266 | 527.1, 529.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 255 | | 580.1983 | 581.0, 583.1 | C |
| 256 | | 648.1857 | 649.1, 651.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 257 | 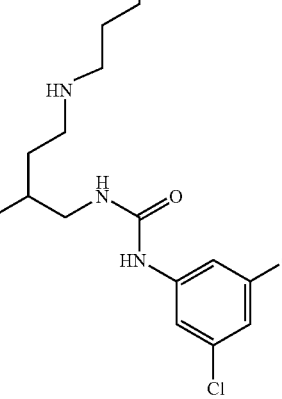 | 602.2426 | 603.1, 605.1, 606.1 | C |
| 258 | 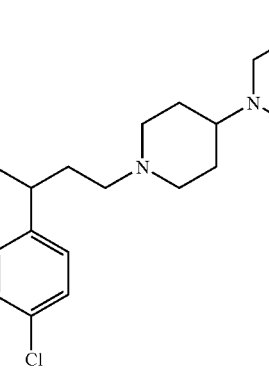 | 552.2234 | 555.0, 557.0, 558.0, 559.1 | B |
| 259 | 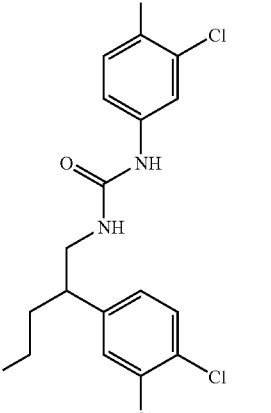 | 599.0912 | 597.9, 599.9, 602.0 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 260 | 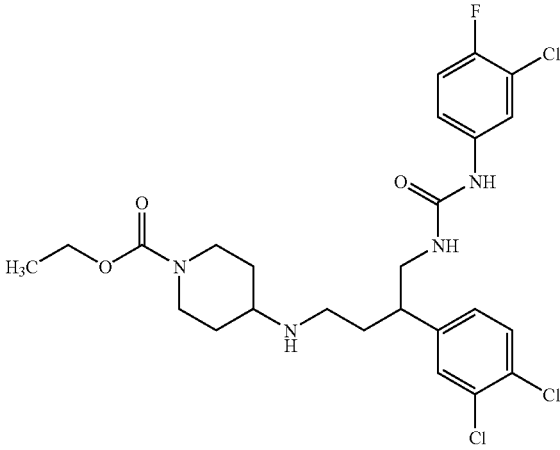 | 558.1367 | 559.0, 561.0 | B |
| 261 | 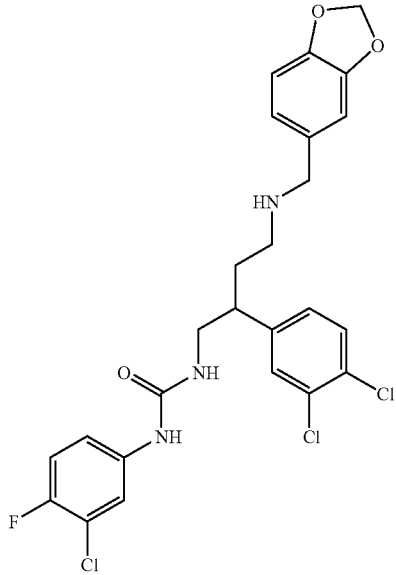 | 537.0789 | 537.8, 539.9, 541.8 | B |
| 262 | 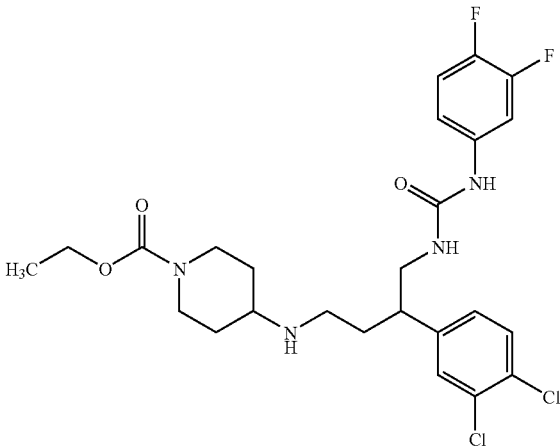 | 542.1663 | 543.0, 545.0 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 263 | | 457.0890 | 457.9, 459.9, 462.0 | C |
| 264 | | 569.1607 | 570.0, 572.0 | C |
| 265 | | 441.1186 | 442.0, 444.0 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 266 | 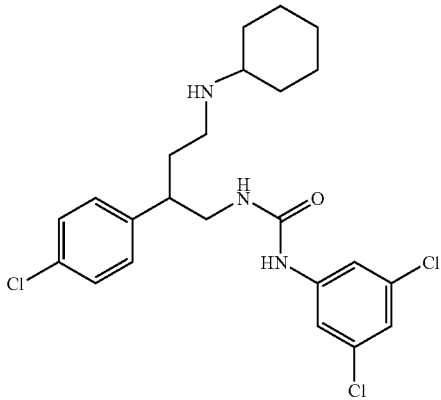 | 467.1298 | 468.1, 470.1 | B |
| 267 | 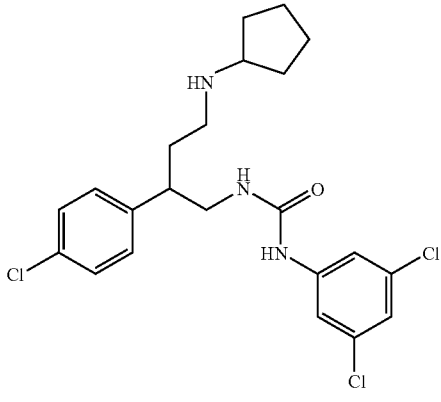 | 453.1141 | 454.0, 456.0 | B |
| 268 | 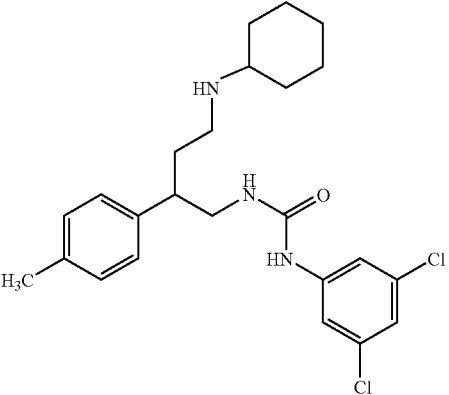 | 447.1844 | 448.0, 450.2 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 269 | 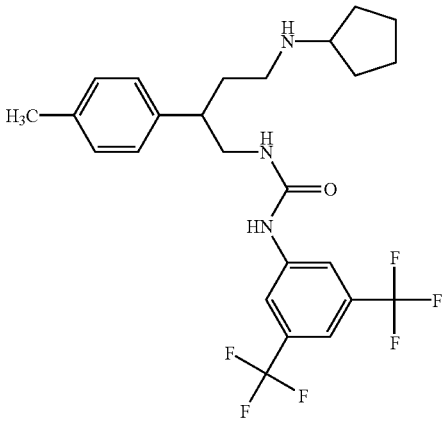 | 501.2214 | 502.2 | B |
| 270 | 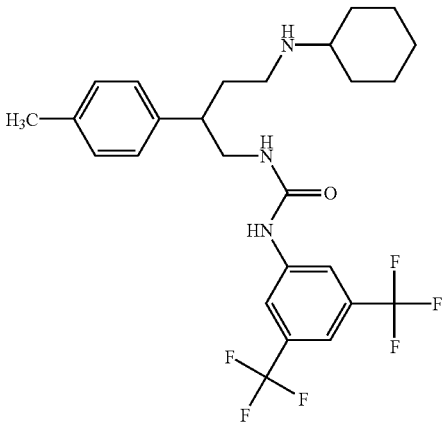 | 515.2371 | 516.1 | B |
| 271 | 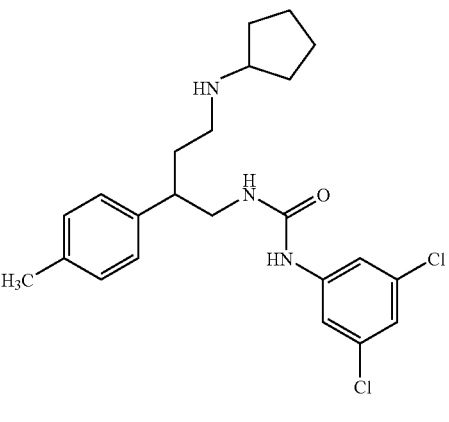 | 433.1687 | 434.0, 436.1 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 272 | | 419.1531 | 420.0, 422.1 | B |
| 273 | | 439.0985 | 440.0, 442.0 | B |
| 274 | | 487.2058 | 488.1 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 275 | 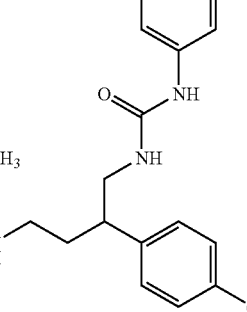 | 460.1432 | 460.8, 462.9 | C |
| 276 | 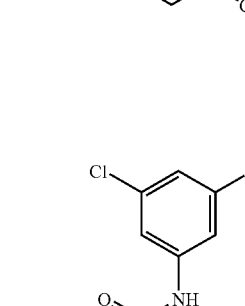 | 480.0886 | 480.7, 482.9 | C |
| 277 | 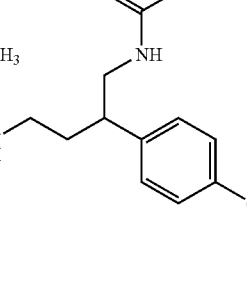 | 574.1072 | 575.0, 576.9, 579.0 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 278 | 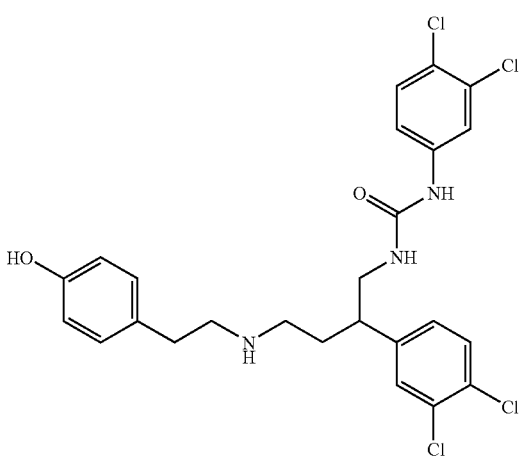 | 539.0701 | 540.0, 541.9, 544.0 | B |
| 279 | 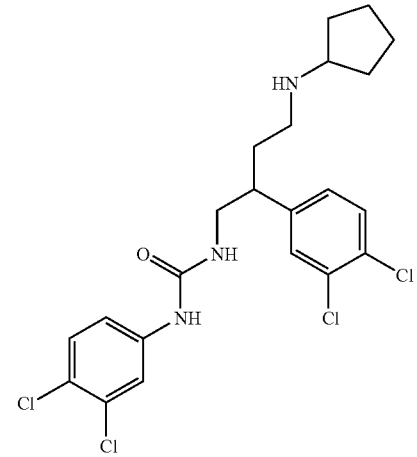 | 487.0751 | 488.0, 490.0, 492.0 | B |
| 280 | 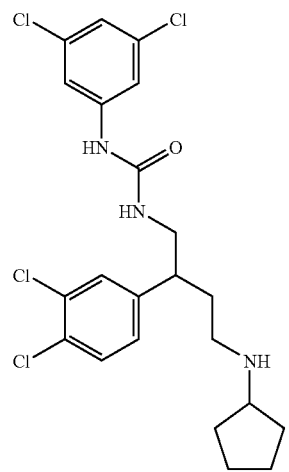 | 487.0751 | 487.9, 490.0, 491.9 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 281 | 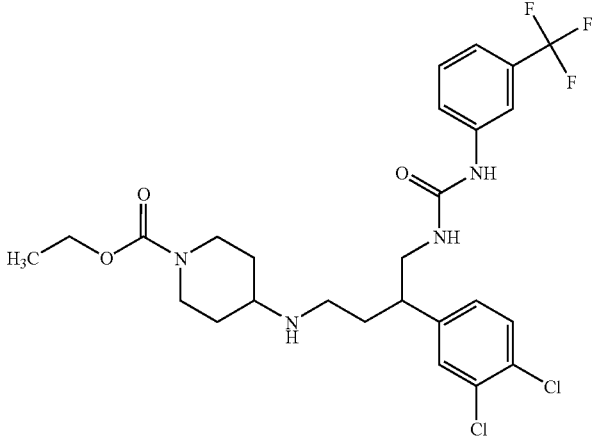 | 574.1725 | 575.0, 577.0 | B |
| 282 | 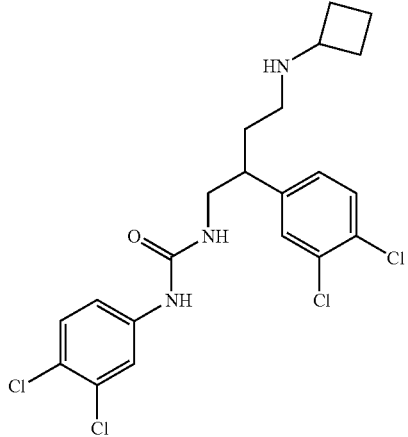 | 473.0595 | 475.9, 479.1 | B |
| 283 | 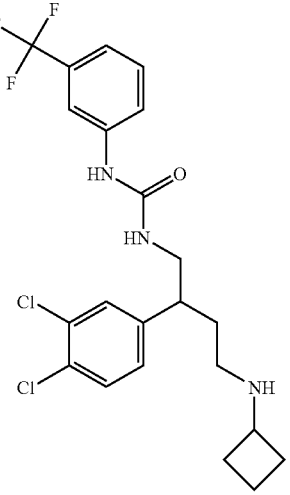 | 473.1248 | 474.1, 476.1 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 284 | | 527.0813 | 528.0, 530.0, 531.9 | B |
| 285 | | 562.1514 | 563.0, 565.0 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 286 | 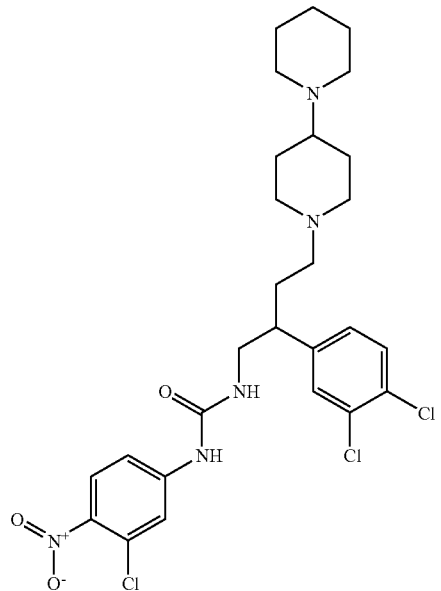 | 581.1727 | 582.1, 584.1, 586.1 | B |
| 287 | 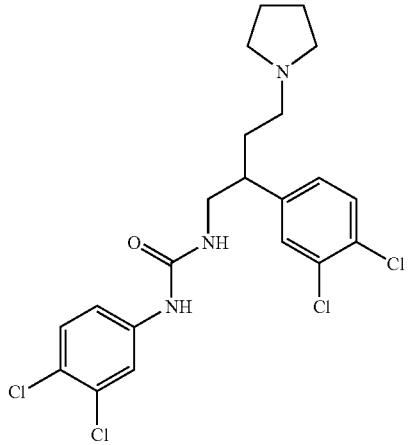 | 473.0595 | 474.0, 476.0, 478.0 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 288 | | 489.1561 | 490.0, 492.0 | B |
| 289 | | 489.0908 | 492.0, 494.1 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 290 | 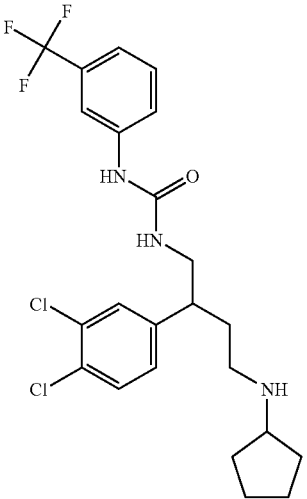 | 487.1405 | 488.0, 490.1 | B |
| 291 | 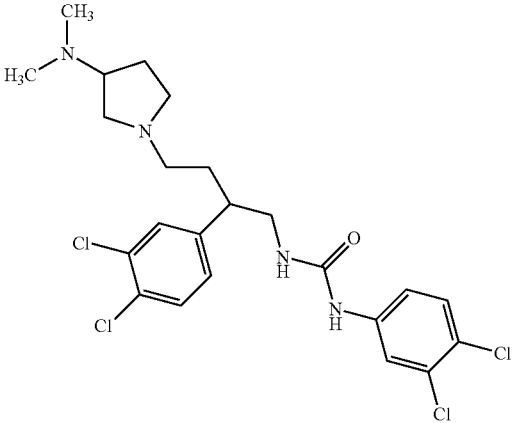 | 516.1017 | 517.1, 519.0, 521.0 | B |
| 292 | 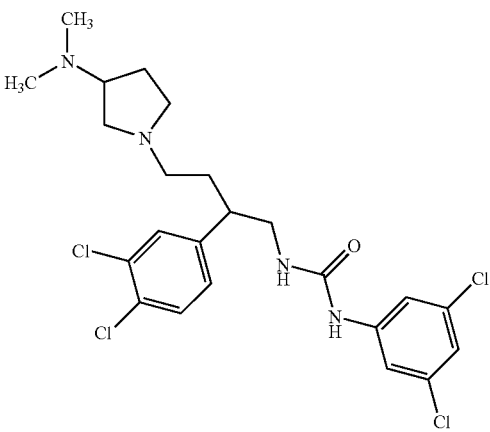 | 516.1017 | 517.0, 519.0, 521.0 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 293 | 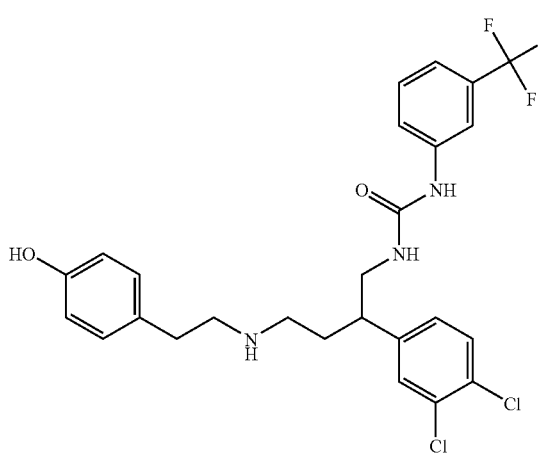 | 539.1354 | 540.0, 541.9 | B |
| 294 | 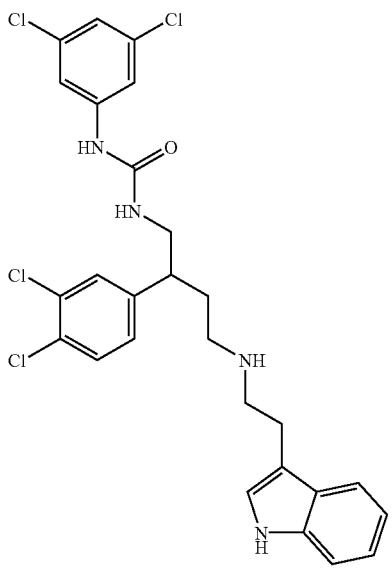 | 562.0860 | 563.1, 565.0, 567.0 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 295 | | 553.0493 | 553.8, 555.8, 557.8 | C |
| 296 | | 553.0493 | 553.9, 555.9 | C |
| 297 | | 527.0813 | 528.0, 530.0, 531.9 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 298 | 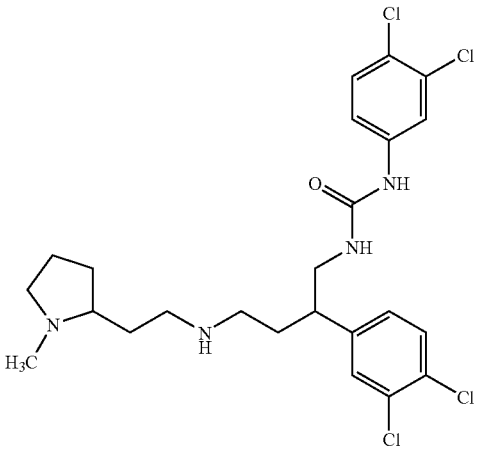 | 530.1173 | 530.9, 533.0, 535.0 | C |
| 299 | 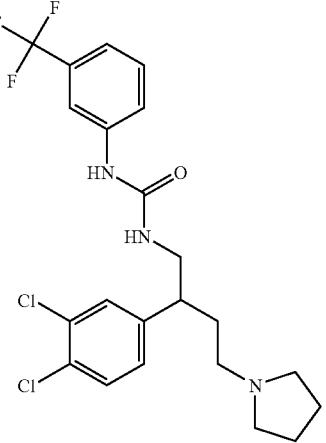 | 473.1248 | 474.1, 476.0 | C |
| 300 | 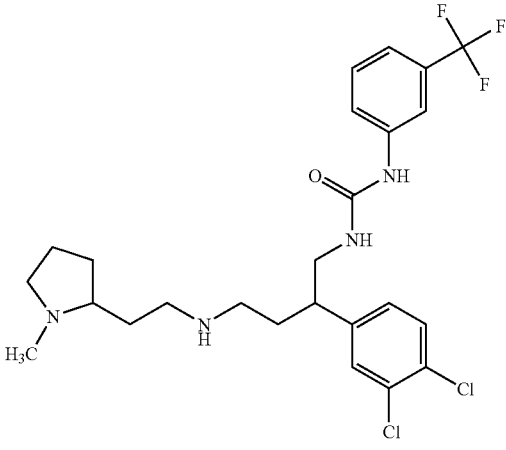 | 530.1827 | 531.1, 533.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 301 | | 530.1173 | 531.0, 532.9, 535.1 | C |
| 302 | | 553.1146 | 553.9, 555.9 | C |
| 303 | | 527.1466 | 528.1, 530.0 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 304 | 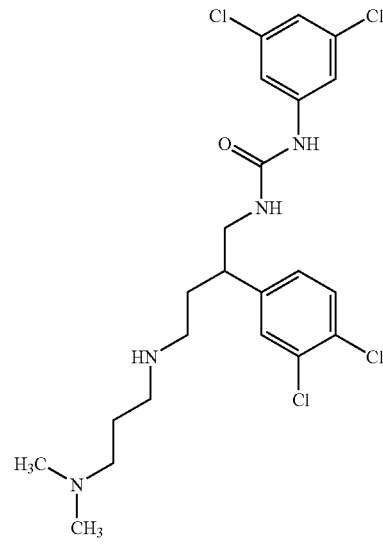 | 504.1017 | 505.0, 506.9 | C |
| 305 | 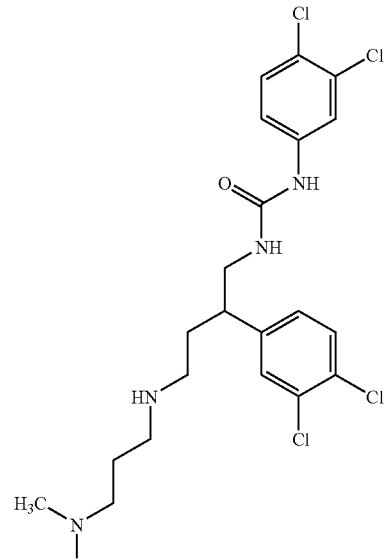 | 504.1017 | 505.0, 507.0, 509.0 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 306 | 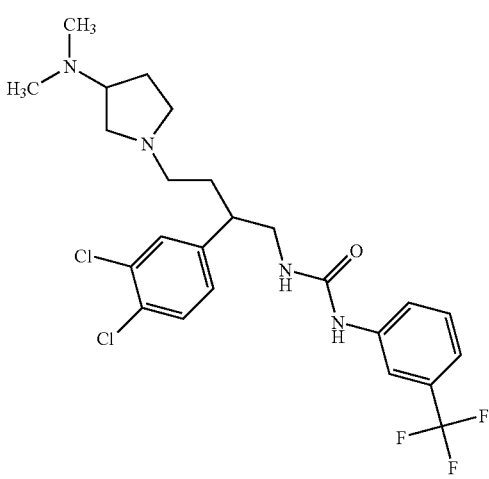 | 516.1670 | 517.0, 519.1 | C |
| 307 | 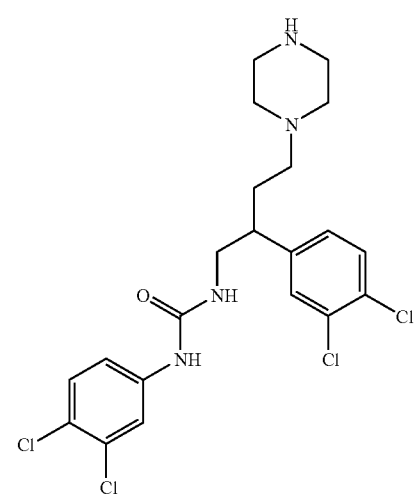 | 488.0704 | 489.0, 491.0, 493.1 | C |
| 308 | 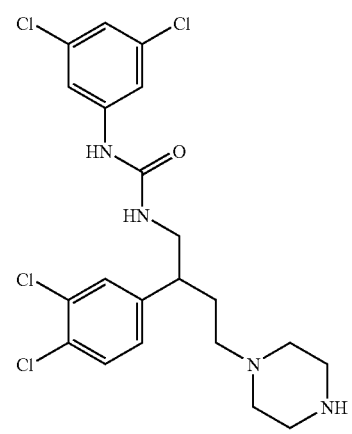 | 488.0704 | 489.0, 491.0, 493.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 309 | 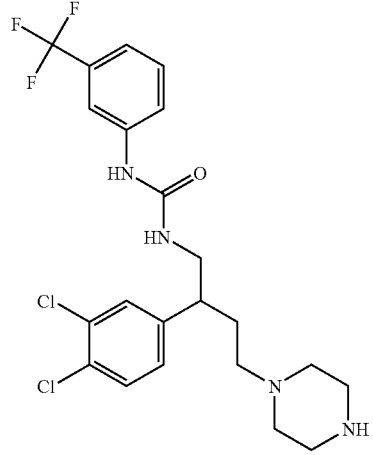 | 488.1357 | 489.0, 491.1 | C |
| 310 | 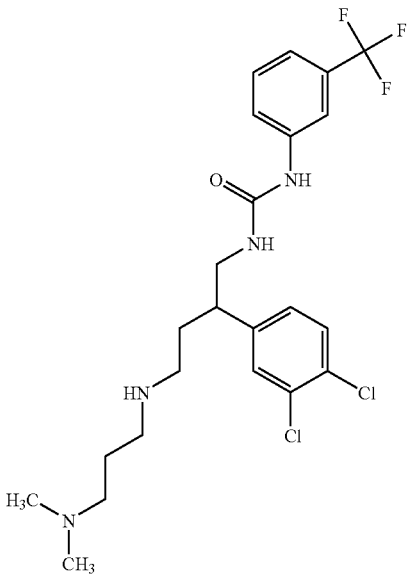 | 504.1670 | 505.1, 507.0 | C |
| 311 | 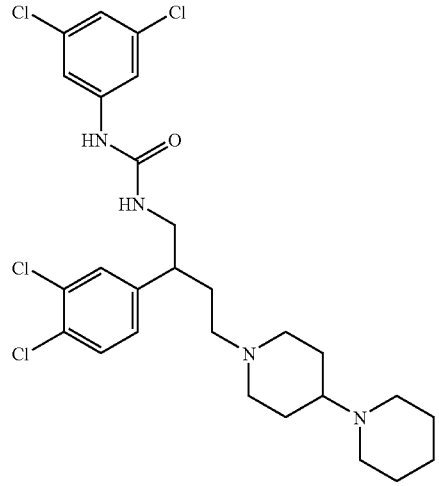 | 570.1486 | 571.0, 573.1, 575.1 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 312 | | 580.1371 | 581.0, 583.0, 585.0 | B |
| 313 | | 536.1876 | 560.0, 562.0, 564.0 | B |
| 314 | | 541.1122 | 542.8, 544.8 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 315 | | 547.2117 | 548.1, 550.0, 551.1 | B |
| 316 | | 559.1075 | 560.0, 562.0, 564.1 | C |
| 317 | | 547.2117 | 548.1, 550.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 318 | 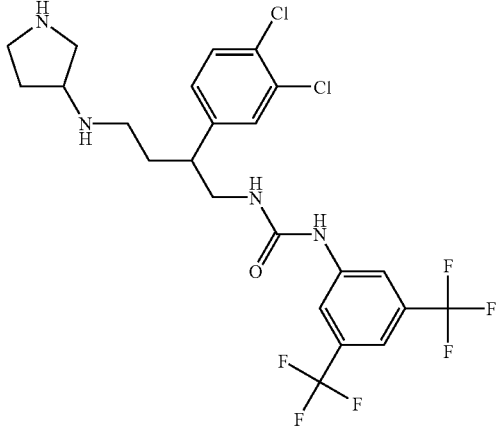 | 556.1231 | 556.9, 559.1 | C |
| 319 | 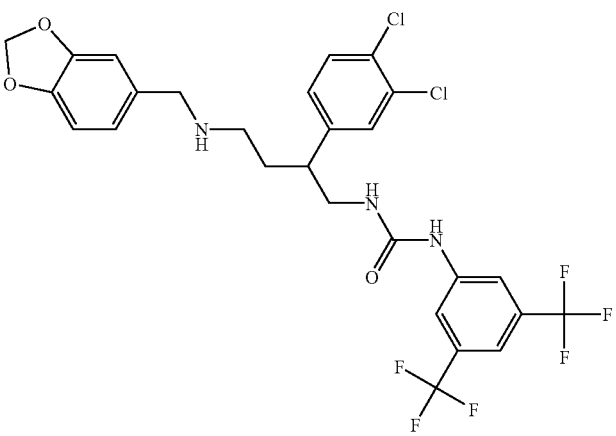 | 621.1020 | 621.8, 623.8 | C |
| 320 | 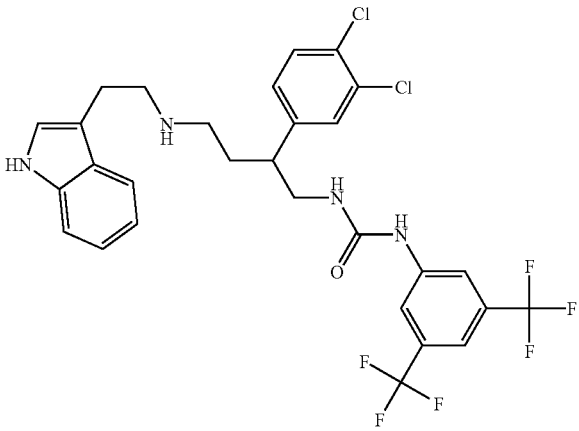 | 630.1387 | 631.0, 632.9, 634.0 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 321 | 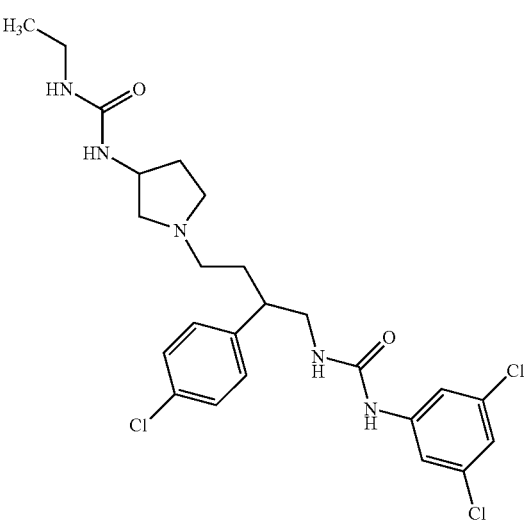 | 525.1465 | 526.0, 528.0 | C |
| 322 | 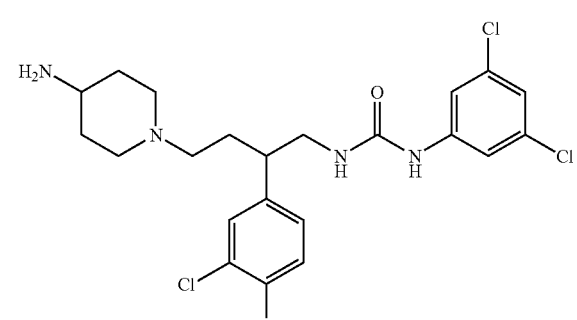 | 502.0860 | 503.0, 505.0, 507.1 | C |
| 323 | 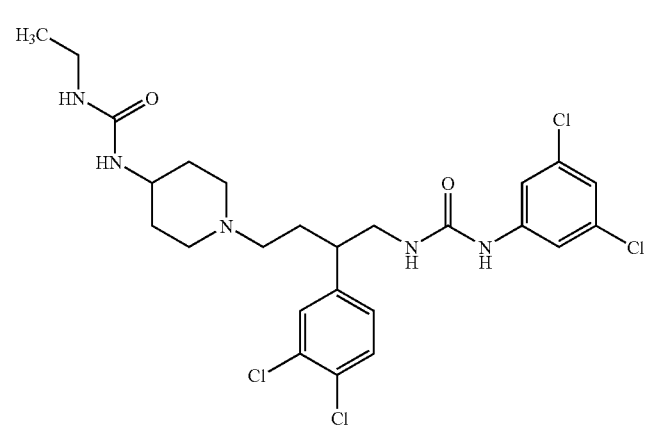 | 573.1231 | 574.0, 576.0 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 324 | 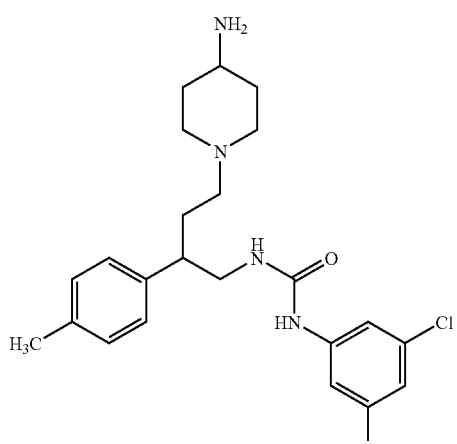 | 488.1796 | 449.1, 451.1 | C |
| 325 | 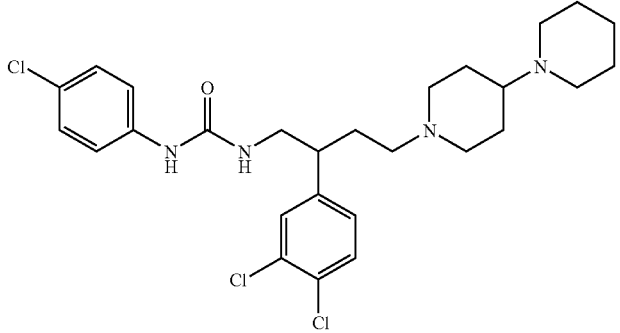 | 536.1876 | 537.0, 539.0 | C |
| 326 | 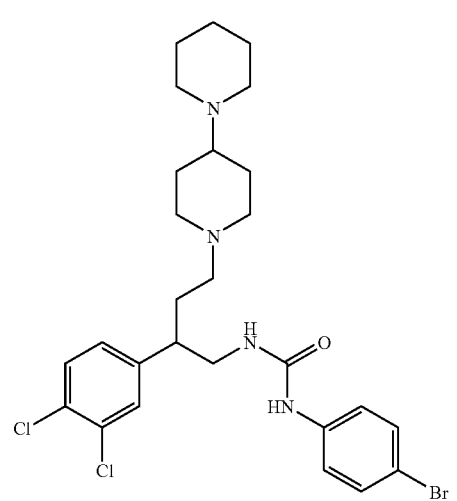 | 580.1371 | 581.0, 583.0, 585.0 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 327 | 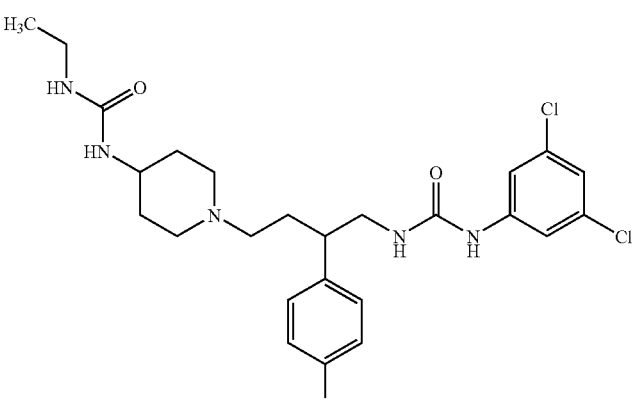 | 519.2167 | 520.1, 522.1 | C |
| 328 | 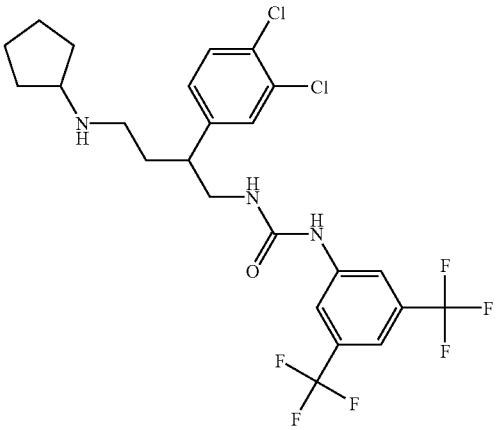 | 555.1278 | 556.1, 558.1 | A |
| 329 | 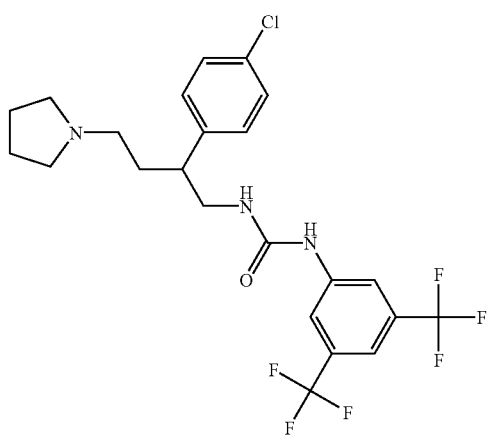 | 507.1512 | 508.2, 510.2 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 330 | 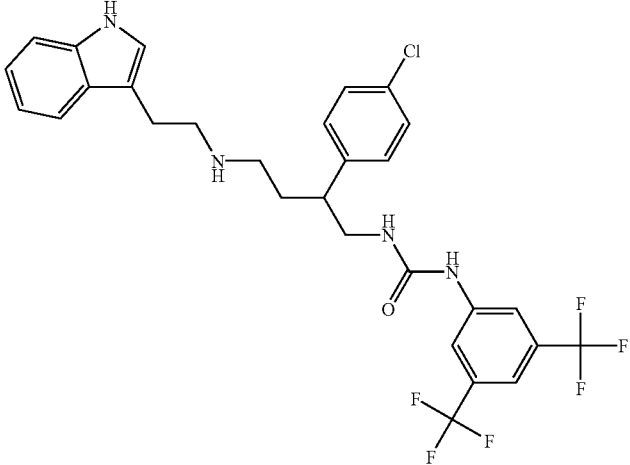 | 596.1777 | 597.1, 599.1 | B |
| 331 | 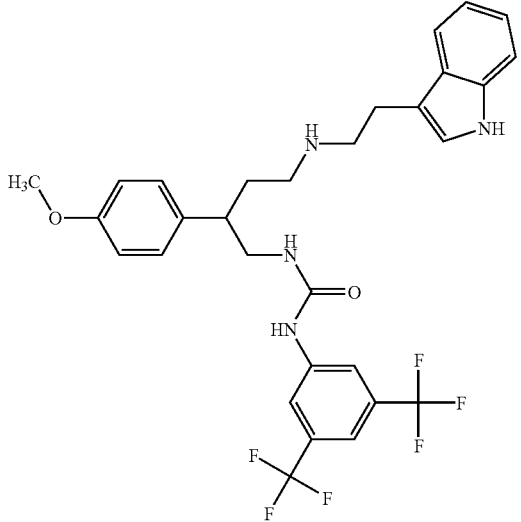 | 592.2272 | 593.1 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 332 | | 558.1387 | 559.0, 561.0 | B |
| 333 | | 596.1777 | 597.1, 599.1 | B |
| 334 | | 507.1512 | 508.2, 510.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 335 | | 503.2007 | 504.2 | C |
| 336 | | 576.2323 | 577.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 337 | | 538.1934 | 539.1, 541.1 | C |
| 338 | | 487.2058 | 488.2 | C |
| 339 | | 533.1106 | 534.0, 535.9 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 340 | | 549.0811 | 549.9, 551.9, 553.0 | C |
| 341 | | 491.1807 | 492.2 | C |
| 342 | | 549.0811 | 552.0, 554.0 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 343 | | 580.2073 | 581.1 | C |
| 344 | | 538.1934 | 539.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 345 | 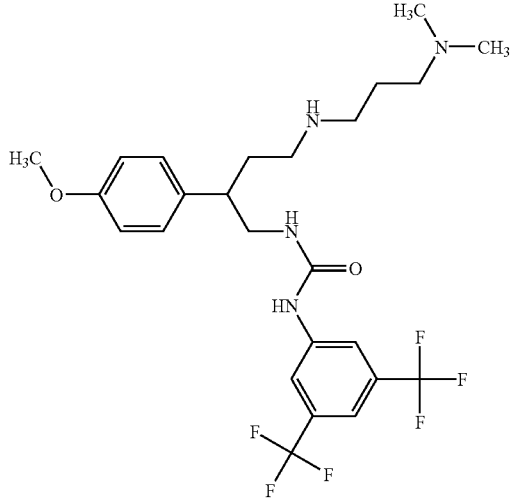 | 534.2429 | 535.1 | C |
| 346 | 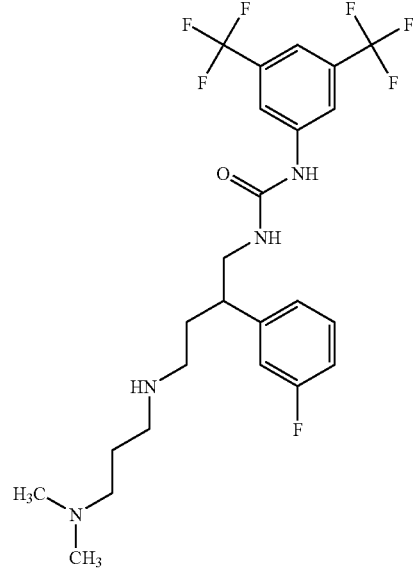 | 522.2229 | 523.2 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 347 | 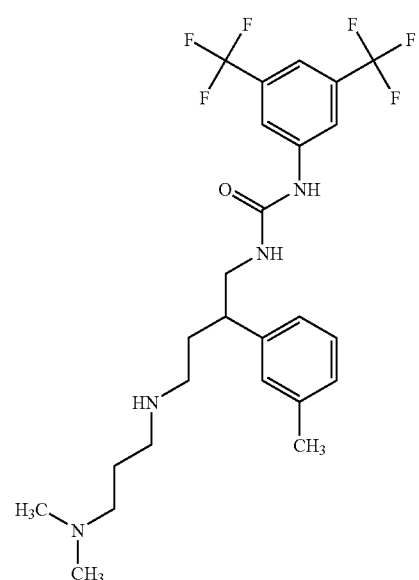 | 518.2480 | 519.2 | C |
| 348 | 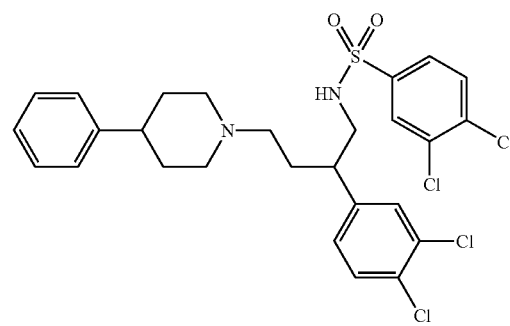 | 584.0625 | 585.1, 587.1, 589.1, 591.2 | C |
| 349 | 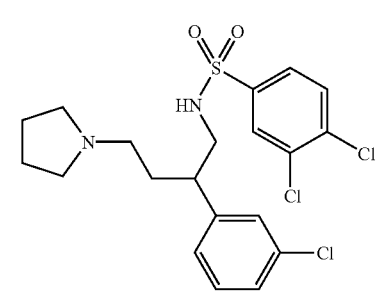 | 460.0546 | 461.1, 463.1, 465.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 350 | | 433.1687 | 434.2, 436.2 | B |
| 351 | | 516.2422 | 517.2, 519.1 | B |
| 352 | | 433.1687 | 434.2, 436.2 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 353 | | 433.1687 | 434.1, 436.1 | B |
| 354 | | 425.2678 | 426.2 | C |
| 355 | | 393.2780 | 394.2 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 356 | 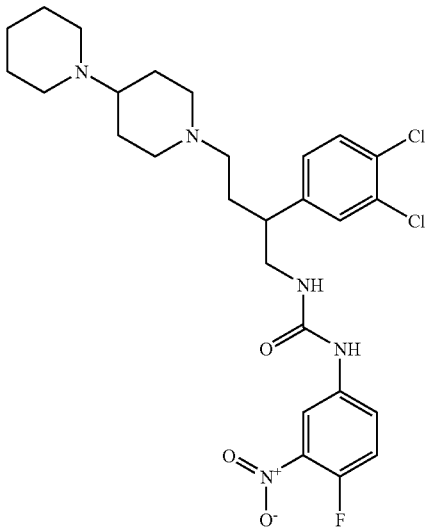 | 565.2022 | 566.1, 568.2 | B |
| 357 | 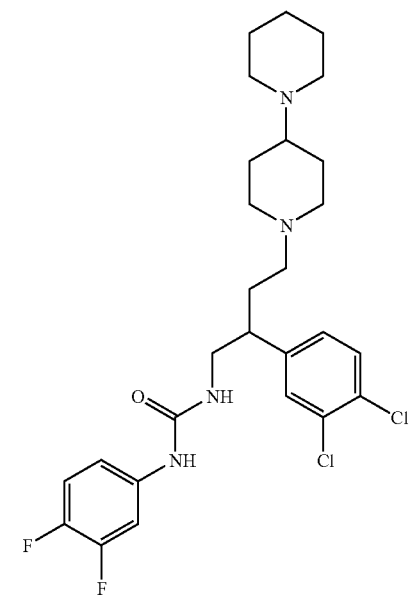 | 538.2077 | 539.1, 541.1 | B |
| 358 | 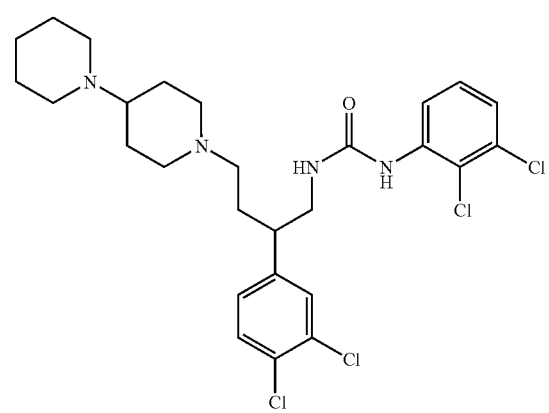 | 570.1486 | 571.1, 573.1, 575.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 359 | | 658.0475 | 659.0, 661.0, 663.0, 665.0 | C |
| 360 | | 570.1486 | 571.1, 573.1, 575.1 | C |
| 361 | | 534.2328 | 535.2, 537.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 362 | 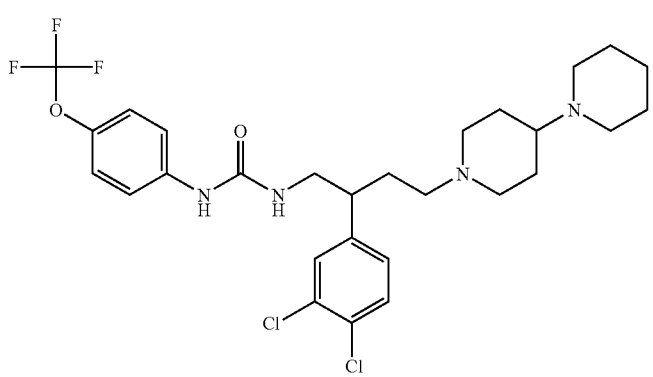 | 586.2089 | 587.2, 589.1 | C |
| 363 | 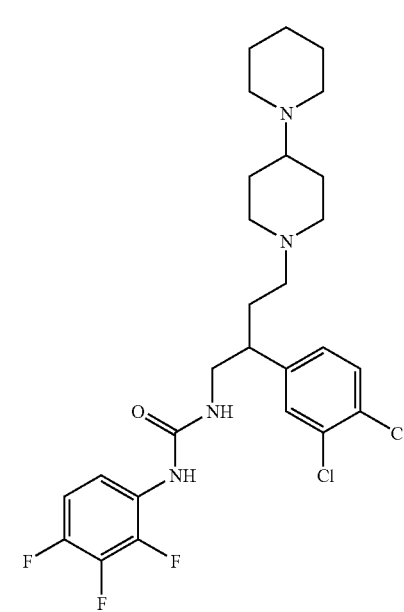 | 556.1983 | 557.2, 559.2 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 364 | | 554.1782 | 555.1, 557.1, 559.1 | B |
| 365 | | 570.2140 | 571.2, 573.2 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 366 | 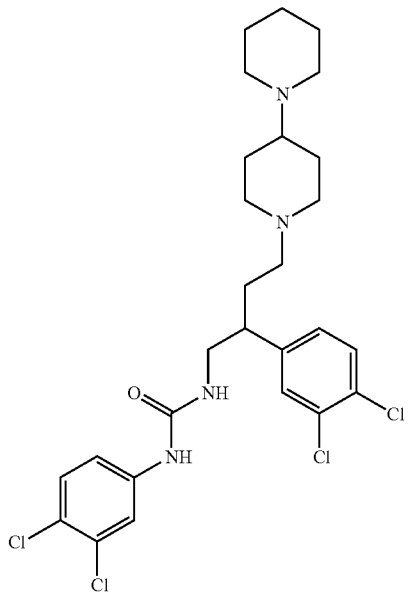 | 570.1486 | 571.1, 573.2 | B |
| 367 | 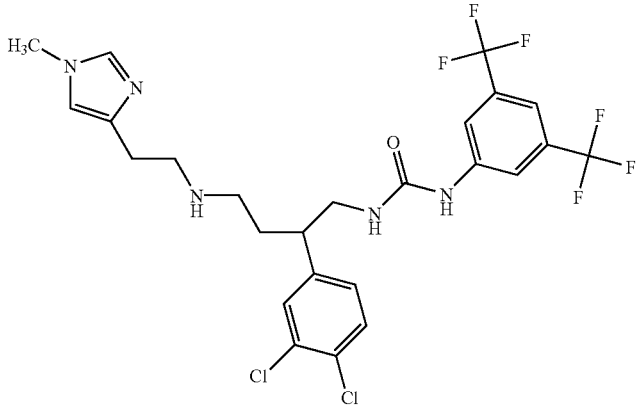 | 595.1340 | 596.1, 598.1 | C |
| 368 | 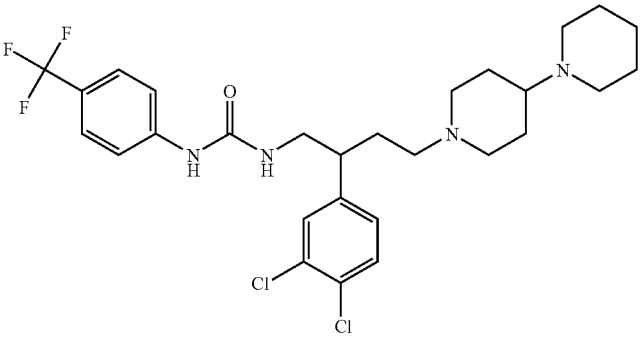 | 570.2140 | 571.2, 573.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 369 | 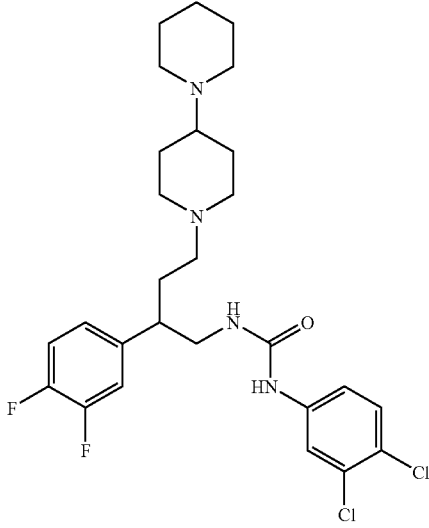 | 538.2077 | 539.1, 541.1 | C |
| 370 | 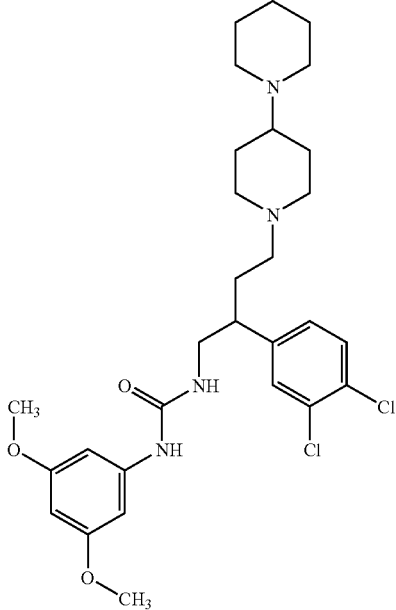 | 562.2477 | 563.2, 565.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 371 | 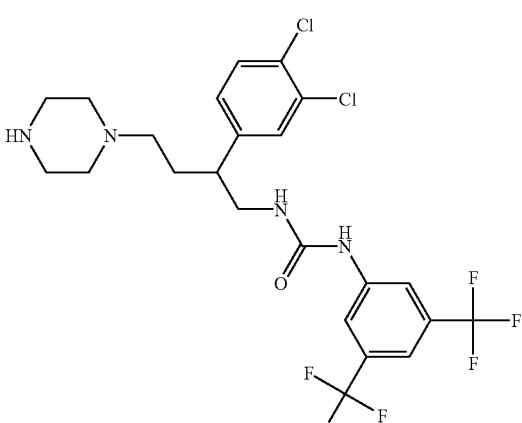 | 556.1231 | 557.1, 559.1 | C |
| 372 | 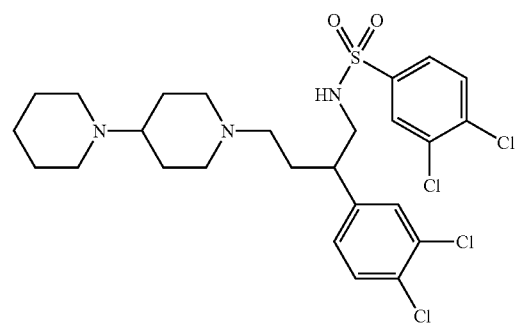 | 591.1047 | 592.1, 594.1, 596.0 | C |
| 373 | 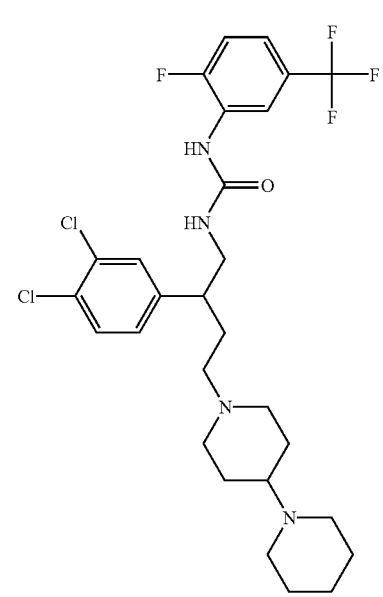 | 588.2045 | 589.1, 591.0, 593.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 374 | 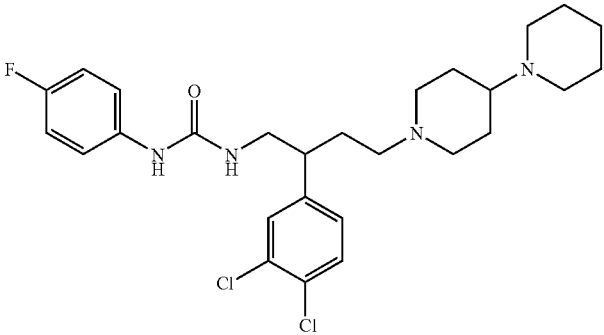 | 520.2172 | 521.2, 523.1 | C |
| 375 | 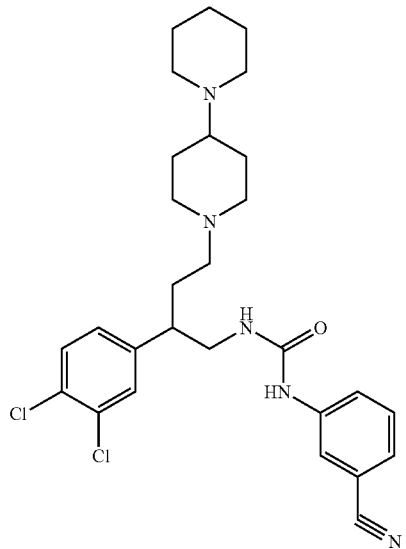 | 527.2218 | 528.2, 530.1 | C |
| 376 | 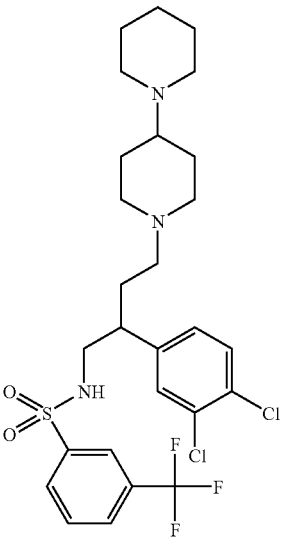 | 591.1700 | 592.1, 594.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 377 | | 530.2579 | 531.2, 533.2 | C |
| 378 | | 522.2373 | 523.2, 524.3 | C |
| 379 | | 526.1013 | 527.0, 529.0 | C |

US 7,034,056 B2
317 318
TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 380 | 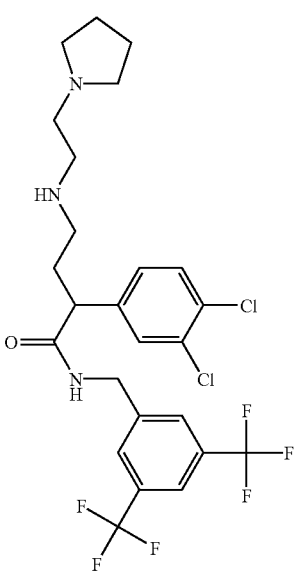 | 569.1435 | 570.0, 572.1 | C |
| 381 | 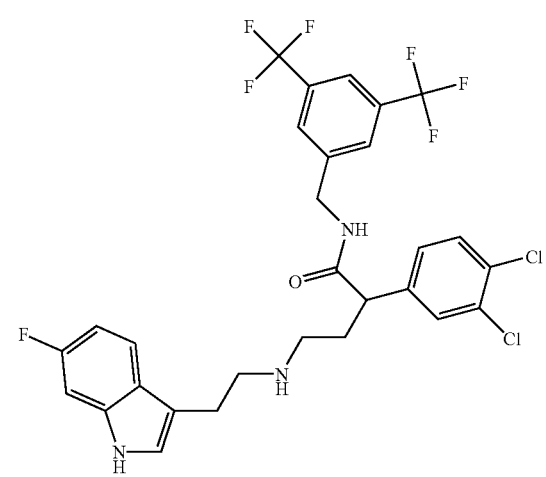 | 633.1184 | 634.0, 636.0 | C |
| 382 | 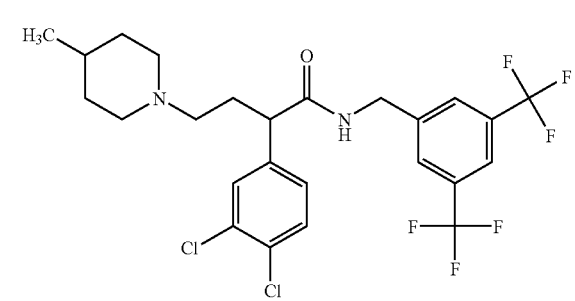 | 554.1326 | 555.0, 557.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 383 | 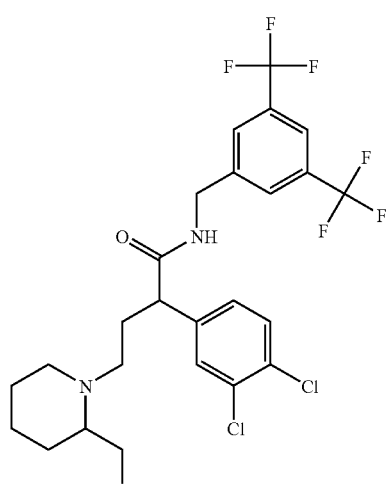 | 570.1275 | 571.1, 573.1 | C |
| 384 | 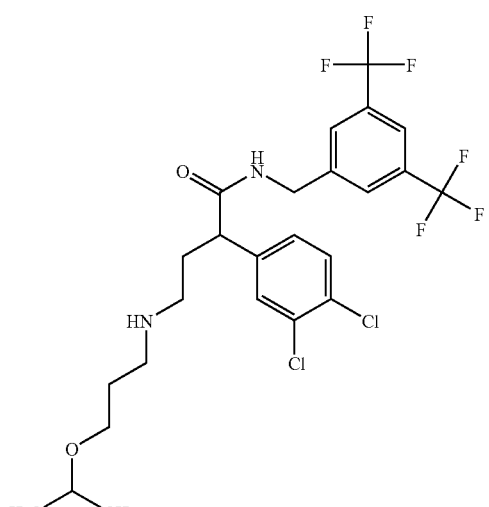 | 572.1432 | 573.1, 575.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 385 | | 615.1278 | 616.0, 618.0 | C |
| 386 | | 633.1184 | 634.0, 635.9 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 387 | 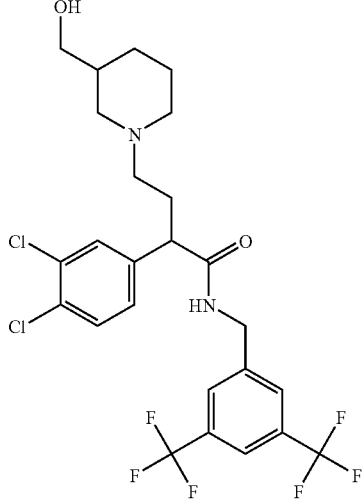 | 570.1275 | 571.1, 573.1 | C |
| 388 | 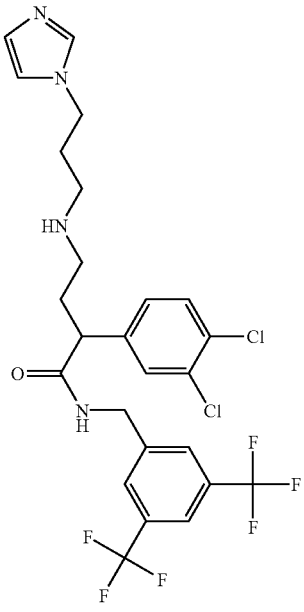 | 580.1231 | 581.1, 583.1 | C |
| 389 | 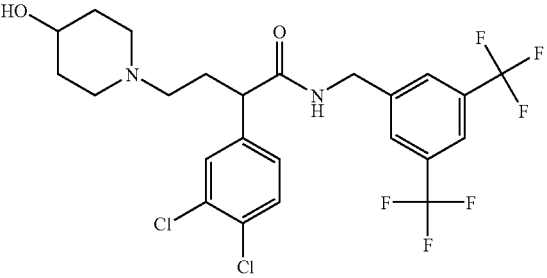 | 556.1119 | 557.1, 559.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 390 | | 666.1042 | 667.0, 669.0 | C |
| 391 | | 500.1609 | 501.1, 503.1 | C |
| 392 | | 592.1119 | 593.1, 595.0 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 393 | 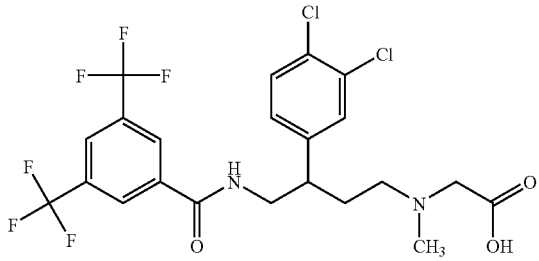 | 544.0755 | 545.0, 547.0 | C |
| 394 | 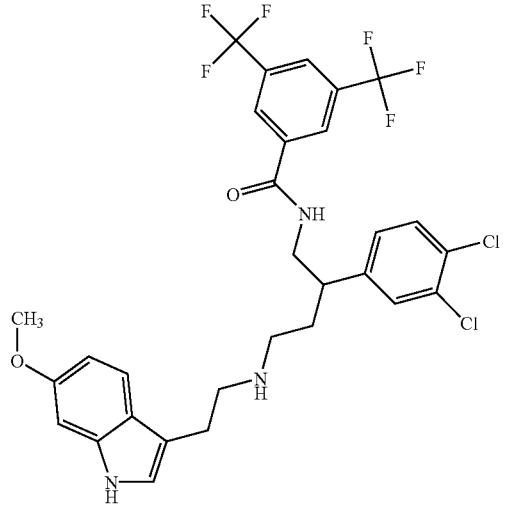 | 645.1384 | 645.9, 648.1 | C |
| 395 | 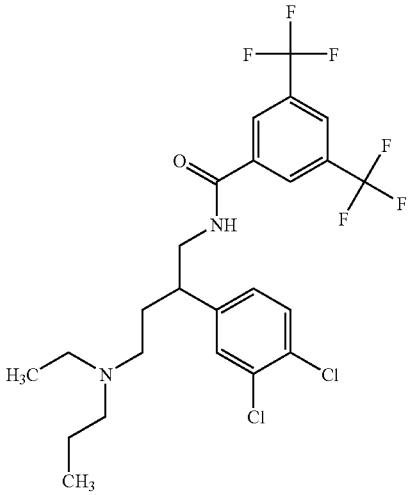 | 542.1326 | 543.1, 545.0 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 396 | | 645.1384 | 646.0, 648.1 | C |
| 397 | | 627.1278 | 628.0, 629.9 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 398 | 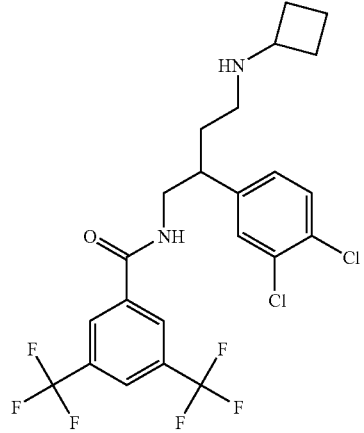 | 526.1013 | 527.1, 529.0 | C |
| 399 | 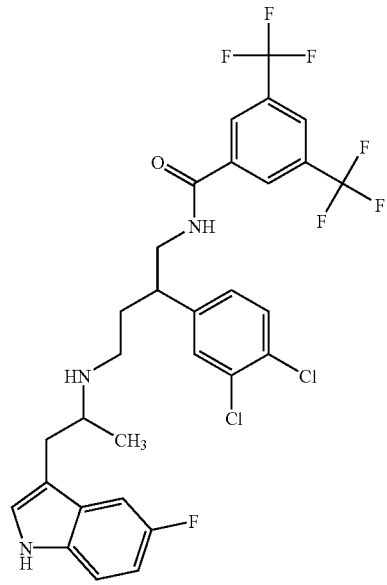 | 647.1341 | 648.0, 650.0 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 400 | 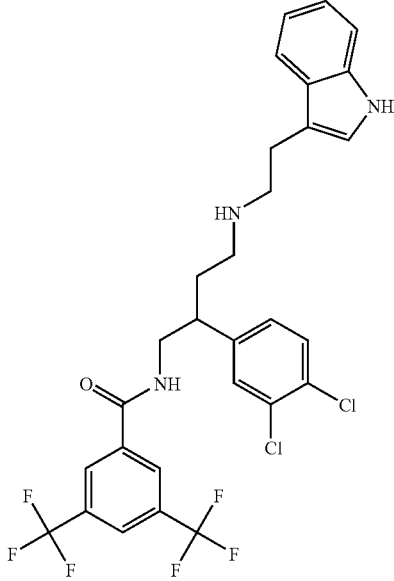 | 615.1278 | 616.0, 618.0 | C |
| 401 | 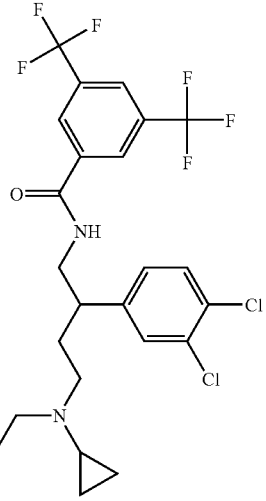 | 568.1482 | 569.1, 571.1 | C |
| 402 | 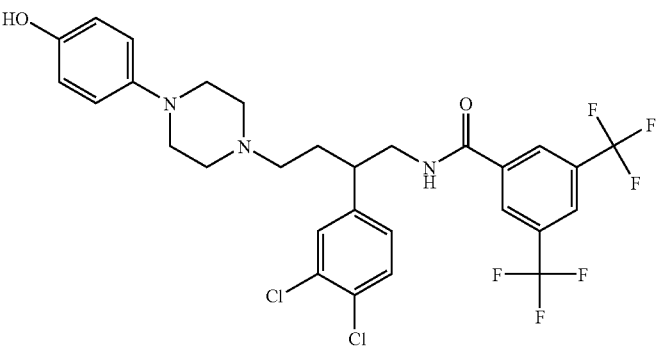 | 633.1384 | 634.2, 636.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 403 | | 540.1169 | 541.1, 543.1 | C |
| 404 | | 556.1119 | 557.1, 559.1 | C |
| 405 | | 554.1326 | 555.2, 557.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 406 | 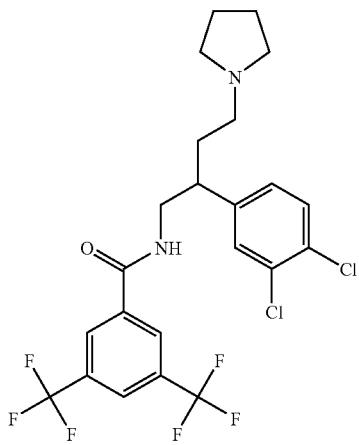 | 526.1013 | 527.1, 529.1 | C |
| 407 | 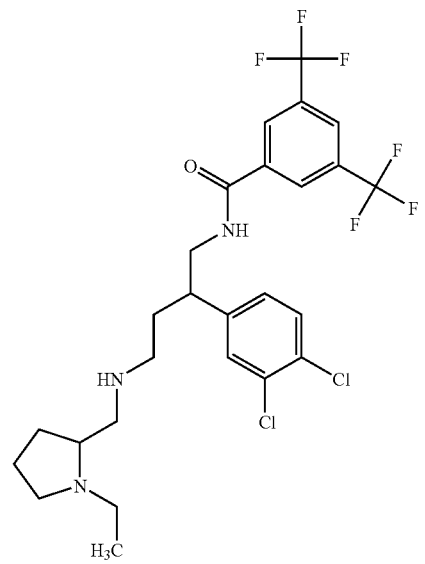 | 583.1591 | 584.1, 586.0 | C |
| 408 | 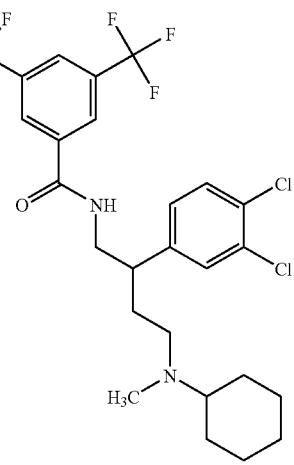 | 568.1482 | 569.1, 571.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 409 | 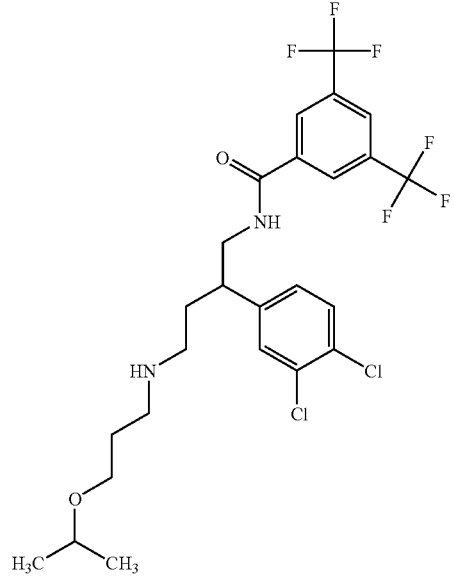 | 572.1432 | 573.1, 575.1 | C |
| 410 | 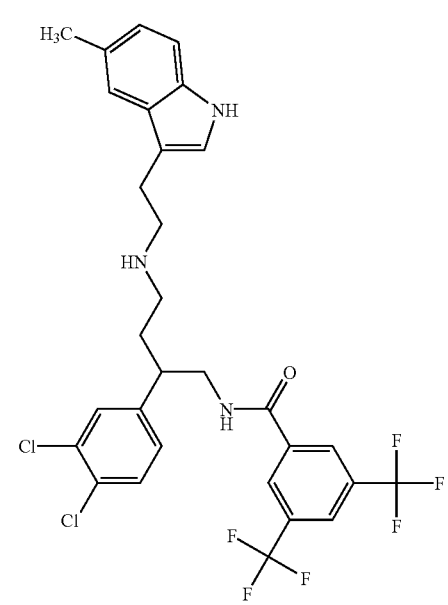 | 629.1435 | 630.0, 632.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 411 | | 569.1435 | 570.1, 572.1 | C |
| 412 | | 528.1169 | 529.1, 531.0 | C |
| 413 | | 583.1591 | 584.1, 586.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 414 | | 580.1231 | 581.1, 583.1 | C |
| 415 | | 633.1184 | 634.1, 636.0 | C |
| 416 | | 667.2167 | 668.0, 670.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 417 | 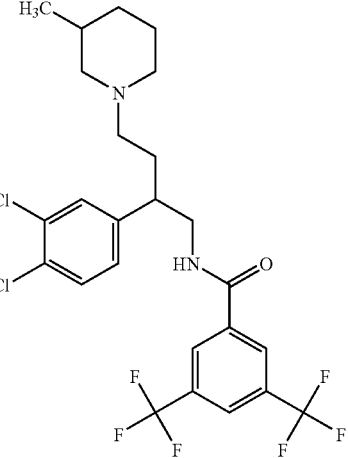 | 554.1326 | 555.2, 557.1 | C |
| 418 | 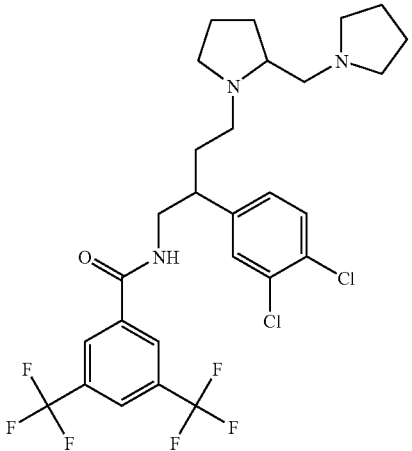 | 609.1748 | 610.0, 612.1 | C |
| 419 | 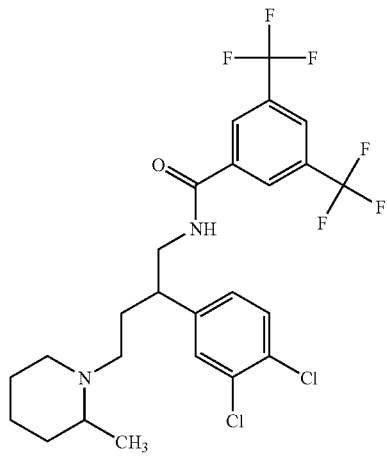 | 554.1326 | 555.1, 557.2 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 420 | 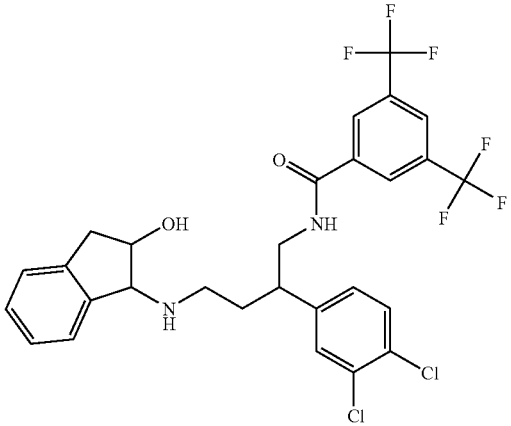 | 604.1119 | 605.0, 607.0 | C |
| 421 | 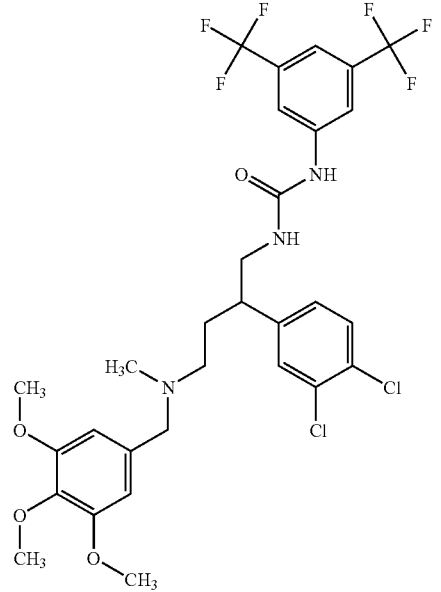 | 681.1595 | 681.9, 683.9 | B |
| 422 | 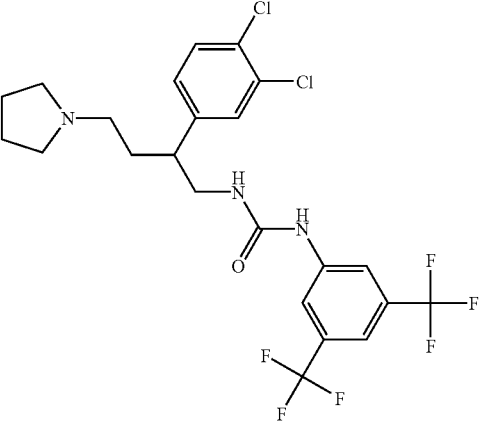 | 541.1122 | 542.1, 544.1 | B |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 423 | 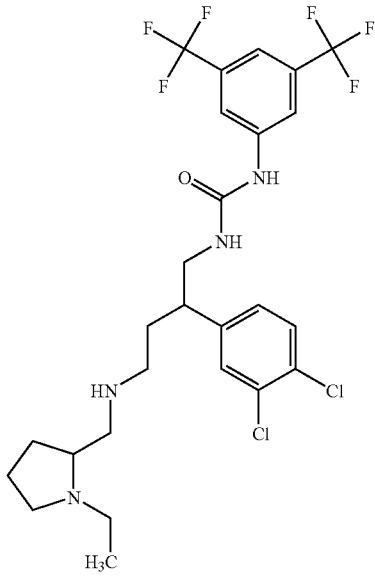 | 598.1700 | 599.1, 601.1 | B |
| 424 | 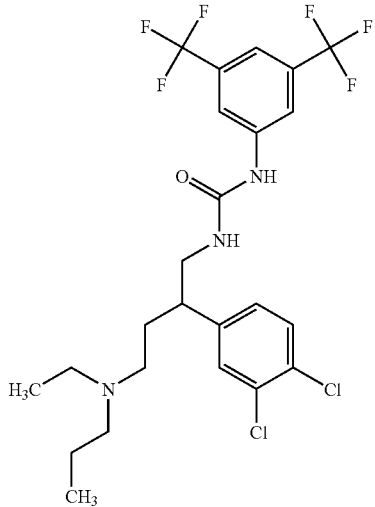 | 557.1435 | 558.1, 560.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 425 | | 572.1544 | 573.1, 575.1 | C |
| 426 | | 607.1228 | 608.1, 610.1 | C |
| 427 | | 557.1071 | 558.1, 560.1 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 428 | | 600.1493 | 601.1, 603.0 | C |
| 429 | | 652.2170 | 653.1, 655.1 | C |
| 430 | | 624.1857 | 625.1, 627.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 431 | 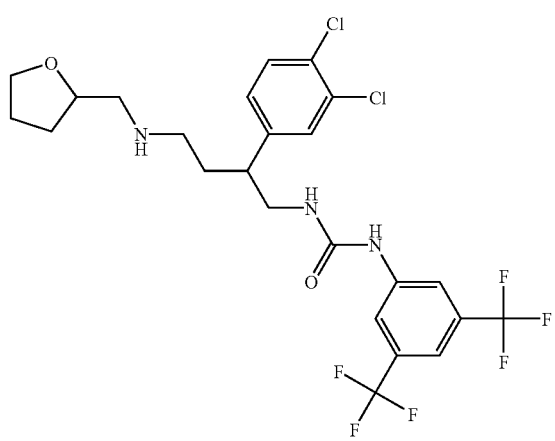 | 571.1228 | 572.1, 574.0 | C |
| 432 | 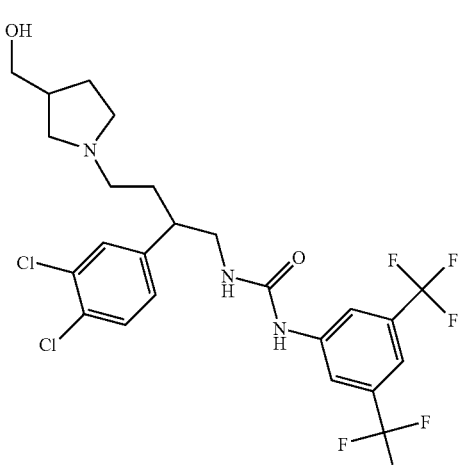 | 571.1228 | 572.2, 574.1 | C |
| 433 | 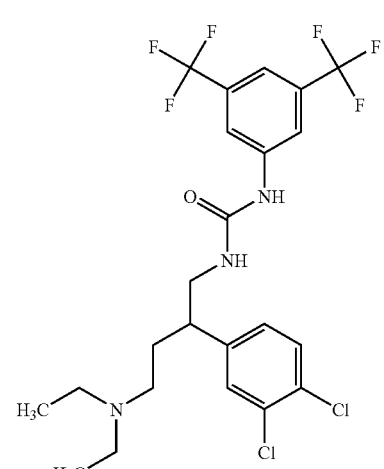 | 543.1278 | 544.1, 546.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 434 | 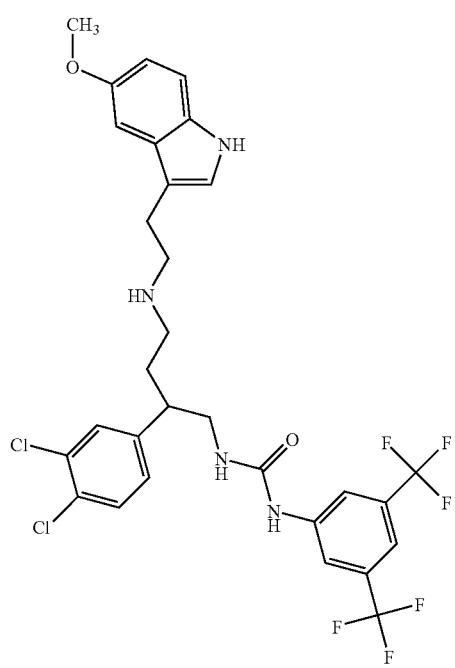 | 660.1493 | 661.1, 663.1 | C |
| 435 | 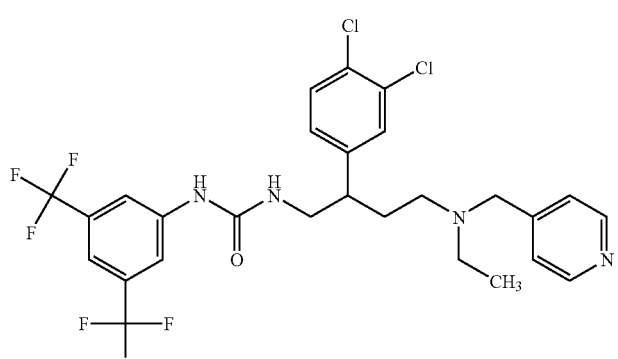 | 606.1387 | 607.1, 609.0 | C |
| 436 | 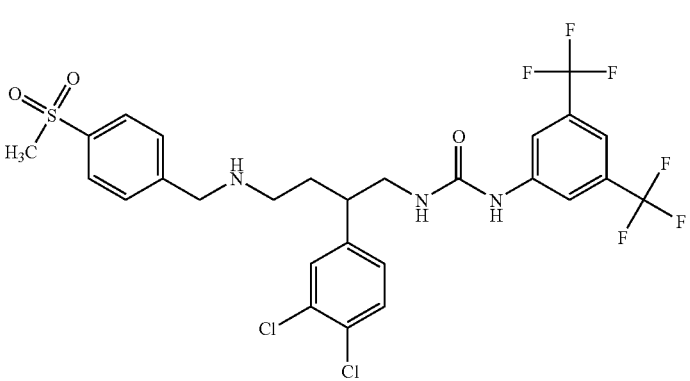 | 655.0897 | 656.0, 658.0 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 437 | 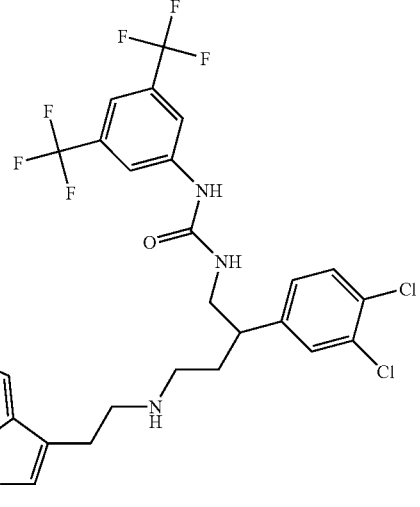 | 660.1493 | 661.0, 663.0 | C |
| 438 | 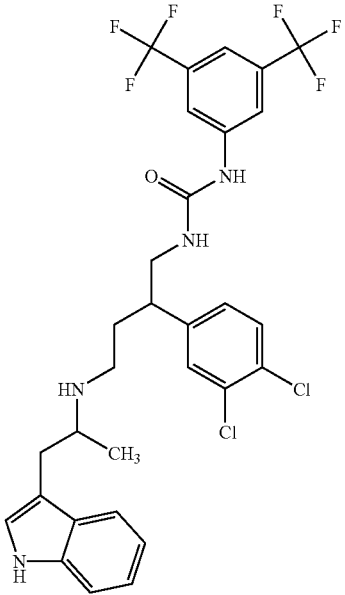 | 644.1544 | 645.0, 647.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 439 | 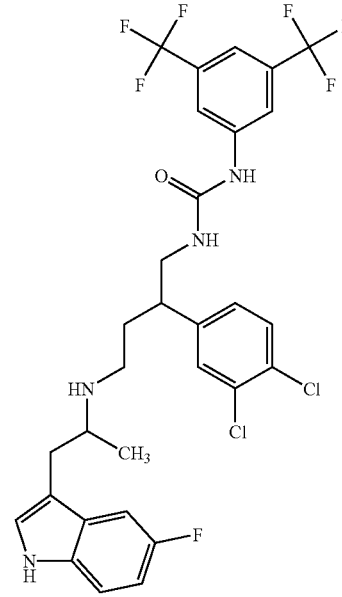 | 662.1450 | 663.0, 665.0 | C |
| 440 | 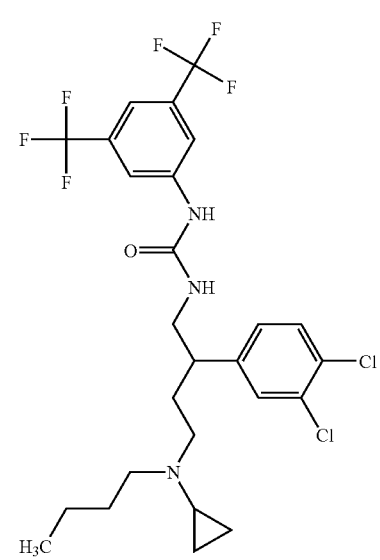 | 583.1591 | 584.2, 586.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 441 | 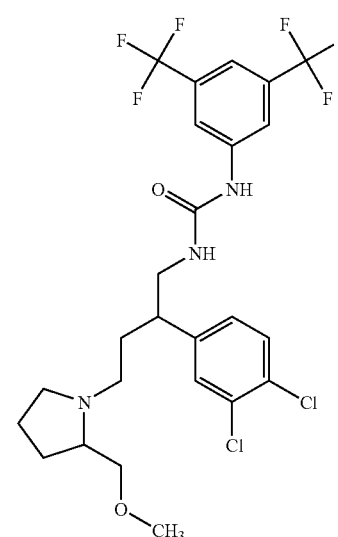 | 585.1384 | 586.2, 586.1 | C |
| 442 | 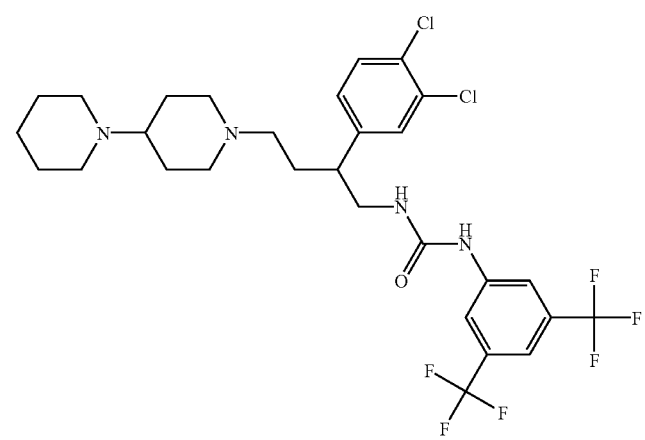 | 638.2013 | 639.2, 641.1 | B |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 443 | | 584.2949 | 585.2 | B |
| 444 | | 555.1278 | 556.2, 558.1 | B |
| 445 | | 501.2214 | 502.2 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 446 | 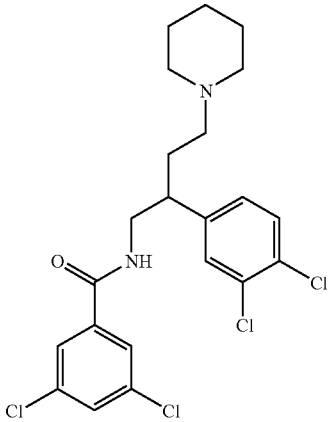 | 472.0642 | 473.1, 475.1, 477.2 | C |
| 447 | 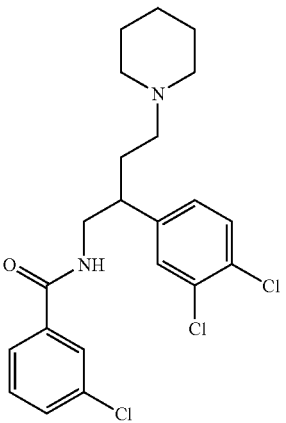 | 438.1032 | 439.1, 441.1, 443.1 | C |
| 448 | 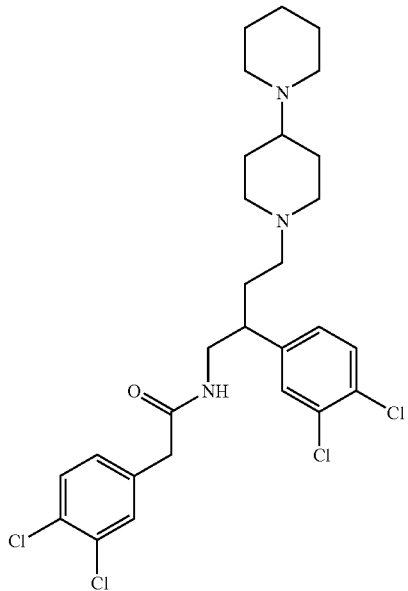 | 569.1534 | 570.0, 572.1, 574.0 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---|---|---|---|---|
| 449 | | 472.1296 | 473.2, 475.1 | C |
| 450 | | 418.1578 | 419.1, 421.1 | C |
| 451 | | 515.2470 | 516.2, 518.1 | C |

TABLE I-continued
MCH Antagonist Compounds- A: Ki = 0.4–50 nM; B: Ki = 51–500 nM; C: Ki = 501–2,500 nM
| Example | Chemistry | Exact MS, calc. | MS (ESI) found | Activity |
|---|---|---|---|---|
| 452 | 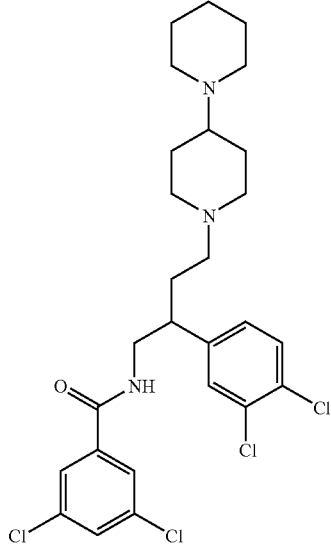 | 555.1377 | 556.1, 558.2 | C |
| 453 | 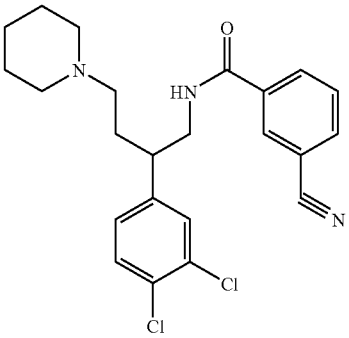 | 429.1374 | 430.2, 432.1 | C |
| 454 | 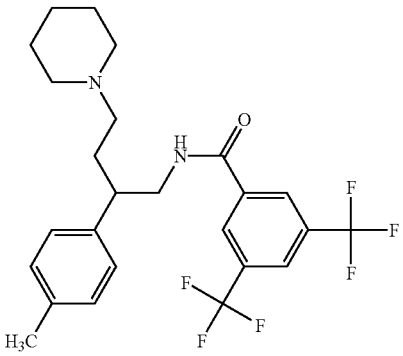 | 486.2105 | 487.2 | C |

TABLE I-continued

MCH Antagonist Compounds- A: Ki = 0.4–50 nM; B: Ki = 51–500 nM; C: Ki = 501–2,500 nM

| Example | Chemistry | Exact MS, calc. | MS (ESI) found | Activity |
|---------|-----------|-----------------|----------------|----------|
| 455 | | 422.1328 | 423.1, 425.1 | C |
| 456 | | 432.1735 | 433.1, 435.1 | C |
| 457 | | 623.1904 | 624.1 | C |

What is claimed is:

1. A compound having the structure shown in Formula I:

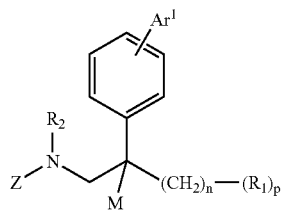

Formula I wherein:
Ar$^1$=unsubstituted or substituted phenyl, wherein the substituents number from 0 to 5, may be the same or different and are independently selected from the group consisting of H, CN, F, Cl, Br, I, OH;
M is H or R with R being a C$_1$–C$_6$ straight chain alkyl or branched alkyl or a C$_3$–C$_7$ cycloalkyl;
Z=

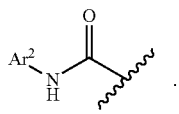

where Ar$^2$ is an unsubstituted or substituted phenyl wherein the substituents number from 0 to 5, may be the same or different and are independently selected from the group consisting F, Cl, Br, I, R, and CF$_3$;
n=0 to 6;
p=1;
R$_1$ may be the same or different and is independently selected from the group consisting of NH$_2$; NHR; N(R)$_2$;

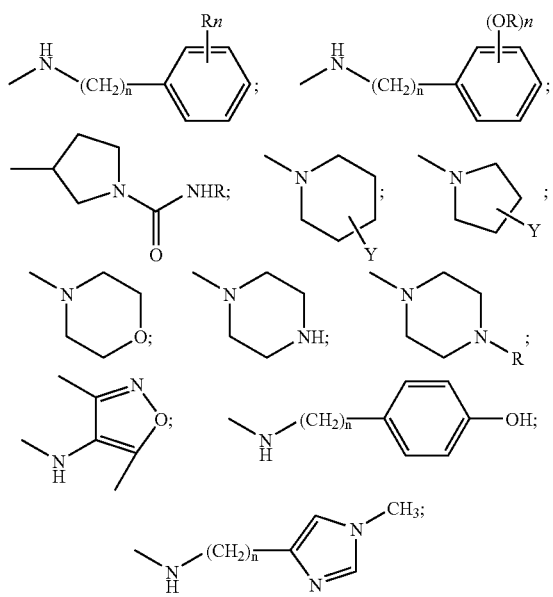

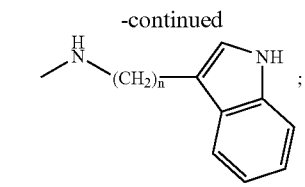

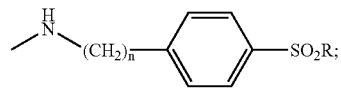

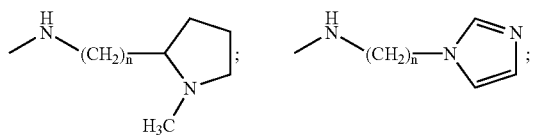

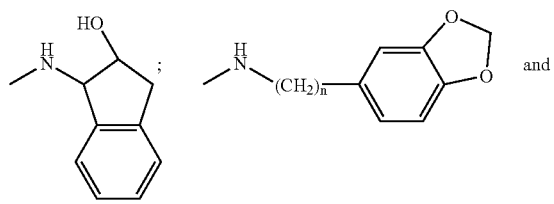

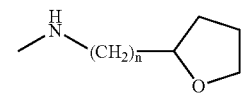

where n is defined above;
and R$_2$ is H or alkyl.

2. The compound of claim 1, wherein M is H.

3. The compound of claim 1, wherein Ar$^1$ is 4-phenyl.

4. The compound of claim 3, wherein said phenyl is substituted on the ring with at least one of CN, F and Cl or combinations thereof.

5. The compound of claim 3, wherein said substituents are in position 3 on the ring with respect to said ring's attachment to the benzylic position in Formula I.

6. The compound of claim 1, wherein Z is Ar$^2$—NH—CO, where Ar$^2$ is phenyl.

7. The compound of claim 6, wherein said phenyl is substituted with one or more moieties which number 0 to 5, may be the same or different and are independently selected from the group consisting of F, Cl, Br, I, and CF$_3$.

8. The compound of claim 7, wherein said substituent on Ar$^2$ is F, or Cl.

9. The compound of claim 1, wherein R is a C$_1$–C$_4$ straight chain alkyl, a C$_1$–C$_4$ branched alkyl or a C$_3$–C$_7$ cycloalkyl.

10. The compound of claim 9, wherein R is methyl, ethyl or propyl.

11. The compound of claim 9, wherein R is isopropyl.

12. The compound of claim 9, wherein R is cyclobutyl.

13. The compound of claim 1, wherein n is 2–4.

14. The compound of claim 1, wherein n is 2.

15. The compound of claim 1, wherein R$_1$ is selected from the group consisting of NHMe; NHEt; NMe$_2$; NH-cyclopropyl; NH-cyclobutyl; and NH-cyclopentyl.

16. A compound having the structure shown in Formula II:

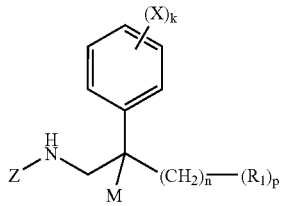

wherein:
M is H or R; with R being a $C_1$–$C_6$ straight chain alkyl or branched alkyl or a $C_3$–$C_7$ cycloalkyl;
k=1;
p=1;
n=0 to 6;
Z=

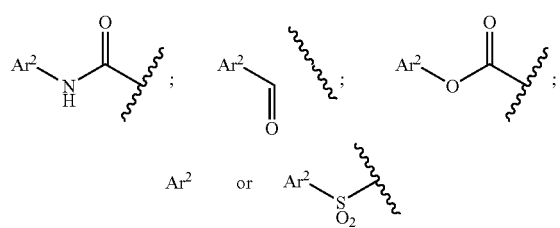

where $Ar^2$ is an unsubstituted or substituted phenyl wherein the substituents number from 0 to 5, may be the same or different and are independently selected from the group consisting F, Cl, Br, I, R, and $CF_3$;
$R_1$ may be the same or different and is independently selected from the group consisting of $NH_2$; NHR; $N(R)_2$;

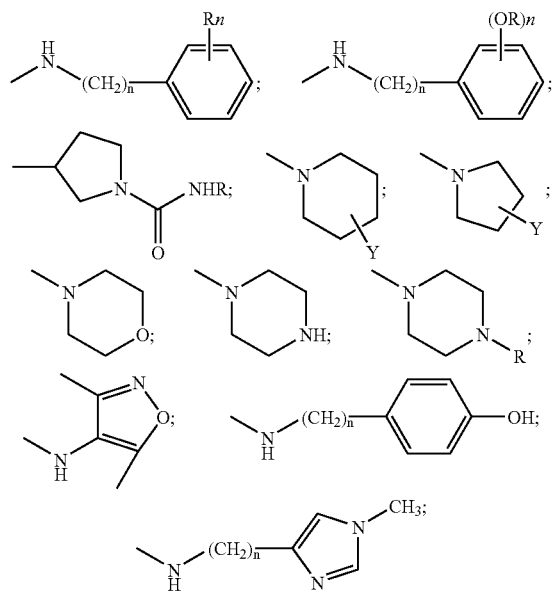

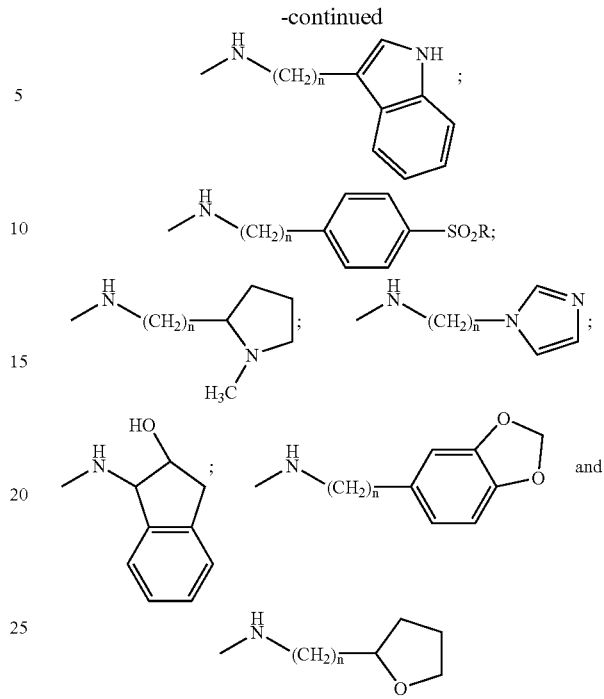

where n is defined above;
and X is phenyl.

17. The compound of claim 16 wherein M is H.

18. The compound of claim 16, wherein Z is $Ar^2$—NH—CO, where $Ar^2$ is phenyl.

19. The compound of claim 18, wherein said phenyl is substituted with one or more moieties which number 0 to 5, may be the same or different and are independently selected from the group consisting of F, Cl, Br, I, and $CF_3$.

20. The compound of claim 16, wherein R is a $C_1$–$C_4$ straight chain or branched alkyl.

21. The compound of claim 16, wherein n is 2.

22. A pharmaceutical composition comprising as an active ingredient at least one compound of claim 1 or claim 16 and additionally comprising a pharmaceutically acceptable carrier.

23. A compound being selected from the group of compounds with structures listed below:

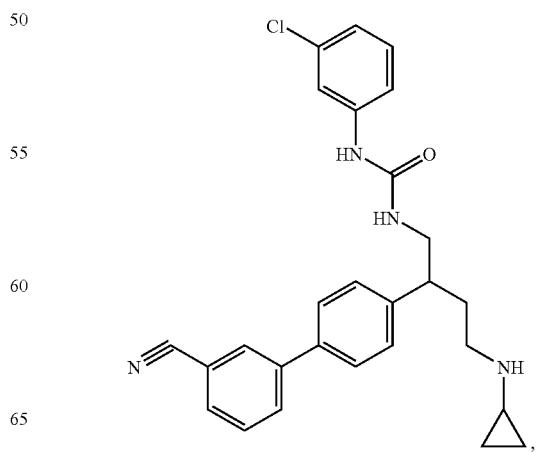

-continued
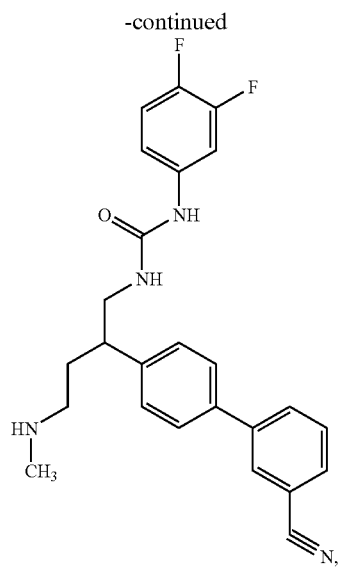
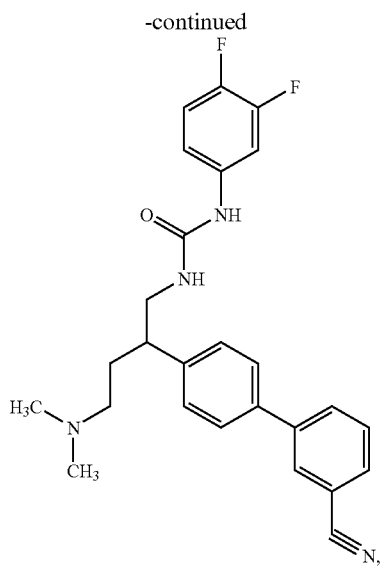
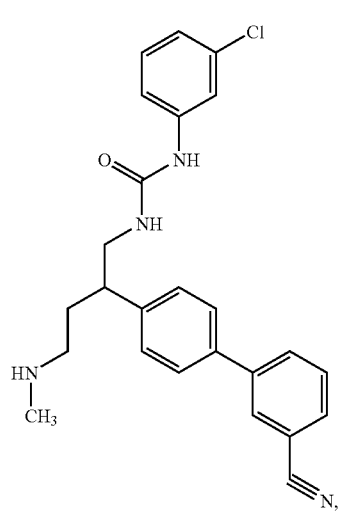
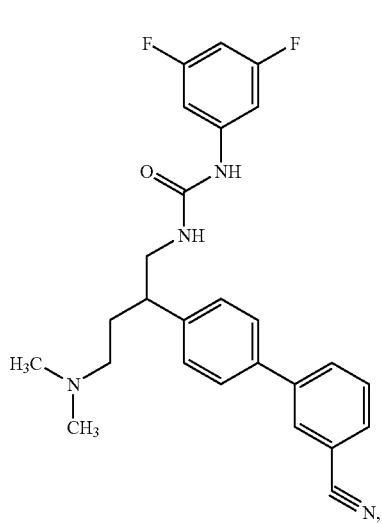
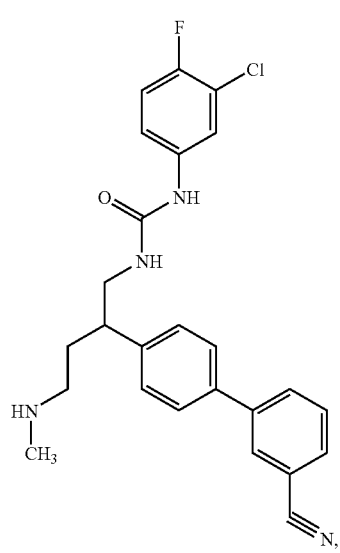
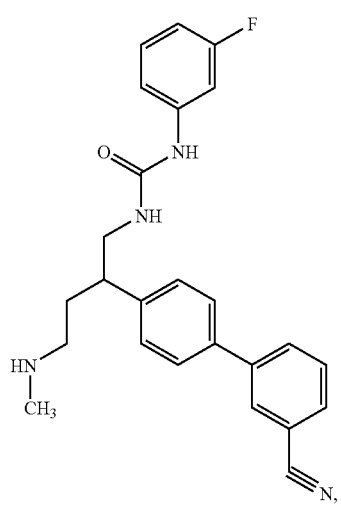

-continued
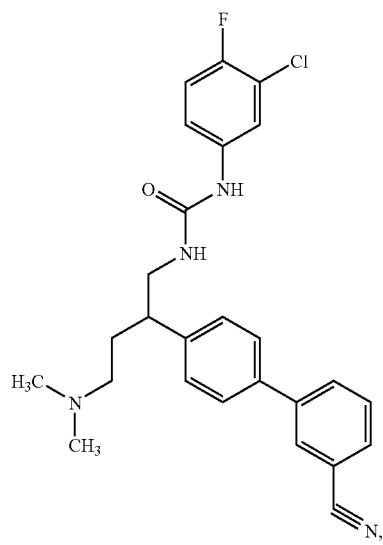
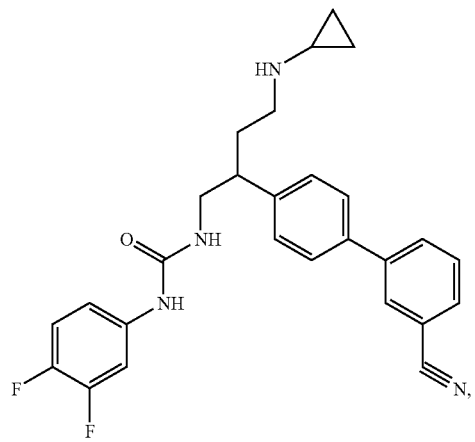
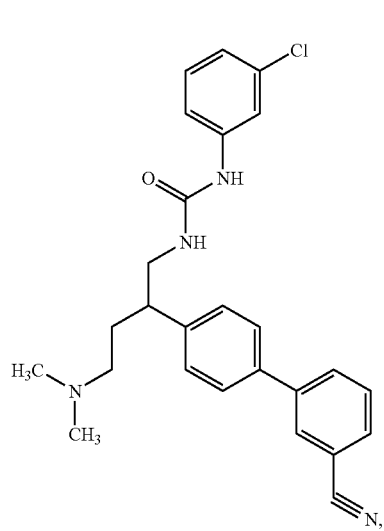
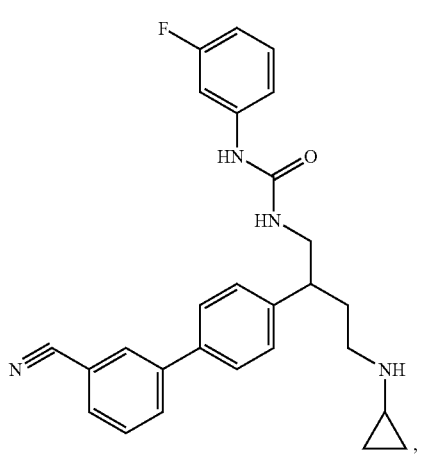
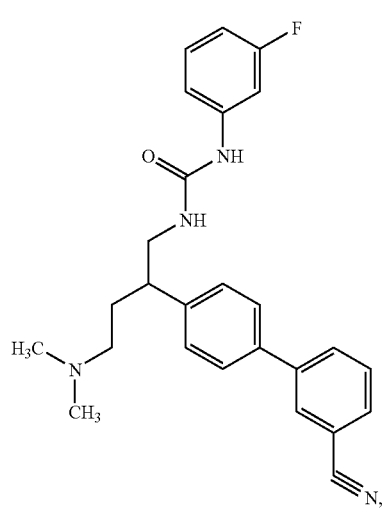
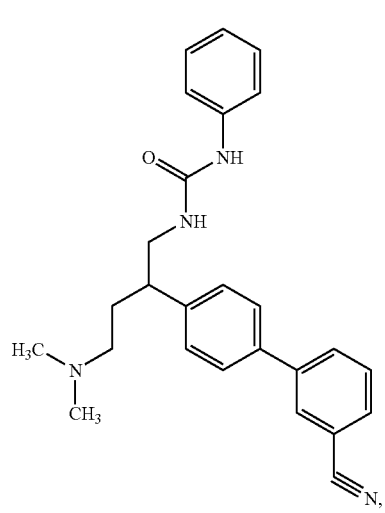

383
-continued
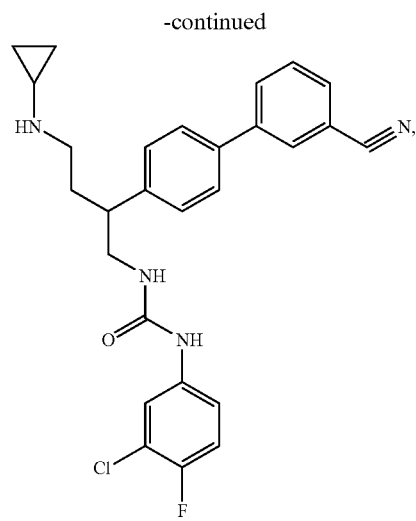
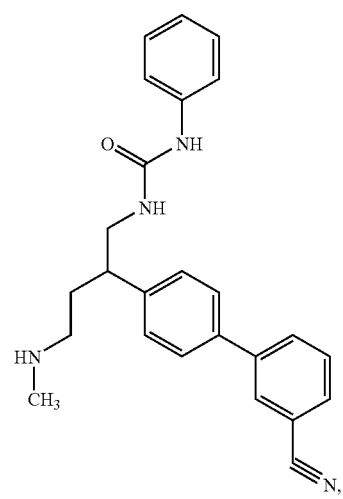
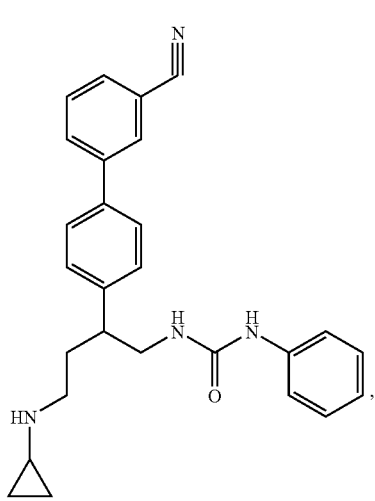
384
-continued
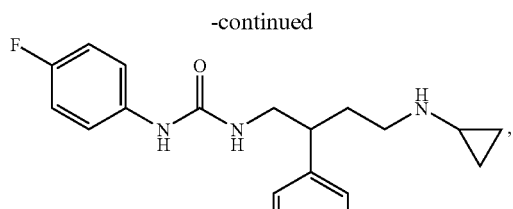
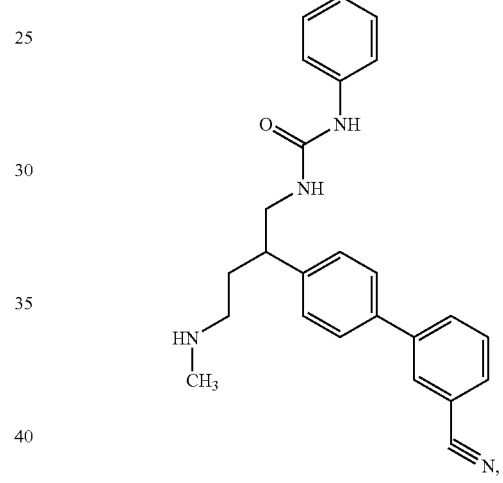
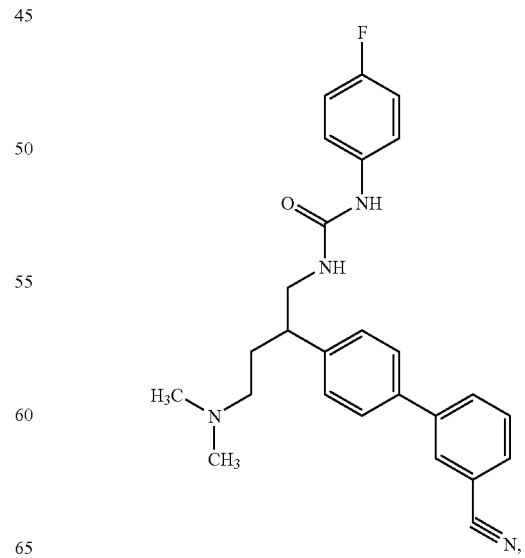

385 386
-continued -continued
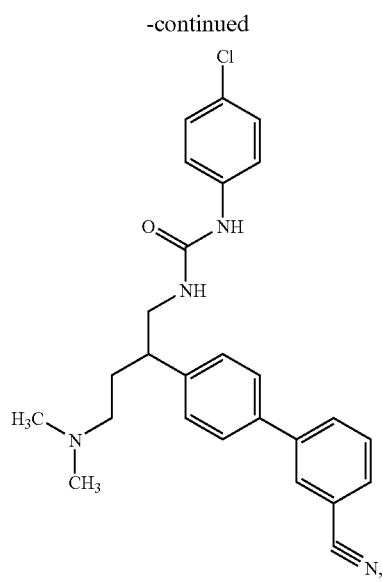
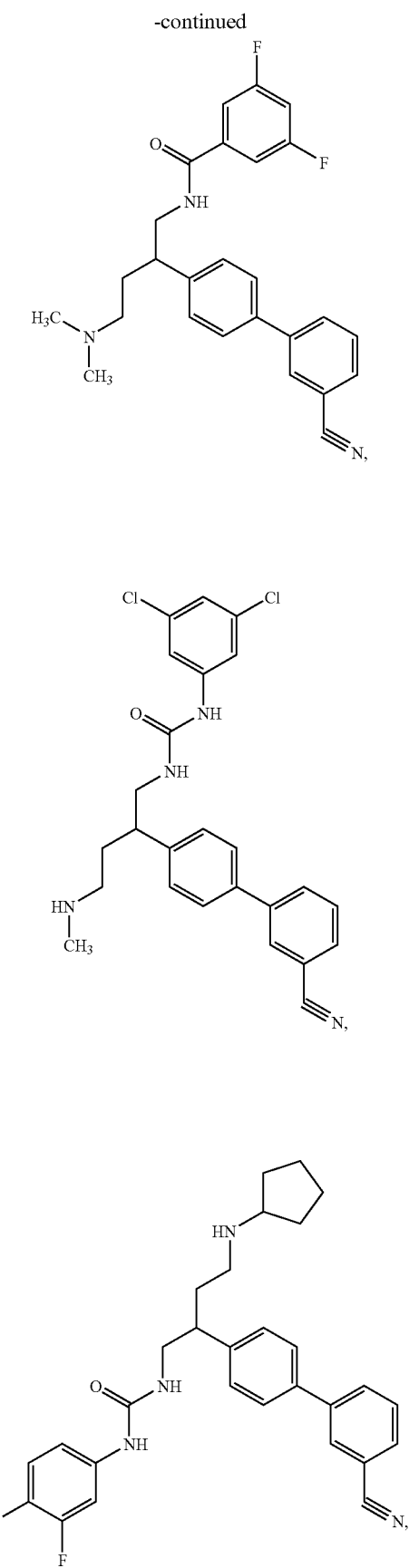

-continued
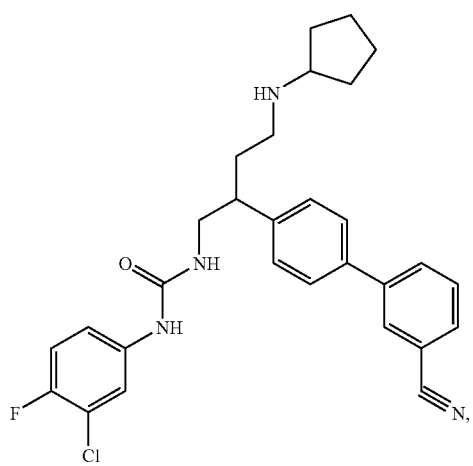
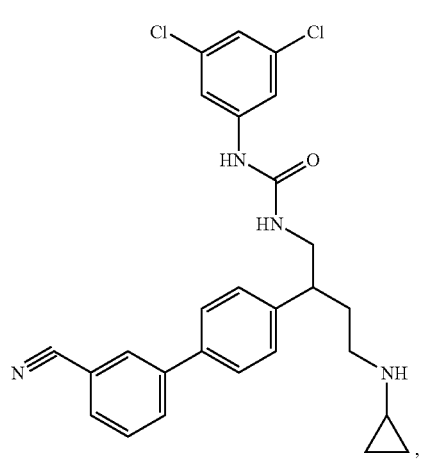
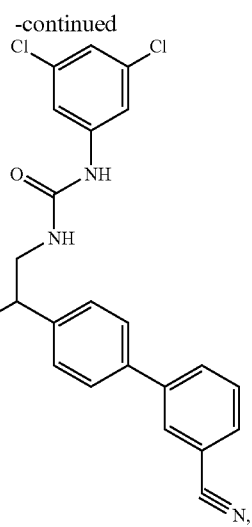
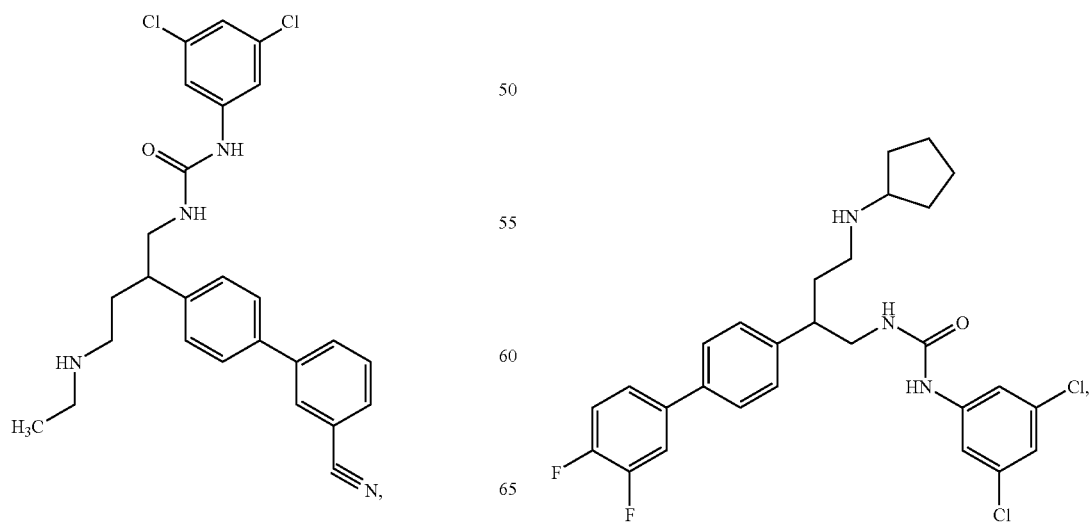

389
-continued
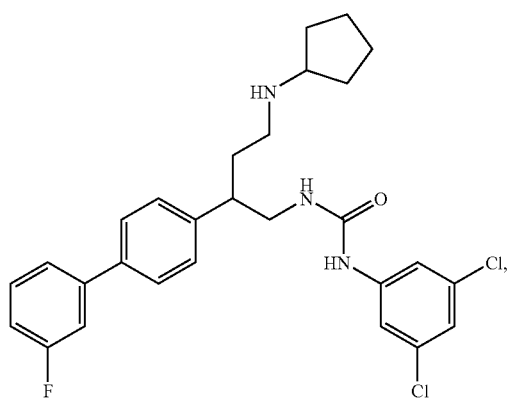
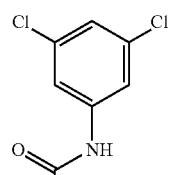
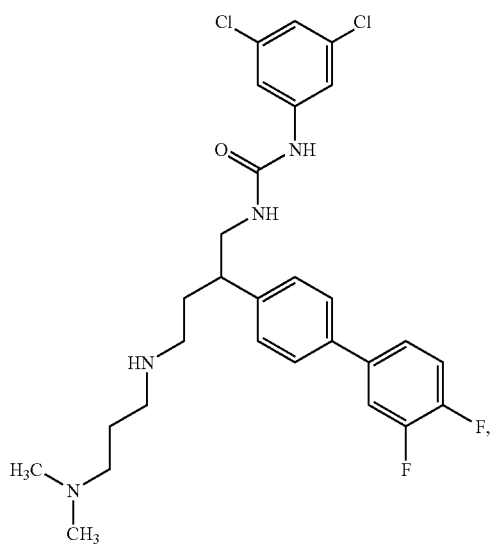
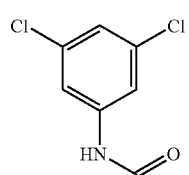
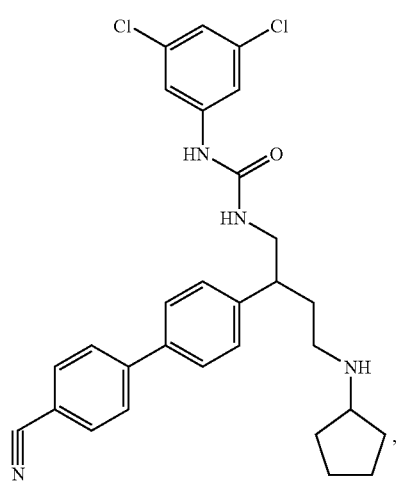
390
-continued
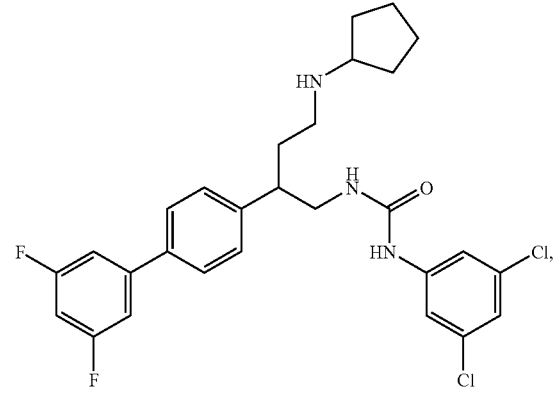
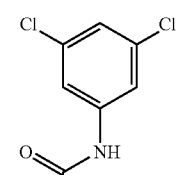
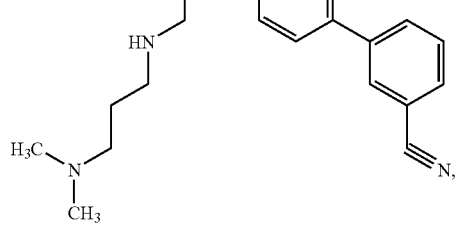
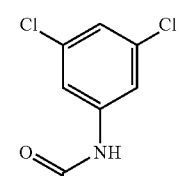
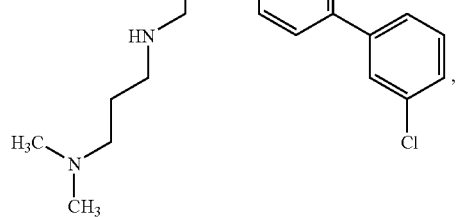

-continued

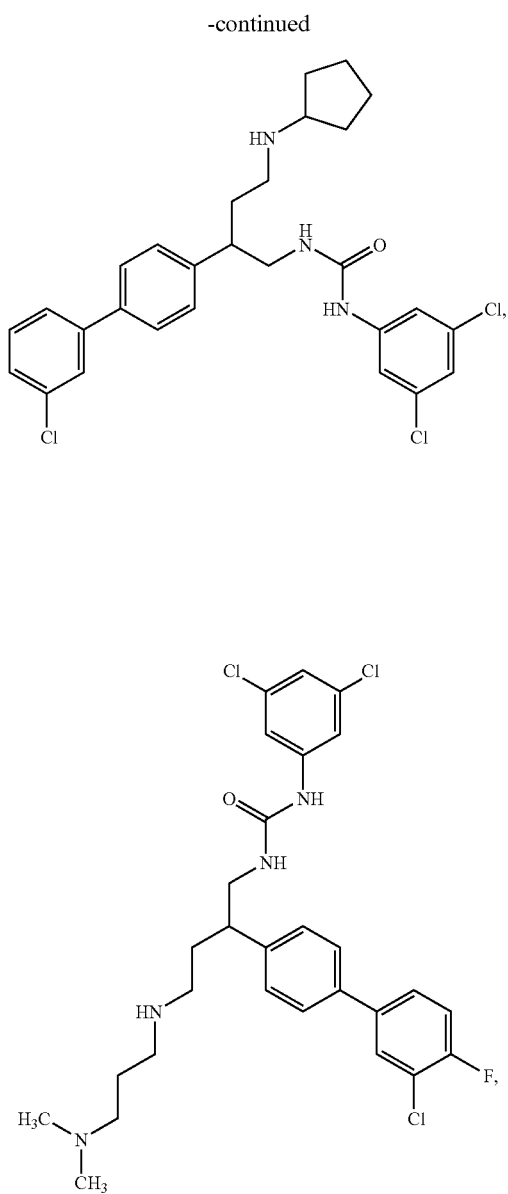

or

-continued

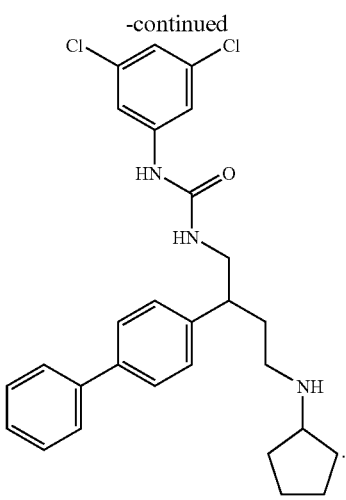

24. A pharmaceutical composition for treating diabetes and obesity, said composition comprising therapeutically effective amounts of at least one compound of claim 23 and a pharmaceutically acceptable carrier.

25. A pharmaceutical composition to treat obesity, said composition comprising:
   therapeutically effective amounts of at least one compound of claim 1 or of claim 16, or a pharmaceutically acceptable salt of said compound;
   therapeutically effective amounts of one or more compounds, said compounds being selected from the group consisting of a $\beta_3$ agonist, a thermometric agent, an antiobesity agent, an anorectic agent and an NPY antagonist; and
   a pharmaceutically acceptable carrier.

26. A pharmaceutical composition to treat obesity, said composition comprising:
   therapeutically effective amounts of at least one compound of claim 1 of claim 16, or a pharmaceutically acceptable salt of said compound;
   therapeutically effective amounts of one or more compounds selected from the group consisting of an analdose reductase inhibitor, a glycogen phosphorylase inhibitor, a sorbitol dehydrogenase inhibitor, a protein tyrosine phosphatase 1B inhibitor, a dipeptidyl protease inhibitor, insulin, an insulin mimetic, metformin, acarbose, a PPAR-gamma ligand. rosaglitazone, pioglitazone, GW-1929, a sulfonylurea, glipazide, glybunde, and chlorpropamide; and
   a pharmaceutically acceptable carrier.

* * * * *

UNITED STATES PATENT AND TRADEMARK OFFICE
CERTIFICATE OF CORRECTION

PATENT NO. : 7,034,056 B2  
APPLICATION NO. : 10/101136  
DATED : April 25, 2006  
INVENTOR(S) : Douglas W. Hobbs Page 1 of 2

It is certified that error appears in the above-identified patent and that said Letters Patent is hereby corrected as shown below:

In the Claims:

Claim 1, col. 375, lines 45-47:     Please correct all the structures shown to only these:

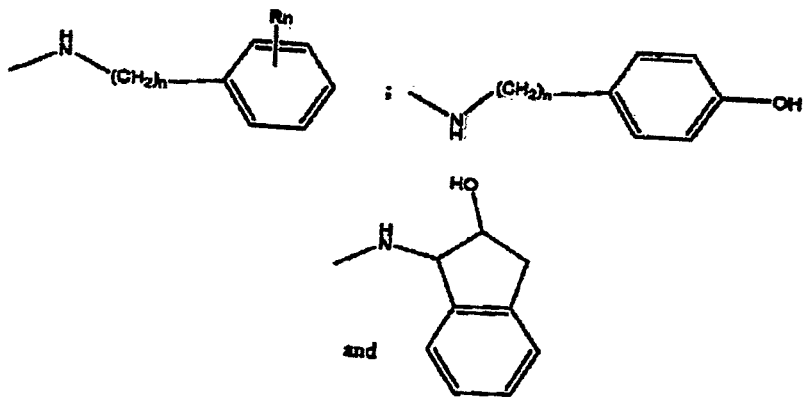

Claim 1, col. 376, lines 1-34:     Please remove all the structures.

Claim 16, col. 377, lines 20-34:     Please correct all the structures shown to only these:

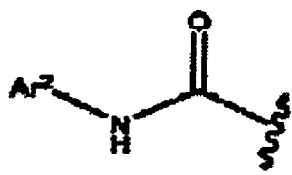

UNITED STATES PATENT AND TRADEMARK OFFICE
CERTIFICATE OF CORRECTION

PATENT NO. : 7,034,056 B2
APPLICATION NO. : 10/101136
DATED : April 25, 2006
INVENTOR(S) : Douglas W. Hobbs It is certified that error appears in the above-identified patent and that said Letters Patent is hereby corrected as shown below:

Claim 16, col. 377, lines 43-65:  Please correct all the structures shown to only these:

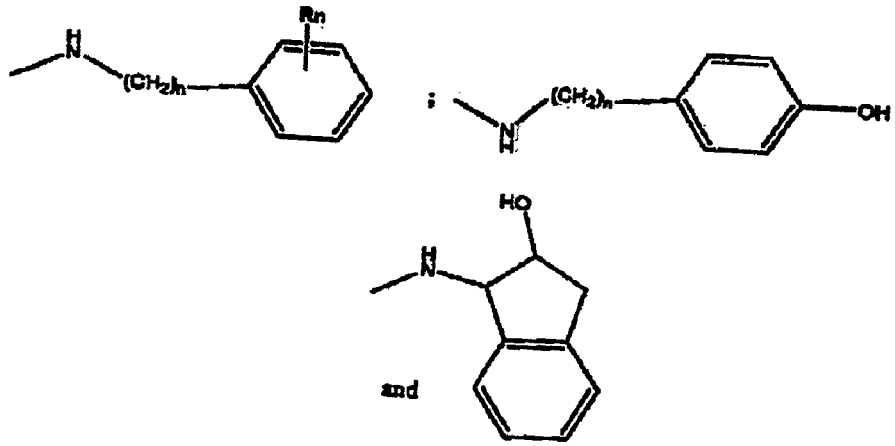

Claim 16, col. 378, lines 1-29:  Please remove all the structures.

Claim 25, col. 392, line 33:  Please correct "thermometric" to --thryomimetic--.

Claim 26, col. 392, line 49:  Please correct "glybunde" to --glyburide--.

Signed and Sealed this

Thirty-first Day of October, 2006

JON W. DUDAS
*Director of the United States Patent and Trademark Office*